United States Patent
Sarlah et al.

(10) Patent No.: US 12,084,456 B2
(45) Date of Patent: Sep. 10, 2024

(54) ISOCARBOSTYRIL ALKALOIDS AND FUNCTIONALIZATION THEREOF

(71) Applicant: The Board of Trustees of the University of Illinois, Urbana, IL (US)

(72) Inventors: David Sarlah, Champaign, IL (US); Tanner W. Bingham, Urbana, IL (US); Lucas William Hernandez, Urbana, IL (US)

(73) Assignee: The Board of Trustees of the University Of Illinois, Urbana, IL (US)

( * ) Notice: Subject to any disclaimer, the term of this patent is extended or adjusted under 35 U.S.C. 154(b) by 704 days.

(21) Appl. No.: 17/299,365

(22) PCT Filed: Dec. 4, 2019

(86) PCT No.: PCT/US2019/064388
§ 371 (c)(1),
(2) Date: Jun. 3, 2021

(87) PCT Pub. No.: WO2020/117894
PCT Pub. Date: Jun. 11, 2020

(65) Prior Publication Data
US 2022/0064176 A1    Mar. 3, 2022

Related U.S. Application Data

(60) Provisional application No. 62/775,521, filed on Dec. 5, 2018.

(51) Int. Cl.
C07D 491/056 (2006.01)
B01J 31/22 (2006.01)

(52) U.S. Cl.
CPC .......... *C07D 491/056* (2013.01); *B01J 31/22* (2013.01); *B01J 2531/16* (2013.01)

(58) Field of Classification Search
CPC .... C07D 491/056; B01J 31/22; B01J 2531/16
See application file for complete search history.

(56) References Cited

U.S. PATENT DOCUMENTS

| | | |
|---|---|---|
| 2004/0127467 A1 | 7/2004 | Pettit et al. |
| 2004/0167155 A1 | 8/2004 | Molinari et al. |
| 2006/0058337 A1 | 3/2006 | Steffan et al. |
| 2014/0234345 A1* | 8/2014 | Mercure ............ C07D 491/056 546/65 |

FOREIGN PATENT DOCUMENTS

| | | |
|---|---|---|
| WO | 2008043846 A2 | 4/2008 |
| WO | 2009026961 A1 | 3/2009 |

OTHER PUBLICATIONS

Borra et al., "Isolation, Synthesis, and Semisynthesis of Amaryllidaceae Constituents from Narcissus and Galanthus sp.: De Novo Total Synthesis of 2-epi-Narciclasine," J Nat Prod., 81(6):1451-1459, Jun. 2018.
Cai et al., "Asymmetric Cinnamylation of N-Tert-Butanesulfinyl Imines With Cinnamyl Acetates: Total Syntheses of (+)-Lycoricidine and (+)-7-Deoxypancratistatin," Chem. Commun., 53(25):3520--3523, Feb. 2017.
Chen et al., "Pd-Catalyzed Ortho C—H Hydroxylation of Benzaldehydes Using a Transient Directing Group," Org. Lett., 19(23):6280-6283, Nov. 2017.
Hernandez et al., "Nickel-Catalyzed Dearomative trans-1,2-Carboamination," J Am Chem Soc., 140(13):4503-4507, Apr. 2018.
Hernandez et al., "Synthesis of (+)-Pancratistatins via Catalytic Desymmetrization of Benzene," J Am Chem Soc., 139(44):15656-15659, Oct. 2017.
International Search Report and Written Opinion of the ISA/US in PCT/US2019/064388, dated Mar. 12, 2020; 11pgs.
Potter et al., "Total Synthesis of (+)-Pancratistatin by the Rh(III)-Catalyzed Addition of a Densely Functionalized Benzamide to a Sugar-Derived Nitroalkene," Org Lett., 19(11):2985-2988, Jun. 2017.
Southgate et al., "Dearomative Dihydroxylation with Arenophiles," Nat Chem., 8(10):922-928, Oct. 2016.
Southgate et al., "Total Synthesis of Lycoricidine and Narciclasine by Chemical Dearomatization of Bromobenzene," Angew Chem Int Ed Engl., 56(47):15049-15052, Nov. 2017.

* cited by examiner

*Primary Examiner* — Timothy R Rozof
(74) *Attorney, Agent, or Firm* — Haukaas Fortius PLLC; Michael Haukaas

(57) ABSTRACT

Enantioselective total syntheses of the anticancer isocarbostyril alkaloids (+)-7-deoxypancratistatin, (+)-pancratistatin, (+)-lycoricidine, and (+)-narciclasine are described. Our strategy for accessing this unique class of natural products is based on the development of a Ni-catalyzed dearomative trans-1,2-carboamination of benzene. The effectiveness of this dearomatization approach is notable, as only two additional olefin functionalizations are needed to construct the fully decorated aminocyclitol cores of these alkaloids. Installation of the lactam ring has been achieved through several pathways and a direct interconversion between natural products was established via a late-stage C-7 cupration. Using this synthetic blueprint, we were able to produce natural products on a gram scale and provide tailored analogs with improved activity, solubility, and metabolic stability.

21 Claims, 2 Drawing Sheets

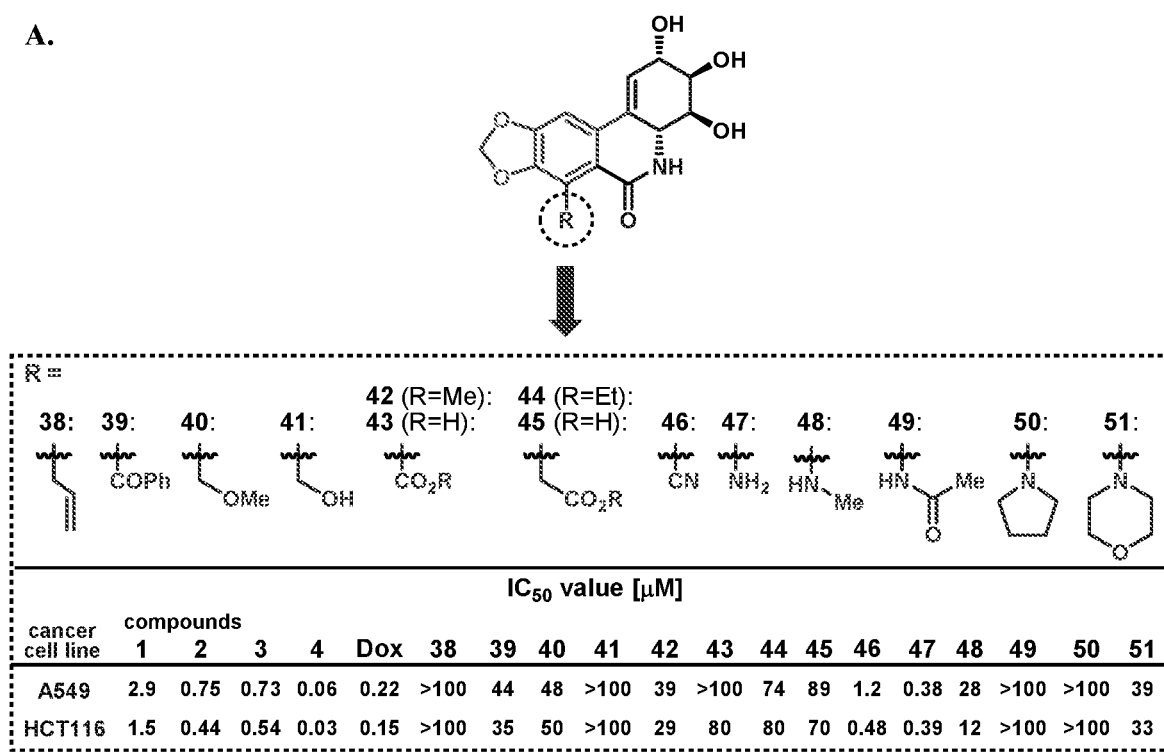
A.
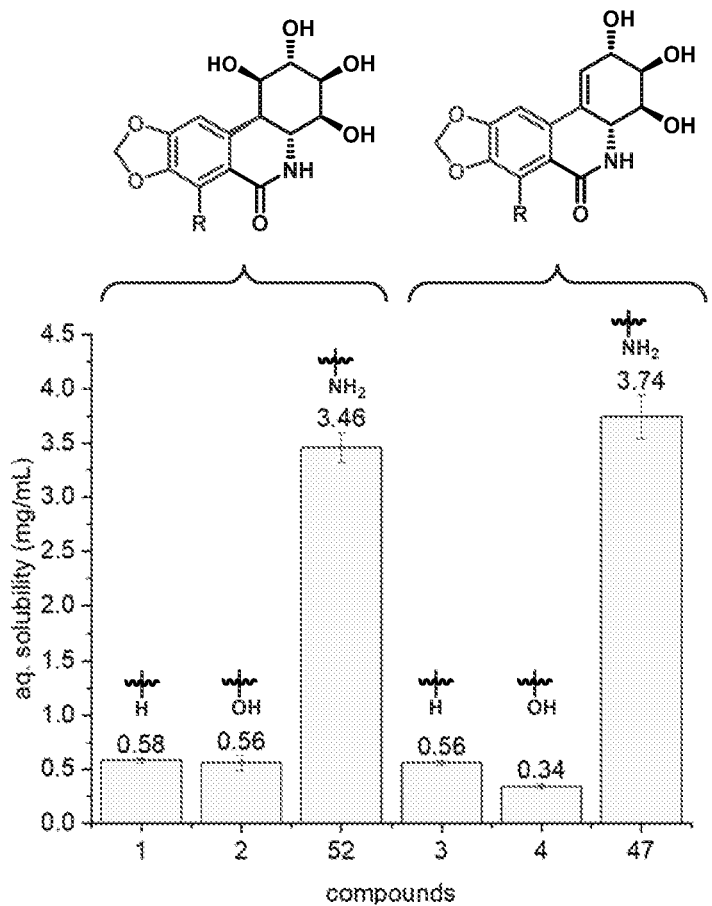
B.

C.
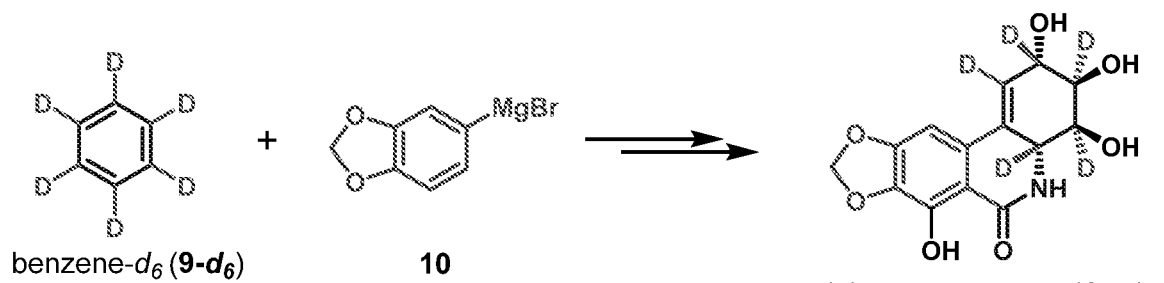
benzene-$d_6$ (9-$d_6$)    10
(+)-narciclasine-$d_5$ (4-$d_5$)
A549: 0.066 ± 0.001 µM
HCT116: 0.043 ± 0.002 µM
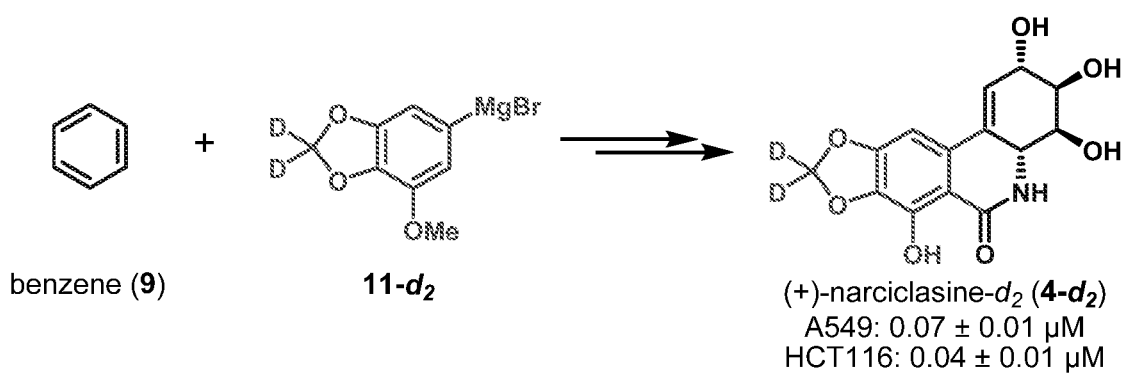
benzene (9)    11-$d_2$
(+)-narciclasine-$d_2$ (4-$d_2$)
A549: 0.07 ± 0.01 µM
HCT116: 0.04 ± 0.01 µM
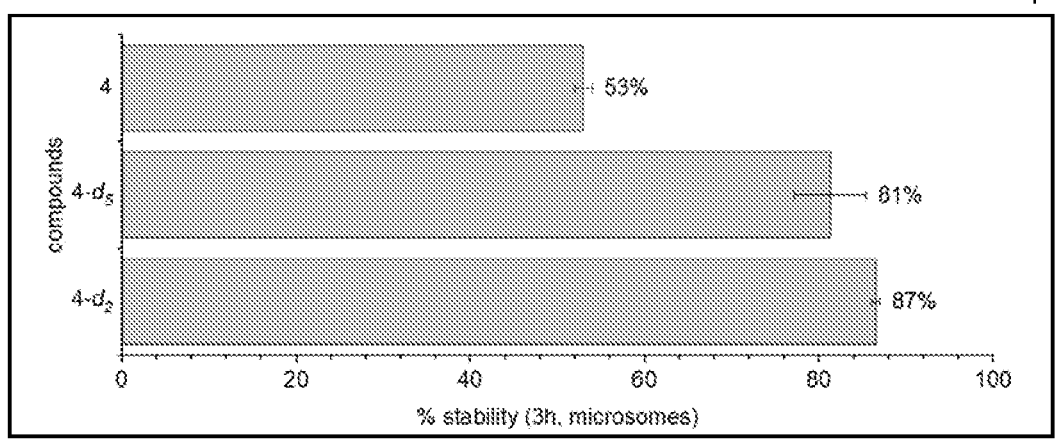
*(cont.)*

ISOCARBOSTYRIL ALKALOIDS AND FUNCTIONALIZATION THEREOF

RELATED APPLICATIONS

This application is a National Stage filing under 35 U.S.C. § 371 of International Application No. PCT/US2019/064388 filed Dec. 4, 2019, which claims priority under 35 U.S.C. § 119(e) to U.S. Provisional Patent Application No. 62/775,521 filed Dec. 5, 2018, which applications are incorporated herein by reference.

GOVERNMENT SUPPORT

This invention was made with government support under Grant No. GM122891 awarded by the National Institutes of Health. The government has certain rights in the invention.

BACKGROUND OF THE INVENTION

Plants belonging to the Amaryllidaceae family have long been known for their medicinal properties; their importance was recognized by the Ancient Greeks, as crude plant extracts were prescribed by Hippocrates and his School of Medicine as remedies against various illnesses, including tumors. Isolation studies revealed numerous compounds associated with the significant anticancer effects of these plants, including the isocarbostyril-type alkaloids (+)-7-deoxypancratistatin (1), (+)-pancratistatin (2), (+)-lycoricidine (3), and (+)-narciclasine (4) (Scheme 1). These compounds exhibited significant growth-inhibitory potencies against several human cancer cell lines and showed unique cytotoxicity patterns that do not correlate with any known anticancer agents. For example, experiments examining the cytotoxic profile of these compounds revealed noticeably reduced death in non-cancerous cells relative to cancer cells, suggesting that their development as chemotherapeutics could result in fewer adverse side-effects. Moreover, narciclasine (4) exhibited considerable activity in in vivo tumor models, including highly invasive human glioblastomas and apoptosis-resistant brain metastases, albeit with toxicity also being reported in certain cases. In addition to their potent anticancer activity, pancratistatin (2) and 7-deoxypancratistatin (1) also showed significant antiviral activity, such as in in vivo models for Japanese encephalitis, and narciclasine (4) has been found to attenuate diet-induced obesity and to possess anti-inflammatory properties.

Despite these encouraging biological properties, the precise biomolecular mechanisms of action have not been fully elucidated. Pancratistatin is believed to induce apoptosis through the intrinsic pathway, as evidenced by an increase in caspase-9 and caspase-3 activity, exposure of phosphatidyl serine, and destabilization of mitochondrial membrane potential. Interestingly, the cytotoxic activity of narciclasine has been attributed to the extrinsic caspase-8 apoptotic pathway via the activation of the Fas and death receptor 4 (DR4) death inducing signaling complex (DISC). Furthermore, narciclasine has exhibited activity in cytostatic pathways that complement its cytotoxic ones. It has been shown to block peptide synthesis through direct inhibition of the A-site of the 60S ribosome. These findings were further corroborated by co-crystallization of narciclasine (4) in the A-site of the 60S ribosome. Additionally, 4 binds the translation elongation factor eEF1A, thereby impeding this protein's secondary function of actin bundle formation and disrupting polysome organization and impairing cytokinesis. Likewise, similar activities are observed through the activation of GTPase RhoA in glioblastoma cells, causing the formation of F-actin stress fibers that disrupt cytokinesis.

Scheme 1. Structures of isocarbostyril alkaloids (+)-7-deoxypancratistatin (1), and (+)-pancratistatin (2) (+)-lycoricidine (3), (+)-narciclasine (4).

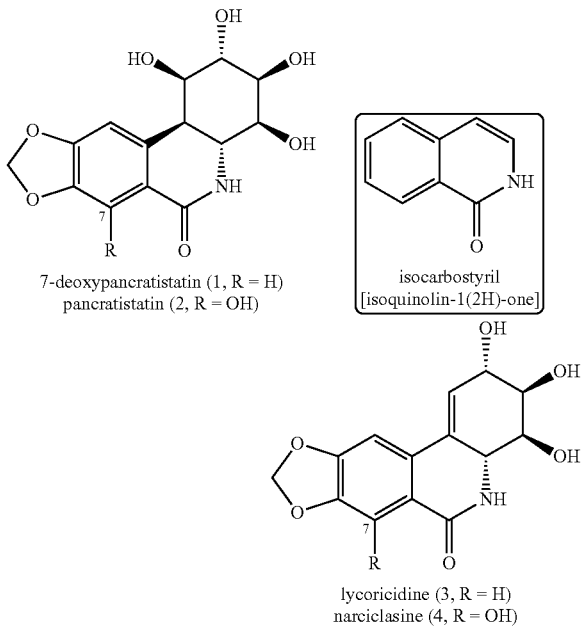

These promising biological attributes sparked significant interest for large-scale production of isocarbostyrils 1-4 to enable preclinical evaluations. To this end, the highest yielding isolation of (+)-pancratistatin (2), from 100 kg of *Hymenocallis litoralis* grown in the Hawaiian wilderness, yielded 15 g (150 mg/kg, 0.015% yield) of 2. To secure more sustainable access, a biotechnological approach was developed involving a plant tissue culture cloning of the same plant species. Unfortunately, cultivation of these plants in fields and greenhouses in Arizona delivered only 9-24 mg/kg (0.0009-0.0024%) of pure material. On the other hand, various isolation protocols for narciclasine have been reported in the literature, yielding 30-140 mg/kg of natural product from wet *Narcissus* plant bulbs.

Due to the challenging isolation from natural sources, the isocarbostyrils 1-4 have been exceptionally attractive targets for chemical synthesis, with nearly fifty distinct strategies reported to date. Despite many elegant approaches, the discovery of a sustainable route with practical access to these natural products has remained elusive, as nearly all biological evaluations of 1-4 have been conducted using isolated natural material. Nevertheless, these impressive synthetic endeavors enabled basic SAR studies that identified the core pharmacophore and provided more potent and selective analogs that could not be accessed through direct modification of the natural products.

Considering the lack of scalable approaches, we initially became interested in the synthesis of (+)-pancratistatins (1 and 2). However, it was apparent at the outset of this work that the newly developed methodology, which was needed to streamline this task, would also create opportunities to explore the synthesis of (+)-lycoricidine, (+)-narciclasine, and tailored analogs thereof.

The problem is there is a lack of synthetic methods that can quickly afford analogs of pancratistatin and its relatives.

Accordingly, there is a need for easily accessible intermediates of pancratistatin that can be derivatized at positions where structure activity relationships are unexplored, in an effort to find new therapeutics.

SUMMARY

Herein, we describe our synthetic approaches to isocarbostyrils 1-4, and several designed analogs with improved physiochemical properties and metabolic stability. This work ultimately resulted in an interesting methodological development and led to an efficient and scalable synthesis of these intriguing alkaloids.

Accordingly, this disclosure provides an alkaloid compound of Formula I:

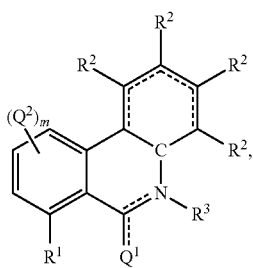

(I)

or a deuterium isotope thereof;
wherein
C is an sp$^3$ carbon atom;
═ is a single bond, or an optional double bond wherein two adjacent ═ do not form consecutive double bonds;
$Q^1$ is $NR^yR^z$, $OR^y$, or $SR^y$, wherein $R^z$ is H or —(C$_1$-C$_6$)alkyl, and $R^y$ is H, —(C$_1$-C$_6$)alkyl, or absent when ═ on $Q^1$ is a double bond;
each $Q^2$ is independently halo, —(C$_1$-C$_6$)alkyl, $N(R^a)_2$, $OR^a$, $SR^a$, wherein each $R^a$ is independently H or —(C$_1$-C$_6$)alkyl, or two adjacent $Q^2$ optionally taken together form a ring;
m is 0-3;
$R^1$ is halo, —(C$_1$-C$_6$)alkyl, —(C$_3$-C$_6$)cycloalkyl, $SR^b$, —C(═O)$R^c$, —S(═O)$_2R^c$, cyano, nitro, phenyl, $N(R^b)_2$, or a nitrogen heterocycle; or $R^1$ and $Q^1$ taken together form a 5- or 6-membered ring;
wherein
each $R^b$ is independently H, —(C$_1$-C$_6$)alkyl, —C(═O)$R^c$, or optionally two $R^b$ taken together form a heterocycle when $R^1$ is $N(R^b)_2$; and
$R^c$ is H, OH, —(C$_1$-C$_6$)alkyl, —O(C$_1$-C$_6$)alkyl, $N(R^d)_2$, or phenyl, wherein each $R^d$ is independently H or —(C$_1$-C$_6$)alkyl; and
each $R^2$ is independently H, halo, or $OR^e$ wherein each $R^e$ is independently H, —(C$_1$-C$_6$)alkyl, or a protecting group, or two adjacent $R^2$ taken together optionally form an epoxide, or an alkylenedioxy group;
$R^3$ is H, —(C$_1$-C$_6$)alkyl, or —C(═O)$R^e$; and
wherein each —(C$_1$-C$_6$)alkyl, —(C$_3$-C$_6$)cycloalkyl, phenyl and heterocycle are optionally substituted with or one or more substituents, each —(C$_1$-C$_6$) alkyl and —(C$_3$-C$_6$)cycloalkyl is saturated or optionally unsaturated, and each —(C$_1$-C$_6$)alkyl is unbranched or optionally branched; wherein any H on the molecule can optionally be D (deuterium).

This disclosure also provides a method of making an alkaloid compound of Formula VII:

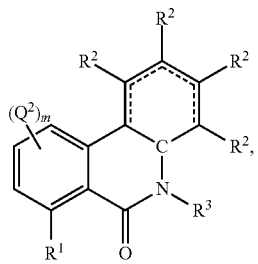

(VII)

or a deuterium isotope thereof;
wherein
C is an sp$^3$ carbon atom;
═ is a single bond, or an optional double bond wherein two adjacent ═ do not form consecutive double bonds;
each $Q^2$ is independently halo, —(C$_1$-C$_6$)alkyl, $N(R^a)_2$, $OR^a$, $SR^a$, wherein each $R^a$ is independently H or —(C$_1$-C$_6$)alkyl, or two adjacent $Q^2$ optionally taken together form a ring;
m is 0-3;
$R^1$ is halo, —(C$_1$-C$_6$)alkyl, —(C$_3$-C$_6$)cycloalkyl, $OR^b$, $SR^b$, —C(═O)$R^c$, —S(═O)$_2R^c$, cyano, nitro, phenyl, $N(R^b)_2$, or a nitrogen heterocycle;
wherein
each $R^b$ is independently H, —(C$_1$-C$_6$)alkyl, —C(═O)$R^c$, or optionally two $R^b$ taken together form a heterocycle when $R^1$ is $N(R^b)_2$; and
$R^c$ is H, OH, —(C$_1$-C$_6$)alkyl, —O(C$_1$-C$_6$)alkyl, $N(R^d)_2$, or phenyl, wherein each $R^d$ is independently H or —(C$_1$-C$_6$)alkyl; and
each $R^2$ is independently H, halo, or $OR^e$ wherein each $R^e$ is independently H, —(C$_1$-C$_6$)alkyl, or a protecting group, or two adjacent $R^2$ taken together optionally form an epoxide, or an alkylenedioxy group;
$R^3$ is H, —(C$_1$-C$_6$)alkyl, or —C(═O)$R^e$; and
wherein each —(C$_1$-C$_6$)alkyl, —(C$_3$-C$_6$)cycloalkyl, phenyl and heterocycle are optionally substituted with or one or more substituents, each —(C$_1$-C$_6$) alkyl and —(C$_3$-C$_6$)cycloalkyl is saturated or optionally unsaturated, and each —(C$_1$-C$_6$)alkyl is unbranched or optionally branched;
comprising:
a) contacting a compound of Formula VIIB:

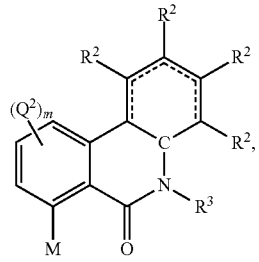

(VIIB)

or a deuterium isotope thereof;
wherein M is H; and
$R^2$, $R^3$, $Q^2$ and m are as defined for Formula VII;
and an organometallic regent to form an organometallic compound of Formula VIIB wherein M is a metal of the organometallic reagent; and
b) quenching the organometallic compound with an electrophile, thereby forming the alkaloid compound of Formula VII; wherein any H on the molecule can optionally be D (deuterium).

The invention provides novel compounds of Formulas I-VII, intermediates for the synthesis of compounds of Formulas I-VII, as well as methods of preparing compounds of Formulas I-VII. The invention also provides compounds of Formulas I-VII that are useful as intermediates for the synthesis of other useful compounds. The invention provides for the use of compounds of Formulas I-VII for the manufacture of medicaments useful for the treatment of bacterial infections in a subject, such as a human.

The invention provides for the use of the compositions described herein for use in medical therapy. The medical therapy can be treating cancer, for example, breast cancer, lung cancer, pancreatic cancer, prostate cancer, or colon cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1. (a) Anticancer activity of C-7 analogs of lycoricidine. (b) Role of C-7 amine substituent on solubility. High throughput equilibrium solubility using miniaturized shake flask approach was used. Error is SEM, n≥3. (c) Evaluation of metabolic stability of narciclasine (3) and its deuterated isotopologs (4-$d_5$ and 4-$d_2$). Stability was assessed in mouse liver microsomes. Compounds were incubated with microsomes for 3h, and the percentage remaining was quantified relative to $t_0$ using an internal standard. Error is SEM, n≥2.

DETAILED DESCRIPTION

The Amaryllidaceae isocarbostyril alkaloids have been inspiring the synthetic community for many decades, serving as benchmark molecules for the showcase of many creative approaches towards their unique molecular architectures and stereochemical complexity. The syntheses of isocarbostyril alkaloids (+)-7-deoxypancratistatin (1), (+)-pancratistatin (2), lycoricidine (3) and narciclasine (4) described herein utilize a new methodology and strategy, developed specifically for their highly decorated aminocyclitol core. The key asymmetric dearomative trans-1,2-carboamination of benzene (9) provided facile access to these natural products through diene intermediate 7, which served as a divergence point for the synthesis of 1-4. Moreover, late-stage C-7 cupration of (+)-7-deoxypancratistatins (1) and lycoricidine (3) provided direct synthetic connection to (+)-pancratistatin (2) and narciclasine (4) in a practical, single operation.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, D, F, or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C═O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, 1-4 carbon atoms, or a range in between, for example, 2-6 carbon atoms or 3-6 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4- oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof. Such as racemic mixtures, form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "$sp^3$ hybridization" or "$C(sp^3)$" means that an atom is bonded and/or coordinated in a configuration having a tetrahedral character of at least 50%. For tetracoordinate boron atoms, the tetrahedral character of the boron atom is calculated by the method of Hopfl, H., *J Organomet. Chem.* 581, 129-149, 1999.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone or two or more of them may be mixed for use to provide a "solvent system".

The term "electrophile" refers to a reagent attracted to electrons. Electrophiles are positively charged or neutral species having vacant orbitals that are attracted to an electron rich center. It participates in a chemical reaction by accepting an electron pair in order to bond to a nucleophile, such as a carbanion or an organometallic reagent (e.g. a cuprate or an organocopper compound. See Gary H. Posner, *An introduction to synthesis using organocopper reagents*, Wiley, New York, 1980). Because electrophiles accept electrons, they are Lewis acids. Most electrophiles are positively charged, have an atom that carries a partial positive charge, or have an atom that does not have an octet of electrons. They appear to attract electrons as well and seem to behave as though they are partially empty. These partially empty substances thus require an electron rich center, and thus they are filled.

Embodiments of the Invention

This disclosure provides an alkaloid compound of Formula I.

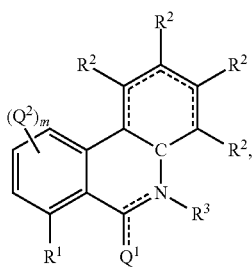

(I)

or a deuterium isotope thereof;
wherein
C is an sp$^3$ carbon atom;
═══ is a single bond, or an optional double bond wherein two adjacent ═══ do not form consecutive double bonds;
$Q^1$ is $NR^yR^z$, $OR^y$, or $SR^y$, wherein $R^z$ is H or —($C_1$-$C_6$)alkyl, and $R^y$ is H, —($C_1$-$C_6$)alkyl, or absent when ═══ on $Q^1$ is a double bond;
each $Q^2$ is independently halo, —($C_1$-$C_6$)alkyl, $N(R^a)_2$, $OR^a$, $SR^a$, wherein each $R^a$ is independently H or —($C_1$-$C_6$)alkyl, or two adjacent $Q^2$ optionally taken together form a ring;
m is 0-3;
$R^1$ is halo, —($C_1$-$C_6$)alkyl, —($C_3$-$C_6$)cycloalkyl, $SR^b$, —C(═O)$R^c$, —S(═O)$_2R^c$, cyano, nitro, phenyl, $N(R^b)_2$, or a nitrogen heterocycle; or $R^1$ and $Q^1$ taken together form a 5- or 6-membered ring;
wherein
each $R^b$ is independently H, —($C_1$-$C_6$)alkyl, —C(═O)$R^c$, or optionally two $R^b$ taken together form a heterocycle when $R^1$ is $N(R^b)_2$; and $R^c$ is H, OH, —($C_1$-$C_6$)alkyl, —O($C_1$-$C_6$)alkyl, $N(R^d)_2$, or phenyl, wherein each $R^d$ is independently H or —($C_1$-$C_6$)alkyl; and
each $R^2$ is independently H, halo, or $OR^e$ wherein each $R^e$ is independently H, —($C_1$-$C_6$)alkyl, or a protecting group, or two adjacent $R^2$ taken together optionally form an epoxide, or an alkylenedioxy group;
$R^3$ is H, —($C_1$-$C_6$)alkyl, or —C(═O)R; and
wherein each —($C_1$-$C_6$)alkyl, —($C_3$-$C_6$)cycloalkyl, phenyl and heterocycle are optionally substituted with or one or more substituents, each —($C_1$-$C_6$) alkyl and —($C_3$-$C_6$)cycloalkyl is saturated or optionally unsaturated, and each —($C_1$-$C_6$)alkyl is unbranched or optionally branched; wherein any H on the molecule is optionally D (deuterium).

In various embodiments, the hydrogen atoms of the disclosed compounds can be replaced by one or more deuterium atoms, for example by synthesizing the disclosed compounds from commercially available deuterated starting materials. In various other embodiments, the disclosed compounds (drawn in 2-dimensions) can be any stereoisomer having an (R)- or (S)-configuration at each stereocenter, as a purified compound or a mixture of stereoisomers.

In some embodiments, $Q^1$ is $OR^y$ and $Q^2$ is $OR^a$, or two adjacent $Q^2$ taken together form an alkylenedioxy group. In other embodiments, two adjacent $Q^2$ taken together form a ring such as, but not limited to a methylene dioxy group, an acetal, a ketal, a cyclohexyl, a cyclopentyl, a heterocycle, an aryl, or a heteroaryl. In additional embodiments, the said formed rings from two adjacent $Q^2$ can be optionally substituted, for example, with a hydrogen bond donor or acceptor, or can comprise a hydrogen bond donor or acceptor.

In yet other additional embodiments, two $R^b$ taken together form a heterocycle when $R^1$ is $N(R^b)_2$, wherein the heterocycle is optionally substituted, for example, with a hydrogen bond donor or acceptor, or the formed heterocycle can comprise a hydrogen bond donor or acceptor. In general, a substituent at $R^1$, such as a nitrogen heterocycle, can be further substituted, for example with a hydrogen bond donor or acceptor, or the nitrogen heterocycle can comprise a hydrogen bond donor or acceptor.

In further embodiments, $R^1$ and an adjacent $Q^2$ taken together form a 5- or 6-membered ring wherein the 5- or 6-membered ring is optionally substituted, for example, with a hydrogen bond donor or acceptor, or the formed ring can comprise a hydrogen bond donor or acceptor.

In other various embodiments, $R^1$ of any of the disclosed compounds is —CH$_2$CH═CH$_2$, —C(═O)Ph, —CH$_2$OCH$_3$, —CH$_2$OH, —C(═O)OH, —C(═O)OCH$_3$, —CH$_2$C(═O)OH, —CH$_2$C(═O)OCH$_2$CH$_3$, —CN, —NH$_2$, —NHCH$_3$, —NHC(═O)CH$_3$, —N-pyrrolidine, or —N-morpholine.

In some other embodiments, $R^1$ and $Q^1$ taken together form a 5- or 6-membered ring, wherein the 5- or 6-membered ring is substituted, for example with a hydrogen bond donor or acceptor, or the 5- or 6-membered ring comprises a hydrogen bond donor or acceptor.

In some other embodiments, $Q^1$ is O, ═══ is a double bond on $Q^1$, and two adjacent $Q^2$ taken together form a methylenedioxy group. In further embodiments, each $R^2$ is independently H, OH, OCF$_3$, OCF$_2$CF$_3$, or comprises the moiety —OSi($C_1$-$C_8$)alkyl.

In additional embodiments, the compound of Formula I is a compound of Formula II:

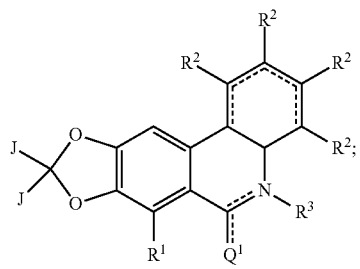
(II)

wherein each J is independently H, D, or CH$_3$. In other embodiments, J can also be CD$_3$.

In other additional embodiments, the compound of Formula II is a compound of Formula IIA or IIB:

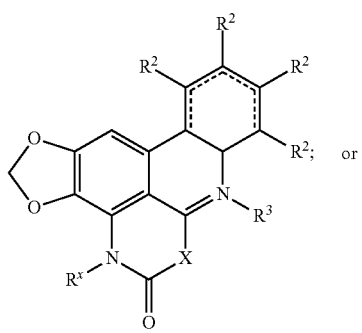
(IIA)

or (IIB)

wherein X is O or NR$^x$, and R$^x$ is H or —(C$_1$-C$_6$)alkyl.

In further embodiments, the compound of Formula II is a compound of Formula III:

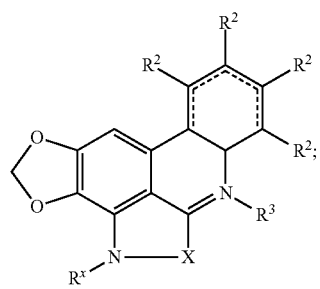
(III)

In yet other embodiments, the compound of Formula I is a compound of Formula IV:

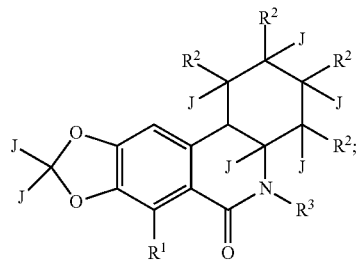
(IV)

wherein each J is independently H or D. In some embodiments, J of the dioxolane ring are D; in further embodiments, one or more J on the six-membered ring having J substituents on Formula IV are D.

In various embodiments, R$^1$ is cyano or N(R$^b$)$_2$. In other various embodiments, each R$^2$ is independently H or OH.

In yet other embodiments, the compound of Formula IV is a compound of Formula IVA:

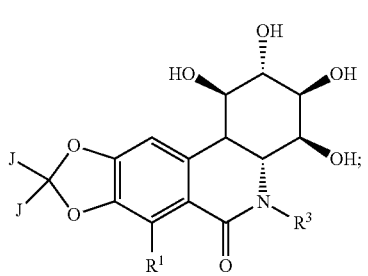
(IVA)

or the enantiomer or diastereoisomers thereof.

In various additional embodiments, R$^1$ is cyano or NH$_2$, and J and R$^3$ are H. In other embodiments, J is D. In further embodiments, R$^1$ is —CH$_2$CH=CH$_2$, —C(=O)Ph, —CH$_2$OCH$_3$, —CH$_2$OH, —C(=O)OH, —C(=O)OCH$_3$, —CH$_2$C(=O)OH, —CH$_2$C(=O)OCH$_2$CH$_3$, —CN, —NH$_2$, —NHCH$_3$, —NHC(=O)CH$_3$, —N-pyrrolidine, or —N-morpholine.

In other embodiments, the compound of Formula I is a compound of Formula VA, VB, or VC:

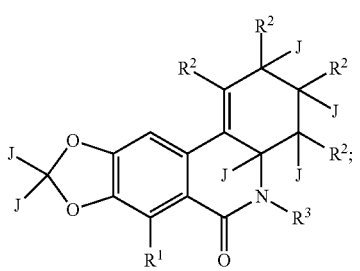
(VA)

-continued

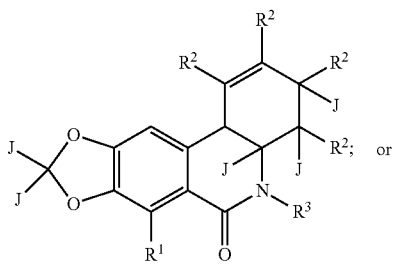
(VB)

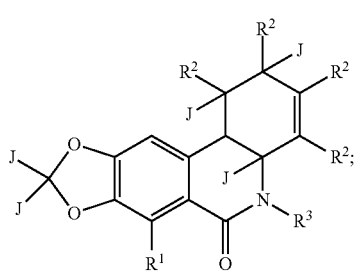
(VC)

wherein each J is independently H or D.

In other embodiments, one or more J is D. In further embodiments, $R^1$ is —CH$_2$CH=CH$_2$, —C(=O)Ph, —CH$_2$OCH$_3$, —CH$_2$OH, —C(=O)OH, —C(=O)OCH$_3$, —CH$_2$C(=O)OH, —CH$_2$C(=O)OCH$_2$CH$_3$, —CN, —NH$_2$, —NHCH$_3$, —NHC(=O)CH$_3$, —N-pyrrolidine, or —N-morpholine. In various other embodiments, $R^1$ is cyano or N($R^b$)$_2$. In additional various embodiments, each $R^2$ is independently H or OH, and J and $R^3$ are H.

In some other embodiments, the compound of Formula VA is a compound of Formula VI:

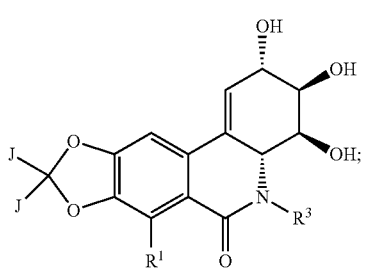
(VI)

or the enantiomer thereof.

In further additional embodiments, $R^1$ is cyano or NH$_2$, and J and $R^3$ are H. In other embodiments, J is D. In yet other embodiments, $R^1$ is —CH$_2$CH=CH$_2$, —C(=O)Ph, —CH$_2$OCH$_3$, —CH$_2$OH, —C(=O)OH, —C(=O)OCH$_3$, —CH$_2$C(=O)OH, —CH$_2$C(=O)OCH$_2$CH$_3$, —CN, —NH$_2$, —NHCH$_3$, —NHC(=O)CH$_3$, —N-pyrrolidine, or —N-morpholine.

Additionally, this disclosure provides a method of making an alkaloid compound of Formula VII:

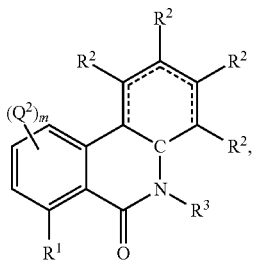
(VII)

or a deuterium isotope thereof;
wherein
C is an sp$^3$ carbon atom;
=== is a single bond, or an optional double bond wherein two adjacent === do not form consecutive double bonds;
each $Q^2$ is independently halo, —(C$_1$-C$_6$)alkyl, N($R^a$)$_2$, O$R^a$, S$R^a$, wherein each $R^a$ is independently H or —(C$_1$-C$_6$)alkyl, or two adjacent $Q^2$ optionally taken together form a ring;
m is 0-3;
$R^1$ is halo, —(C$_1$-C$_6$)alkyl, —(C$_3$-C$_6$)cycloalkyl, O$R^b$, S$R^b$, —C(=O)$R^c$, —S(=O)$_2R^c$, cyano, nitro, phenyl, N($R^b$)$_2$, or a nitrogen heterocycle;
wherein
each $R^b$ is independently H, —(C$_1$-C$_6$)alkyl, —C(=O)$R^c$, or optionally two $R^b$ taken together form a heterocycle when $R^1$ is N($R^b$)$_2$; and
$R^c$ is H, OH, —(C$_1$-C$_6$)alkyl, —O(C$_1$-C$_6$)alkyl, N($R^d$)$_2$, or phenyl, wherein each $R^d$ is independently H or —(C$_1$-C$_6$)alkyl; and
each $R^2$ is independently H, halo, or O$R^e$ wherein each $R^e$ is independently H, —(C$_1$-C$_6$)alkyl, or a protecting group, or two adjacent $R^2$ taken together optionally form an epoxide, or an alkylenedioxy group;
$R^3$ is H, —(C$_1$-C$_6$)alkyl, or —C(=O)$R^c$; and
wherein each —(C$_1$-C$_6$)alkyl, —(C$_3$-C$_6$)cycloalkyl, phenyl and heterocycle are optionally substituted with or one or more substituents, each —(C$_1$-C$_6$)alkyl and —(C$_3$-C$_6$)cycloalkyl is saturated or optionally unsaturated, and each —(C$_1$-C$_6$)alkyl is unbranched or optionally branched;
comprising:
a) contacting a compound of Formula VIIB:

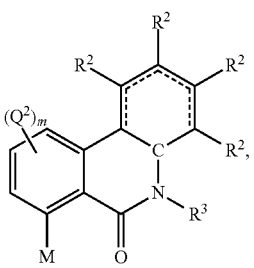
(VIIB)

or a deuterium isotope thereof;
    wherein M is H; and
    $R^2$, $R^3$, $Q^2$ and m are as defined for Formula VII;
and an organometallic regent to form an organometallic compound of Formula VIIB wherein M is a metal of the organometallic reagent; and
    b) quenching the organometallic compound with an electrophile, wherein the organometallic compound is formed by directed metalation, and the electrophile replaces the metal of the organometallic compound, thereby forming the alkaloid compound of Formula VII.

In additional embodiments, the electrophile can be, for example but is not limited to a peroxide, an alkyl halide, an acyl halide or a hydroxylamine. In various embodiments, the organometallic reagent is a cuprate or an organocopper compound. In additional embodiments, M of the organometallic compound of Formula VIIB comprises copper. In various additional embodiments, an electrophile that can react with the organometallic compound of Formula VIIB (e.g., a copper compound of Formula VIIB) is any alkyl or acyl halide of type R—X or R—COX, wherein R is alkyl, vinyl, alkynyl, aryl or heteroaryl; and X is any halogen (F, Cl, Br, I). Additionally, the organometallic compound (copper compound) can react with hydroxylamine derivatives (of the type NR'R"—OR'"), wherein R', R" and R'" are H independently an alkyl, aryl or heteroaryl.

In other various embodiments, the carbon atom of the $C(sp^3)$-N moiety has an (R)-configuration. In various other embodiments, the carbon atom of the $C(sp^3)$-N moiety has an (S)-configuration.

Results and Discussion

Olefin-like Functionalization of Benzene. The ultimate synthetic challenge posed by isocarbostyrils 1-4 is the construction of the densely-decorated aminocyclitol cores containing six or four contiguous stereocenters. We postulated that these motifs could be traced back to benzene using distinct alkene difunctionalization reactions, which would ideally set all the required functionality of pancratistatins (1 and 2), as well as lycoricidine (3) and narciclasine (4) in a stereoselective manner (Scheme 2). Based on their substitution pattern, the pancratistatins could be derived from aminotetraols 5 or 6. These hexafunctionalized cyclohexanes could be traced back to the corresponding dienes 7 and 8 by applying two different dihydroxylations. Finally, we hypothesized that dienes of this type could be obtained from benzene (9) through dearomative trans-1,2-carboamination with N-methyl-1,2,4-triazoline-3,5-dione (MTAD, 12) and aryl Grignard reagents 10 or 11. Using similar yet distinct disconnections, lycoricidine (3) and narciclasine (4) could originate from the corresponding functionalized lactam precursors 13 and 14, which in turn, could be obtained from dienes 7 and 8.

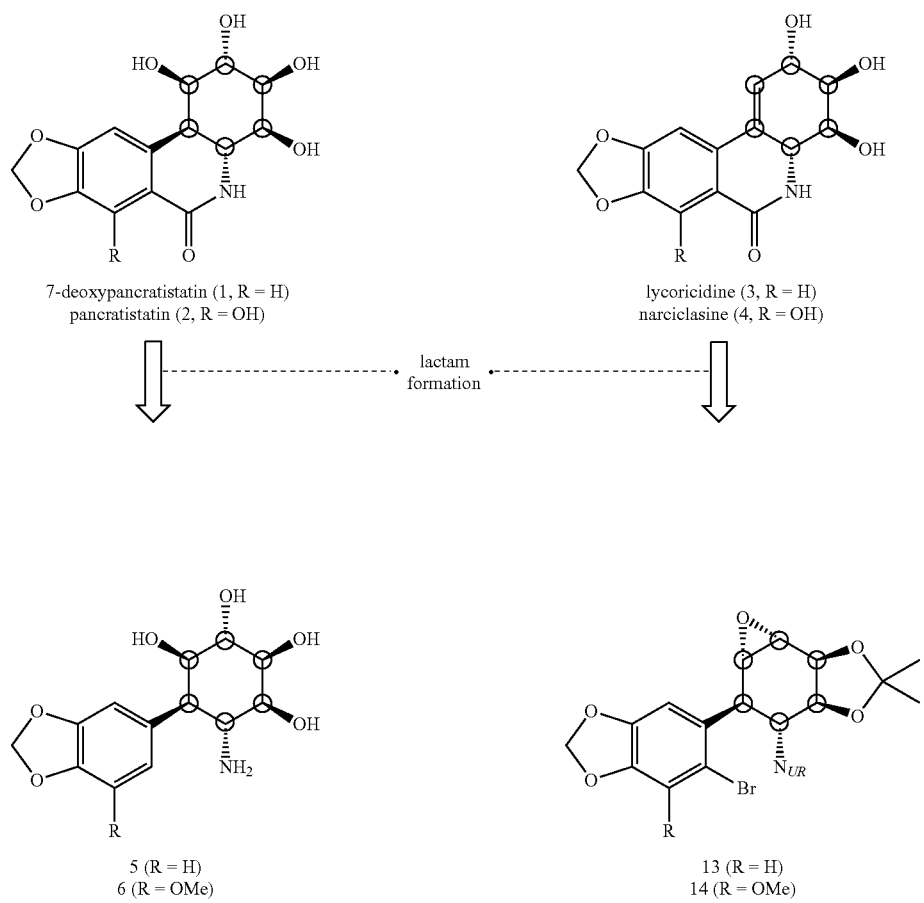

Scheme 2. Retrosynthetic analysis of isocarbostyril alkaloids 1-4 from benzene (9) using an olefin-functionalization approach 7-deoxypancratistatin (1, R = H)
pancratistatin (2, R = OH)

lycoricidine (3, R = H)
narciclasine (4, R = OH)

lactam formation 5 (R = H)
6 (R = OMe)

13 (R = H)
14 (R = OMe)

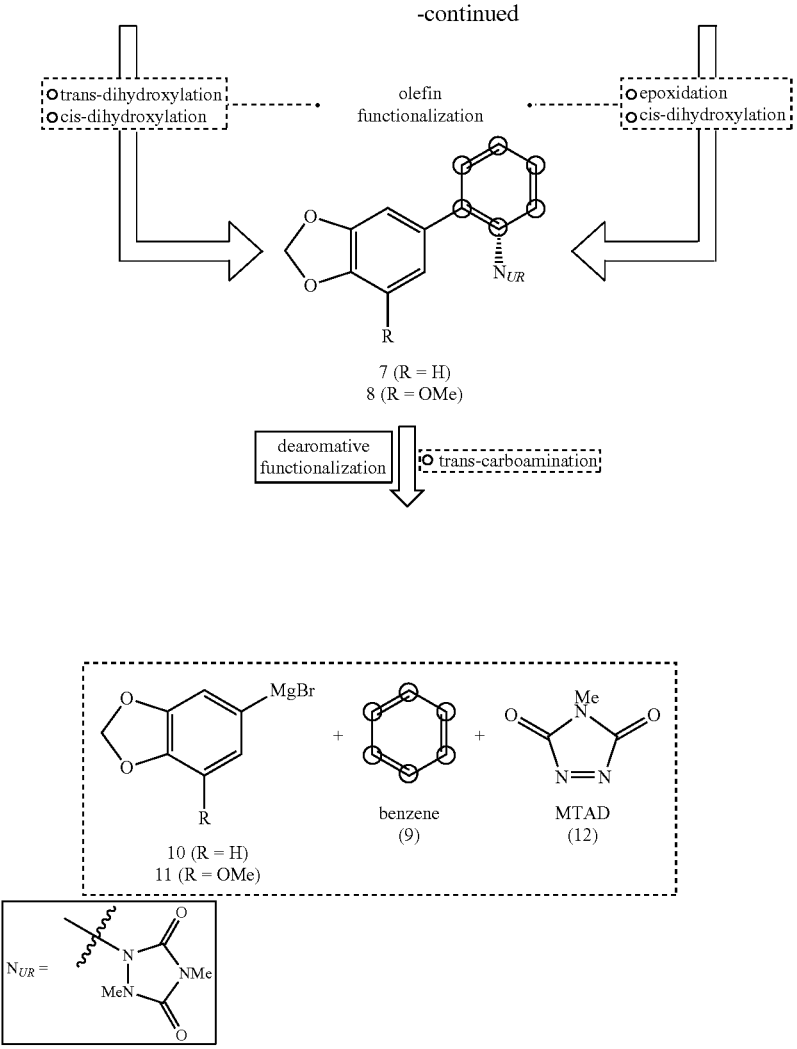

Based on the above retrosynthetic analysis, benzene (9) could be considered as a surrogate for the hypothetical 1,3,5-cyclohexatriene; thus, three olefin-type difunctionalization reactions would enable the key retrosynthetic disconnections and provide natural products 1-4 in a rapid and controlled fashion. However, due to the inherent resonance stabilization of benzene, these and related olefin-like dearomative transformations are practically non-existent in synthetic organic chemistry. Only certain stoichiometric reactions of transition-metal complexes and microbial arene oxidation can affect olefin-like dearomative functionalizations; however, such processes are not suitable for the desymmetrization of benzene.

Dearomative trans-1,2-Carboamination. At the onset of our studies, it was clear that invention of a novel dearomatization process was crucial to the success of our synthetic plan. Since our laboratory has been involved in the development of dearomative functionalizations based on visible-light-promoted para-cycloaddition with arenophiles, we postulated that the application of this chemistry in the presence of a transition metal catalyst and an aryl nucleophile could result in the desired trans-1,2-carboamination (Scheme 3a). Particularly, we were keen to explore if the intermediate arenophile MTAD-benzene cycloadduct 15 could serve as a viable substrate for oxidative addition with low-valent transition metals, as it possesses an electron-deficient bis-allylic bridgehead urazole. We envisioned that a diene of type 15 could serve as a π-ligand, coordinating to the metal center and facilitating oxidative addition in an anti-fashion to the urazole moiety (15→I). This step would lead to cyclohexadienyl intermediate II, which could undergo transmetalation with an organometallic reagent to form $\eta^5$-species III. Finally, reductive elimination (III→IV) and diene decomplexation would yield the product 16 and regenerate the metal catalyst.

Though catalysis involving $\eta^5$-species had not been previously reported, our studies were inspired by the wealth of chemistry employing stoichiometric reactions of $\eta^5$-complexes. Early work from Birch, and later findings from Pearson, Davies, Green, and Mingos, showcased highly regio- and stereoselective outcomes in cationic cyclohexadienylmetal complexes with nucleophiles (Scheme 3b). For example, the most widely-studied iron $\eta^5$-intermediate 19, prepared from the corresponding 1,3-diene via complexation (17→18) and subsequent C—H abstraction (18→19), reacts with nucleophiles with exclusive 1,2-site-selectivity (19→20), due to the greater positive charge localized on the termini of the $\eta^5$-system.

Scheme 3
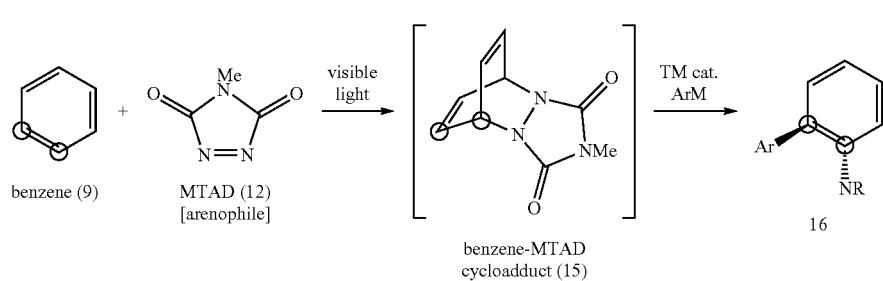
benzene (9) + MTAD (12) [arenophile] → benzene-MTAD cycloadduct (15) → 16
mechanistic rationale:
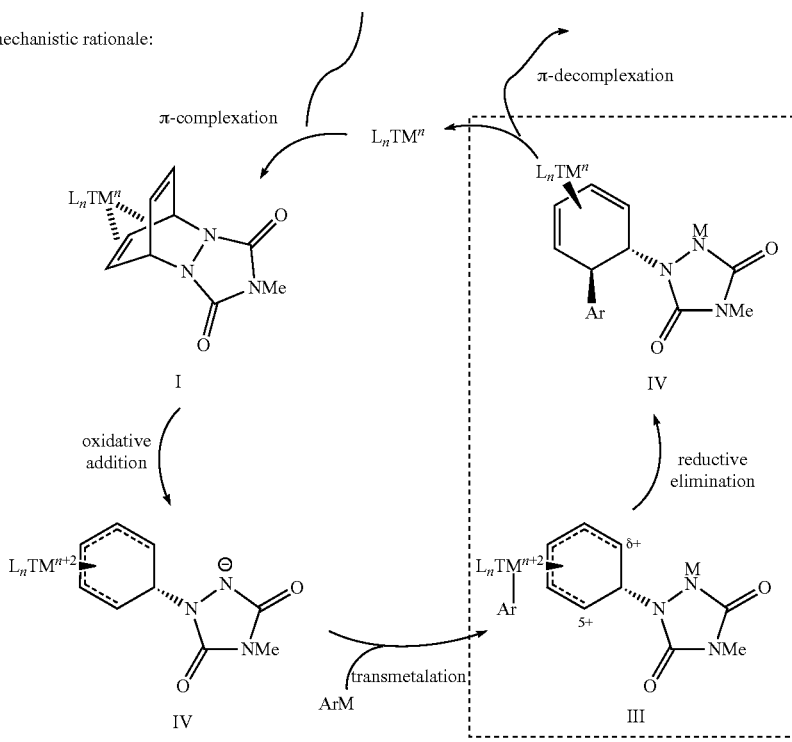
b) chemistry of cyclohexadienyliron complexes
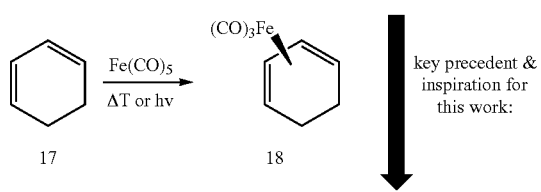
key precedent & inspiration for this work:

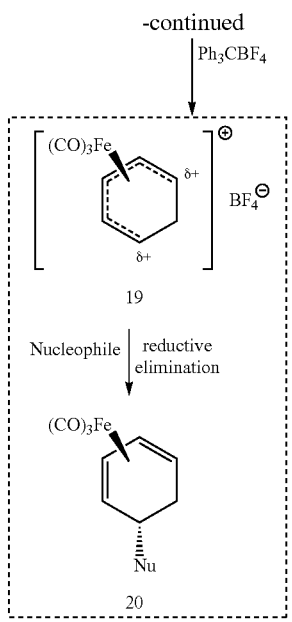
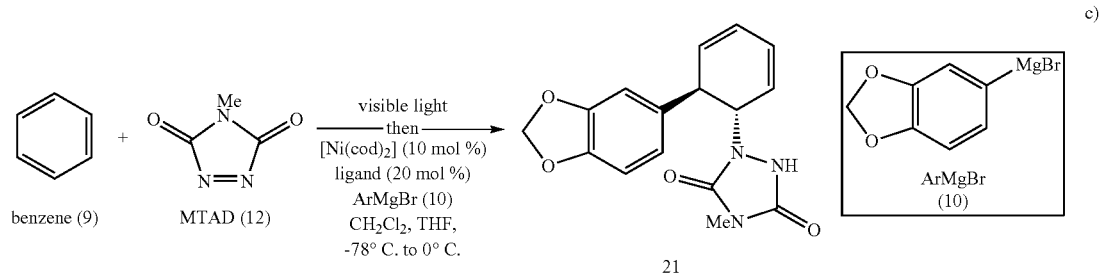
chiral P,P-ligands:
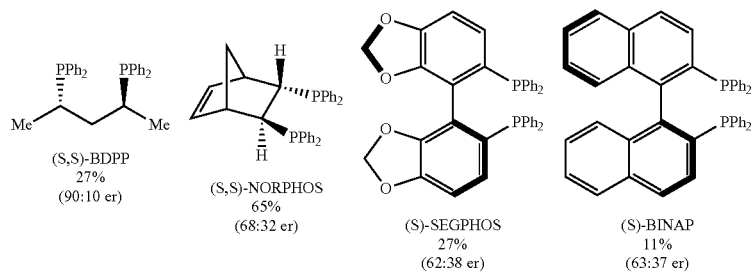
chiral P,N-ligands:
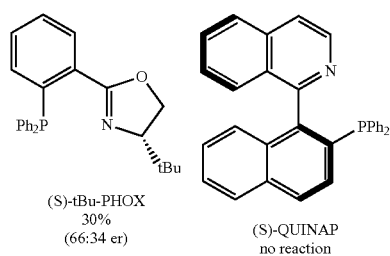

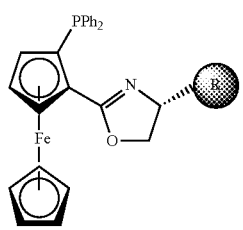

(R,R$_p$)-Phosferrox-type ligand

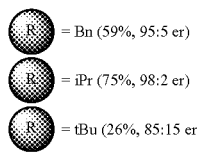
= Bn (59%, 95:5 er)
= iPr (75%, 98:2 er)
= tBu (26%, 85:15 er)

achiral P,P-ligands:

Ph$_2$P$\frown$PPh$_2$ dppe (n = 2): 55%
dppp (n =3): 24%
dppb (n = 4): 14%
dpppent (n = 5): 17%
dpphex (n = 6): 45%

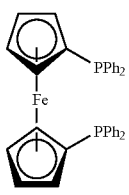
dppf: 74%

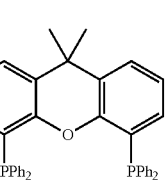
xanthphos: 21%

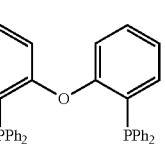
DPEPhos: 57% a) The concept and mechanistic rationale for dearomative trans-1,2-carboamiation strategy. b) A general reactivity of cyclohexadienyliron complexes with nucleophiles. c) Ligand scope for Ni-catalyzed dearomative trans-1,2-carboamination.

Encouraged by these precedents, we expected that symmetrical intermediate III should follow a similar mechanistic course to diene IV through an inner-sphere pathway, resulting in syn-delivery of a nucleophile relative to the metal center. Moreover, since the η$^5$-intermediate III is symmetrical, a reductive elimination step could enable enantiodiscrimination through differentiation of the enantiotopic termini of the cyclohexadienyl system. Thus, the desired product 16 could be formed in an enantioselective fashion by using a suitable chiral ligand bound to the metal center.

To probe the above-described reactivity of the arenophile-benzene cycloadduct with transition metals, we performed a series of prospecting investigations with aryl nucleophiles in combination with transition metals complexes. Catalysts based on Co, Ir, Rh, Cu, and Ni were primarily investigated as these metals have exceptionally rich repertoires of nucleophilic additions to their complexes containing allyl and dienyl ligands. Gratifyingly, by using the combination of [Ni(cod)$_2$] and phosphine ligands with organomagnesium bromide 10, we were able to observe the desired product (Scheme 3c). While monodentate phosphines and NHC-based ligands proved to be ineffective, most bisphosphines we tested furnished product 21, with dppf delivering the highest yield in this series. Specifically, we identified that conducting the MTAD-benzene cycloaddition reaction in dichloromethane, followed by the addition of a Ni-catalyst ([Ni(cod)$_2$]/dppf=10/20 mol %) and aryl Grignard reagent 10 delivered the desired dearomatized product 21 in 74% yield as a single diastereo- and constitutional isomer.

Although these experiments established the viability of a diastereoselective process, they did not address the feasibility of rendering the process enantioselective. Accordingly, we performed a comprehensive evaluation of chiral P,P- and P,N-bidentate ligands, and discovered that the PHOX-type ligand (R,R$_p$)-iPr-Phosferrox afforded the desired product 21 in 75% yield and with high enantioselectivity (98:2 er).

Initial Approaches to (+)-Pancratistatins. With the first vicinal stereocenters in place, the stage was set for the introduction of the remaining four hydroxy substituents in a stereoselective manner to complete the pancratistatin core (Scheme 4a). The initial plan involved formation of the trans-diol through hydrolytic opening of an epoxide, followed by Upjohn cis-dihydroxylation. However, early experiments with diene 21 and mCPBA or NBS/H$_2$O gave mixtures of products, likely due to the undesired directing effects of the urazole hydrazyl group (pK$_a$=5.8 in water). Therefore, methylation of the urazole's nitrogen proved crucial for stereo- and chemoselective diene functionalization. This effect is likely due to a more rigid conformation, where the methyl group shields the bottom face of the diene. Such a conformation was supported by NOESY experiments revealing through-space correlation between the methyl group and several diene protons (see inset at the bottom of Scheme 4). The methyl group was conveniently introduced (21→7) by simply adding Me$_2$SO$_4$ at the end of dearomatization sequence. Importantly, using a decreased catalyst loading ([Ni]/ligand=5/10 mol %), this one-pot process allowed us to routinely prepare decagram batches of diene 7.

With a robust sequence that allowed for the preparation of sufficient amounts of key diene 7, we turned our attention to the next two olefin difunctionalization steps. Due to the electron-withdrawing effect of the urazole nitrogen, it was expected that the alkene distal to this moiety should react preferentially with electrophilic reagents. Indeed, installation of the trans-diol by means of a two-step sequence involving epoxidation with mCPBA and subsequent epoxide hydrolysis (NaOBz, H$_2$O, 100° C.) proceeded smoothly, delivering product 22 as a single diastereo- and constitutional isomer (for X-ray of 22, see bottom of Scheme 4). The last alkene transformation needed for establishing the hexasubstituted aminocyclitol core was Upjohn dihydroxylation (Tetrahedron Lett. 1976, 17, 1973), which provided tetraol 23 in 910% yield.

The final sequence required to complete the synthesis of (+)-7-deoxypancratistatin (1) was the deprotection of urazole 23 to free amine 5 and its conversion to the corresponding lactam. Exploring known conditions to effect hydrolysis and N—N bond cleavage, such as heating in highly acidic or basic solutions followed by hydrogenolysis, led to complete decomposition of the starting material. Gratifyingly, we observed promising reactivity with hydride-based reducing agents. For example, exposure of urazole 23 to LiAlH$_4$ gave cyclic hydrazine hemiaminal 24 (Scheme 4, bottom); however, this compound readily underwent oxidation under an ambient atmosphere, complicating its isolation and reproducibility. Therefore, we developed a one-pot procedure that directly reduced this sensitive intermediate to amine 5 by carefully quenching the LiAlH$_4$ reduction with Rochelle's salt, followed by immediate addition of Raney-Co and exposure of the reaction mixture to a hydrogen atmosphere. Using this protocol, we consistently obtained free amine 5 in 60% yield on a multigram scale.

Additionally, we were able to secure amine 5 from diene 7 by an alternative pathway. Thus, subjecting diene 7 to NBS and H$_2$O gave bromohydrin 25 in 79% yield (for X-ray of 25, see bottom of Scheme 4). This intermediate underwent Upjohn dihydroxylation, and the resulting dibromotriol was subsequently exposed to weakly basic aqueous NaOBz to provide bromotetraol 26 through concomitant epoxide formation and hydrolysis. Similar, highly chemoselective hydrolytic opening of the corresponding intermediate epoxide diol was demonstrated by Hudlický during his approach to pancratistatins (J. Am. Chem. Soc. 1995, 117, 3643). Finally, the above-described sequential reduction with LiAlH$_4$ and Raney-Co furnished amine 5 through urazole fragmentation and protodehalogenation.

The ultimate objective, the construction of the lactam ring and completion of (+)-7-deoxypancratistatin (1), was initially achieved through Duff formylation (5→27) followed by Pinnick oxidation (27→1) (Tetrahedron Lett. 2009, 50, 3436). While formylation efficiently delivered the desired aldimine 27, separation of this product from HMTA and its byproducts proved challenging, and oxidation to 1 continuously gave inconsistent results. Therefore, an alternative pathway was sought that could still rely on the readily available hexafunctionalized precursor 5. Accordingly, we explored the Bischler-Napieralski reaction, as this key lactam forming strategy was successfully used by Banwell and others in similar molecular settings (J. Chem. Soc., Perkin Trans. 1, 1994, 3515). The corresponding isocyanate precursor 28 was readily prepared by sequential protection of amine with Boc and alcohols with acetates. The key cyclization was successfully accomplished with Hendrickson's reagent (triphenylphosphonium anhydride trifluoromethane sulfonate), delivering acetylated (+)-7-deoxypancratistatin that was converted to natural product 1 upon treatment with K$_2$CO$_3$ in MeOH.

With the synthesis of (+)-7-deoxypancratistatin (1) completed, we turned our attention to (+)-pancratistatin (2), expecting that the lessons learned from the synthesis of 1 could be translated towards preparation of its congener as well (Scheme 5). Indeed, enantioselective dearomative trans-1,2-carboamination of benzene (9) with more elaborate aryl Grignard reagent 11 furnished the desired diene 8 in 66% yield and 97:3 er. The subsequent epoxidation of this compound with mCPBA, consistently provided low yields, likely due to an increased steric hindrance introduced by an additional methoxy group on the arene moiety. Gratifyingly, in situ generated dimethyldioxirane[33] provided the desired allylic epoxide that was hydrolyzed to trans-diol 29 using aqueous NaOBz. The remaining steps, Upjohn dihydroxylation (29→30), urazole fragmentation (30→6), carbamate preparation (6→31), and Bischler-Napieralski reaction (31→32) proceeded smoothly, furnishing protected pancratistatin (32) in 87% yield. It is important to note that application of Hendrickson's reagent for this cyclization proved to be more efficient and selective (10:1 r.r) compared to most of the previously reported cyclizations in similar systems. Finally, global deprotection of 32 with BBr$_3$ followed by NaOMe provided (+)-pancratistatin (2) in 50% yield over two steps.

Scheme 4 a)

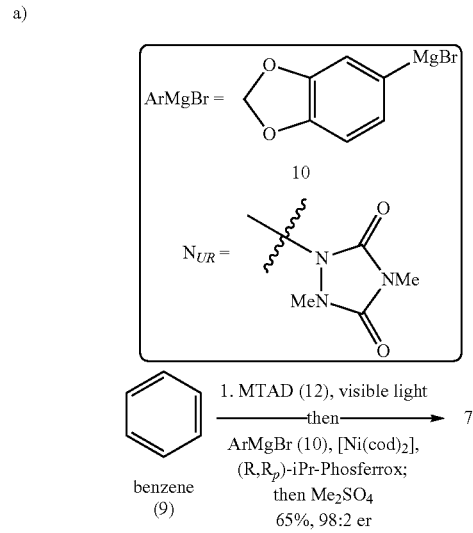

First generation approaches to (+)-7-deoxypancratistaitin (1). a) Synthesis of aminotetraol 5. b) Conversion of aminotetraol 5 to (+)-7-deoxypancratistatin (1). Reagents and conditions: 1. benzene (9), MTAD (12) CH$_2$Cl$_2$, visible light, -78° C.; then [Ni(cod)$_2$] (5 mol %), (R,R$_p$)-iPr-Phosferrox (10 mol %), Grignard reagent 10, CH$_2$Cl$_2$, THF, -78° C. to 25° C.; then Me$_2$SO$_4$, K$_2$CO$_3$, 65% (98:2 er); 2. mCPBA, NaHCO$_3$, CH$_2$Cl$_2$, 25° C.; 3. NaOBz, H$_2$O, 100° C., 63% over two steps; 4. NMO, OsO$_4$ (5 mol %), tBuOH, H$_2$O, 25° C., 91%; 5. LiAlH$_4$, THF, reflux; then Rochelle salt; then Raney-Co, H$_2$ (1 atm), 60° C., 60%; 6. NBS, THF, H$_2$O, 25° C., 79% 7.OsO$_4$ (5 mol %), NMO, citric acid, acetone, H$_2$O, tBuOH (1:1:2), 25° C.; 8. NaOBz.H$_2$O, 100° C., 42% over two steps; 9. LiAlH$_4$, THF, reflux; then Rochelle salt; then Raney-Co, H$_2$ (1 atm), 60° C., 69%; 10. HMTA, TFA, AcOH, 90° C. 95%; 11. NaClO$_2$, NaH$_2$PO$_4$, 2-methyl-2-butene, THF, H$_2$O, 25° C., 57%; 12. Boc$_2$O, Et$_3$N, 1,4-dioxane, H$_2$O, 25° C.; then Ac$_2$O, Et$_3$N, DMAP, CH$_2$Cl$_2$, 25° C., 76%; 13. Ph$_3$P(O), Tf$_2$O, BF$_3$·Et$_2$O, CH$_2$Cl$_2$, 0° C.; then NaOMe, MeOH, 25° C., 75%.

Scheme 5

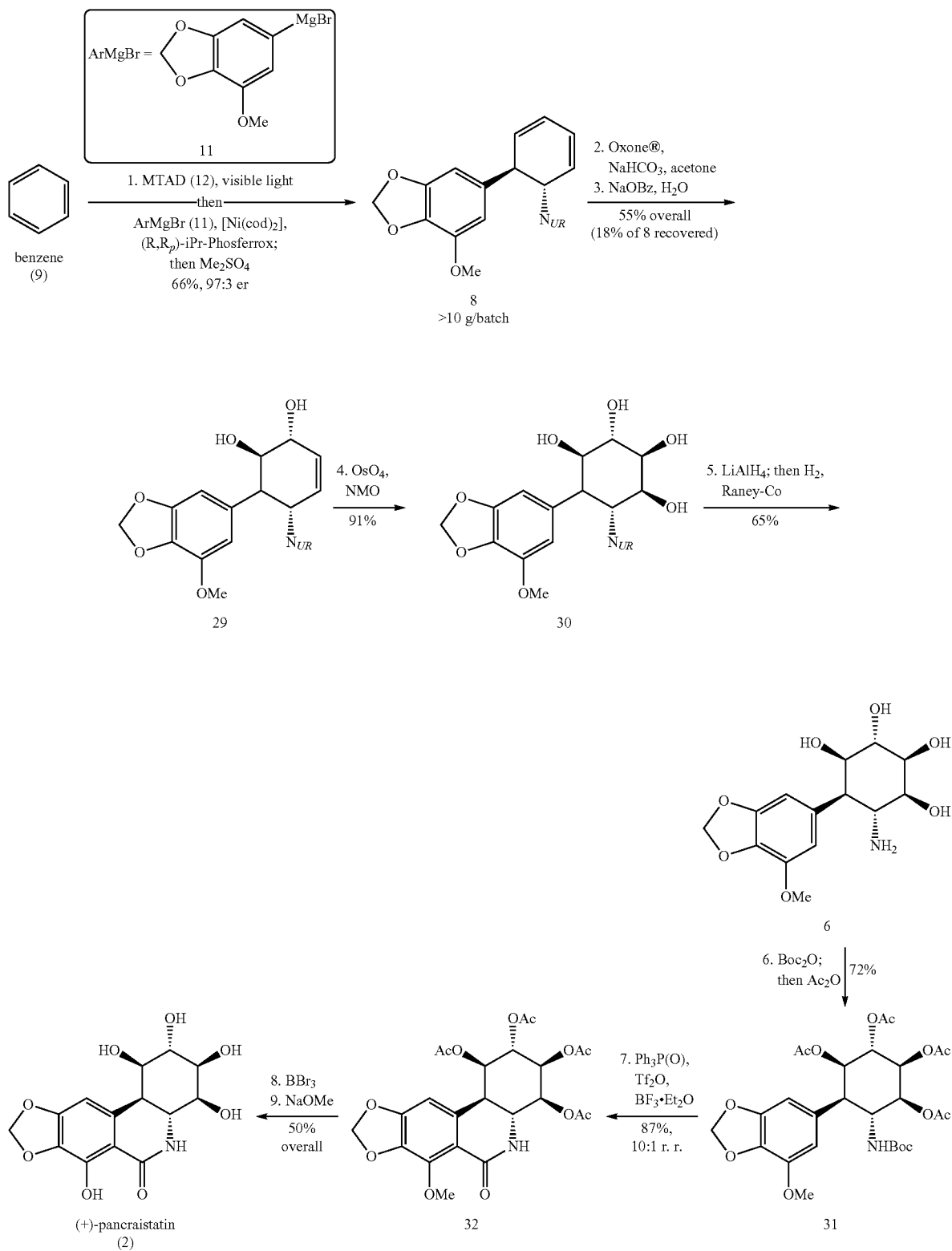

First generation approach to (+)-pancratistatin (2). Reagents and condtitions: 1. benzene (9), MTAD (12), CH₂Cl₂, visible light, -78° C.; then [Ni(cod)₂] (5 mol %), (R,Rₚ)-iPr-Phosferrox (10 mol %), Grignard reagent 11, CH₂Cl₂, THF, -78° C. to 25° C.; then MeSO₄, K₂CO₃, 66% (97:3 er); 2 Oxone®, NaHCO₃, acetone, H₂O, 25° C.; 3. NaOBz, H₂O, 100° C., 55% over two steps (18% of 8 recovered); 4. NMO, OsO₄ (5 mol %), tBuOH, H₂O, 25° C., 91%; 5. LiAlH₄, THF, reflux; then Rochelle salt; then Raney-Co, H₂ (1 atm), 60° C., 65%; 6. Boc₂O, Et₃n, 1,4-dioxane, H₂O, 25° C.; then Ac₂O, Et₃N, DMAP, CH₂Cl₂, 25° C., 72%, 7. Ph₃P(O), Tf₂O, BF₃·Et₂O, CH₂Cl₂, 25° C., 87% (10:1 r. r.); 8. BBr₃, CH₂Cl₂, 25° C.; 9. NaOMe, MeOH, 25° C., 50% over two steps.

Streamlined Synthesis of (+)-Pancratistatins. The above-described synthetic campaigns resulted in concise preparation of both (+)-pancratistatins in seven and nine steps, respectively. Though this accomplishment represents the shortest enantioselective approach to the pancratistatins to date, we felt there was still room for improvement, mainly to increase atom, step, and redox economy, all of which are desired for the practical synthesis of such compounds. Specifically, installation of the trans-diol and lactam formation required intermediary steps, such as protecting group manipulations and discrete oxidation level alterations. Moreover, as in all previous synthetic endeavors, 1 and 2 each required individual de-novo total synthesis from the corresponding C-7 substituted aromatic building blocks, which provided an additional roadblock in synthetic development. Finally, the precursor for functionalized Grignard reagent 11 required three synthetic operations from o-vanillin, whereas the precursor for Grignard 10 was commercially available.

With these key challenges in mind, we set forth to further streamline our synthesis of the pancratistatins and to provide a direct synthetic connection between 1 and 2 (Scheme 6). During initial studies of the epoxidation of diene 7, we frequently observed small amounts of the desired trans-diol 22 during the epoxidation step; therefore, we explored the viability of a one-pot, trans-dihydroxylation protocol. Indeed, this approach proved to be successful when the epoxidation reaction was conducted in the presence of pTsOH and a large excess of water. In addition, the use of hexafluoroisopropanol (HFIP) as a solvent was essential to obtain diol product 22 in 74% yield. This represented a marked increase in yield (63→74%) as well as removed a chromatographic purification from the early sequence, improving the preparation of diol 22. At this point, the remaining transformations towards aminotetraol 5 remained the same, as they were already scalable and reproducible.

We next wanted to improve the overall efficiency of the lactam formation as our previously described approach required five protecting groups for the installation of a single carbonyl group. However, we knew that the introduction of carbonyl functionality in the presence of four free alcohols would prove challenging with respect to achieving the desired chemoselectivity. To this end, we were able to install a bromine substituent at the desired position (8:1 r.r.) on the electron-rich arene ring by exposing aminotetraol 5 to bromine under acidic conditions. The installed halogen provided a handle for the exploration of carbonyl insertion through carbonylative coupling chemistry. Accordingly, we began investigating various benchmark Pd-catalyzed carbonylative coupling procedures; however, we unfortunately observed only complex mixtures of oxidized intermediates and precipitation of Pd black. This was somewhat expected, as palladium is well known to oxidize similar substrates and, to the best of our knowledge, carbonylative couplings involving aryl bromides in the presence of free primary and secondary alcohols has yet to be developed.

We then turned our focus to explore catalytic carbonylation based on other metals that are known to tolerate free alcohols. Along these lines, we tested a set of conditions reported by Caubere and coworkers that employed dicobalt octacarbonyl under highly basic aqueous conditions (5M NaOH) and UV irradiation. According to the proposed mechanism, such transformations proceed through photoinduced electron- or charge-transfer complexes between aryl halides and $[Co(CO)_4]^-$, resulting in the formation of aroyl-cobalt carbonyl complexes of type I-1, which should readily collapse to lactam product 1 with concurrent regeneration of catalyst $[Co(CO)_4]^-$. Indeed, using Caubere's protocol we were encouraged to find that (+)-7-deoxypancratistatin (1) could be observed in low yield, with rest of the mass balance being recovered starting material and an amino acid, likely resulting from subsequent base-induced hydrolysis. This suspicion was further validated by the fact that longer reaction times led to lower yields and larger amounts of the amino acid, which proved challenging to convert back to 1. Therefore, it became apparent that the highly basic reaction environment was causing the lower yields, and development of more neutral reaction conditions was needed. The main role of NaOH in the original report was to convert $Co_2(CO)_8$ to active $NaCo(CO)_4$, and to serve as a base that sequestered HBr. Thus, we prepared pure $NaCo(CO)_4$, and utilized it in the reaction alongside $NaHCO_3$ as a mild HBr scavenger, resulting in formation of (+)-7-deoxypancratistatin (1) in 72% overall yield from aminotetraol 5. For ease of operation, the bromination and carbonylative coupling were performed in a single reaction vessel, with only a solvent exchange as an intermediary step.

The final synthetic challenge left was to establish a direct connection between the pancratistatins (1→2), which would completely remove the need for the use of tailored Grignard reagent 11 as well as de-novo synthesis of 2. In addition to providing this link, such a C-7 functionalization could also enable facile synthesis of analogs at this position. Many methods for this formal oxidative transformation were investigated, including direct $sp^2$ C—H oxidation, indirect $sp^2$ C—H borylation/oxidation, and various directed ortho metalation/oxidation procedures.

Scheme 6

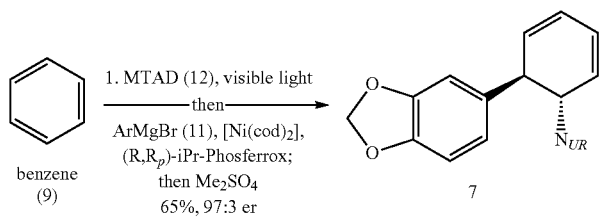

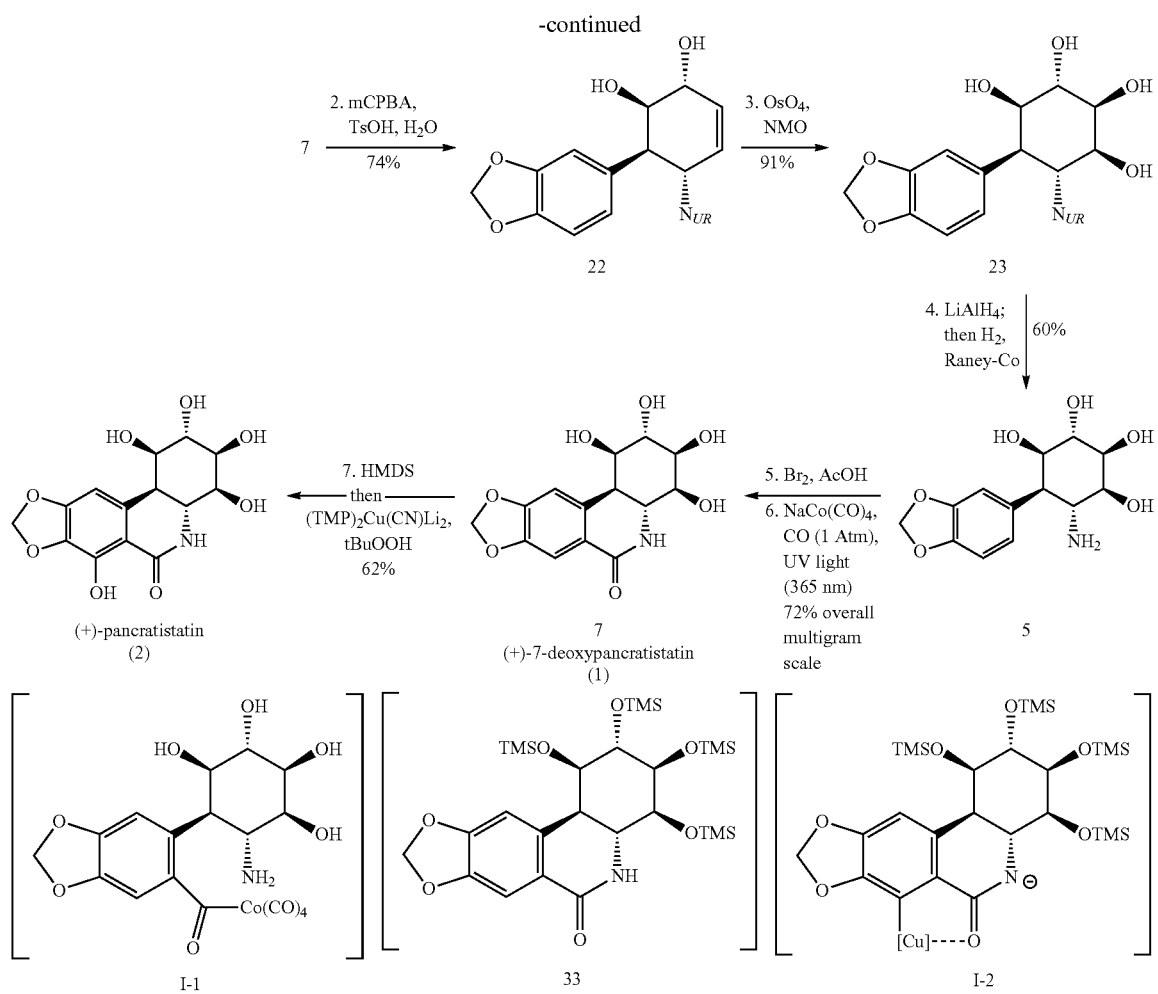

Streamlined synthesis of pancratistatins 1 and 2. Reagents and conditions: 1. benzene (9), MTAD (12), $CH_2Cl_2$, visible light, -78° C.; then [Ni(cod)$_2$], (5 mol %), (R,R$_p$)-iPr-Phosferrox (10 mol %), Grignard reagent 10, $CH_2Cl_2$, THF, -78° C. to 25° C,; then $Me_2SO_4$, $K_2CO_3$, 65% (98:2 er); 2. mCPBA, pTsOH, $CH_2Cl_2$, HFIP, $H_2O$, 50° C., 74%; 3. NMO, $OsO_4$ (5 mol %), tBuOH, $H_2O$, 25° C., 91%; 4. LiAlH$_4$, THF, reflux; then Rochelle salt; then Raney-Co, $H_2$ (1 atm), 60° C., 60%; 5. Br$_2$, AcOH, 25° C.; 6. NaCo(CO)$_4$ (30 mol %), nBu$_4$NBr, CO (1 atm), NaHCO$_3$, $H_2O$, 1,4-dioxane. 365 nm light, 60° C., 72% over two steps; 7. HMDS, I$_2$ (1 mol %), MeCN, 80° C.; then solvent removal and (TMP)$_2$Cu(CN)Li$_2$, THF, -78° C. → 0° C.; then tBuOOH, THF, -78° C.; acidic workup, 62%.

Undeterred, we eventually found that treating 1 with hexamethyldisilazane (HMDS) in the presence of catalytic amounts of iodine allowed for in situ generation of tetrasilylated 7-deoxypancratistatin 33, which could immediately be subjected to a cupration/oxidation sequence. This formal sp$^2$ C—H oxidation was accomplished using directed cupration with (TMP)$_2$Cu(CN)Li$_2$ and subsequent arylcuprate I-2 oxidation with tBuOOH, conditions recently reported by Uchiyama and coworkers that proved to be robust enough for our complex system, affording (+)-pancratistatin (2) in 62% yield after acidic workup. Of note is the use of HMDS/I$_2$ for global silylation of (+)-7-deoxypancratistatin prior to the deprotonative cupration, as other common silyl transfer agents, such as TMSCl, TMSCN, TMSN$_3$, N,O-bis(trimethylsilyl)acetamide (BSA), N-Methyl-N-trimethylsilylacetamide (MSA), N-Methyl-N-trimethylsilyltrifluoroacetamide (MSTFA), and N,O-bis(trimethylsilyl)trifluoroacetamide (BSTFA) left stoichiometric impurities that could not be removed without chromatographic purification. Though purification of 33 was possible, the rapid hydrolysis of the silyl groups on silica led to issues in reproducibility. On the other hand, as the only byproduct from the silylation with HMDS is NH$_3$, all volatiles and excess of the reagent could be removed simply through azeotropic distillation with toluene, leaving 33 in sufficient purity for the next operation. Thus, the described synthesis delivers (+)-7-deoxypancratistatin (1) and (+)-pancratistatin (2) in six and seven operations and in 19% and 12% overall yield. It is important to note that using this streamlined synthetic sequence, we have prepared several grams of both pancratistatins to date, showcasing the scalability of the above-described approach.

Synthesis of((+)-Narciclasine. With the practical synthesis of pancratistatins completed, we turned our attention towards (+)-lycoricidine (3) and (+)-narciclasine (4). As shown in our retrosynthetic analysis (Scheme 2), we surmised that compounds 13 and 14 could be viable intermediates to reach the unsaturated aminocyclitol core of 3 and 4 through a base-promoted epoxide isomerization and concurrent arylmetal attack into the urazole ring, resulting in carbonyl transfer and assembly of the lactam. We were particularly interested in exploring such intermediates because they could be readily traced back to dienes 7 and 8, using olefin functionalization chemistry. In addition to our previous success in handling these compounds, we also recently improved the dearomative trans-1,2-carboamination strategy, which permitted the preparation of these intermediates on a multi-decagram scale without the use of a glovebox. Although we initially used 5 mol % of [Ni(cod)$_2$] as a precatalyst for the synthesis of the pancratistatins (Schemes 4-6), we further optimized this protocol to permit the application of air-stable [Ni(acac)$_2$] in much lower loadings ([Ni]/ligand=1.5/2.0 mol %).

Scheme 7

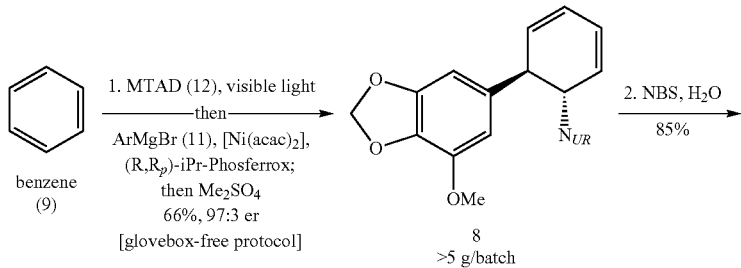

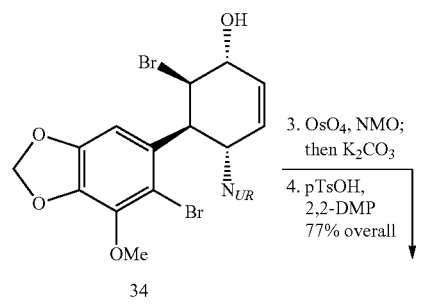

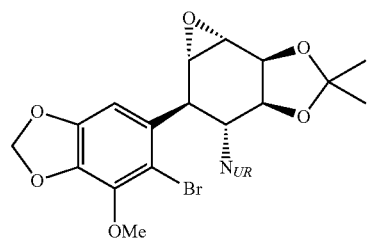

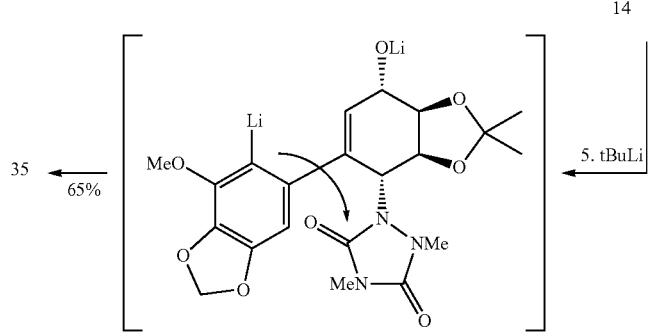

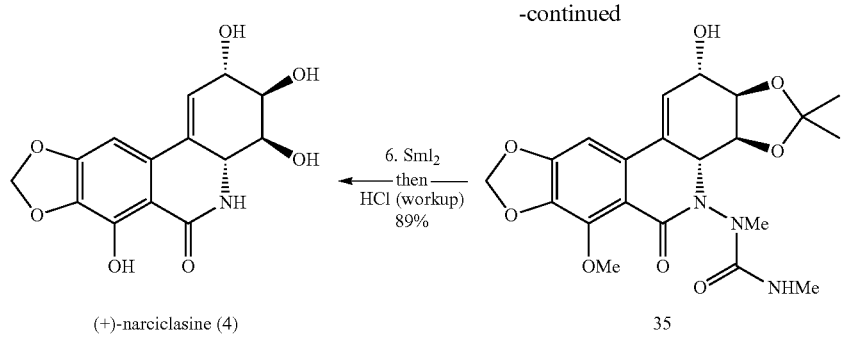

(+)-narciclasine (4)                                           35

Synthesis of (+)-narciclasine (4). Reagents and conditions: 1. benzene (9), MTAD (12), CH$_2$Cl$_2$, visible light, -78° C.; then [Ni(acac)$_2$] (1.5 mol%), (R,R$_p$)-iPr-Phosferrox (2.0 mol %), Grignard reagent 11, CH$_2$Cl$_2$, THF, -78° C. to 25° C.; then Me$_2$SO$_4$, K$_2$CO$_3$, 66% (97:3 er); 2. NBS, H$_2$O, THF, 25° C., 85%; 3. OsO$_4$ (5 mol %), NMO, citric acid, acetone, H$_2$O, tBuOH, 25° C.; then K$_2$CO$_3$, 25° C.; 4. 2,2-dimethoxypropane, pTsOH (10 mol %), CH$_2$Cl$_2$, 25° C., 77% over two steps; 5. tBuLi, THF, -78° C., 65%; 6 SmI$_2$, MeOH, 0° C.; then 40° C.; then HCl, 0° C., 89%.

At the onset of our studies towards (+)-narciclasine (4), we commenced by targeting key intermediate 14 (Scheme 7). Thus, diene 8, which was prepared in 66% yield and 97:3 er using the new protocol, was exposed to an excess of NBS in THF/H$_2$O, affording dibromide 34 as a single diastereo- and constitutional isomer in 85% yield. Exposure of this compound to Upjohn dihydroxylation conditions with a basic work up (K$_2$CO$_3$), followed by acetonide protection of the intermediate epoxy diol, gave key bromoepoxide 14 in 77% yield over two steps. One pot dihydroxylation/bromohydrin closure was developed for practical reasons, as the dibromotriol proved challenging to extract and purify. This compound, which is prepared from benzene in four steps, contains all the necessary atoms that are present in narciclasine (4), as well as strategically placed functional handles for conversion to the natural product. Specifically, the stereochemical relationship between the epoxide and the benzylic hydrogen is appropriate for a formal syn-epoxide elimination, which would provide the desired allylic alcohol. Moreover, the arylbromide moiety serves as a precursor to an arylmetal species that could add into the nearby urazole carbonyl group and form the desired lactam. To our delight, we discovered that the slow addition of tBuLi to a cold solution of 14 could achieve both epoxide isomerization and benzamide formation, likely through the intermediate I-3, providing compound 35 in 65% yield. Furthermore, although 14 contains two neighboring hydrogens, both in syn-quasi axial position (for an X-ray of similar compound 13, see Scheme 8, bottom) only product 35 was observed, resulting from elimination of the more acidic benzylic proton.

With the phenanthridone skeleton completed, the final task en route to narciclasine (4) was reductive N—N bond cleavage of acylsemicarbazide 35 and global deprotection. This was achieved by slow addition of freshly prepared SmI$_2$, followed by mild heating and subsequent acidic workup, to deliver (+)-narciclasine (4) in 89% yield. Heating this reaction to 40° C. proved crucial to achieve full Sm(III)-mediated deprotection of the aryl methoxy group, and the acidic workup was favored over other common procedures, which gave heterogeneous mixtures that were tedious to separate and extract. Thus, using this six step protocol with 25% overall yield, we were able to obtain more than 600 mg of (+)-narciclasine (4) in a single pass from benzene (9).

Scalable Route to (+)-Lycoricidine and (+)-Narciclasine. With the successful application of the late-stage hydroxylation at C-7 in the case of pancratistatins (1→2, see Scheme 6), we wondered if the same chemical connection could also be feasible between lycoricidine (3) and narciclasine (4). The major benefits of such a direct conversion would be: (1) application of readily available Grignard 10 instead of non-commercial reagent 11; (2) avoidance of individual de-novo total synthesis of 3 and 4; and (3) rapid preparation of C-7 analogs to fully explore this position of the pharmacophore.

By employing a glovebox-free procedure and operationally simple photoreactor, we prepared dearomatized product 7 on more than 100 mmol scale (>25 g) in 65% yield and 97:3 er after methylation with Me$_2$SO$_4$. Following a similar sequence to the one described above, diene 7 was subjected to two equivalents of NBS in THF and H$_2$O to produce bromohydrin 25 in 79% yield. Subsequent Upjohn dihydroxylation, base-mediated epoxide formation, and diol protection, furnished epoxy acetonide 13 in 78% overall yield, setting the stage for the key epoxide isomerization/lactam formation cascade (see bottom of Scheme 8 for an X-ray of 13). Thus, dropwise addition of tBuLi to a cold solution of 13 provided intermediate 36 in 70% yield on >20 g scale. Interestingly, only 2.35 equivalents of tBuLi were needed to achieve full conversion on large scale, as addition of further equivalents only led to decomposition of the product. Treatment of lactam 36 with SmI$_2$, followed by acidic work up delivered (+)-lycoricidine (3) in 94% yield, and we produced slightly over 8 g of this natural product in a single pass. Moreover, we obtained single crystals suitable for X-ray crystallographic analysis (Scheme 8, bottom). To avoid stoichiometric use of SmI$_2$, we have also explored reductive N—N bond cleavage employing catalytic amounts of SmI$_2$ with an electrochemical method recently reported by the Ackermann group (Scheme 8 inset). While the scalability of this reaction has yet to be tested, preliminary results suggest that a more economical approach could be feasible, as product 37 was obtained in 45% yield (52% of 36 recovered).

Finally, with ample amounts of (+)-lycoricidine (3) in hand, we set out to examine C-7 functionalization using the deprotonative cupration/oxidation conditions previously developed to convert (+)-7-deoxypancratistatin (1) to (+)-pancratistatin (2). Our initial attempts employed lycoricidine acetonide 37 and required catalytic amounts of TFA to mediate the silylation, as 12 led to the formation of byproducts. After screening numerous conditions with lycoricidine acetonide 37, only minimal (<10%) conversion to the desired product was observed. However, we found that direct conversion of lycoricidine (3) to silylated lycoricidine, followed by addition of (TMP)$_2$Cu(CN)Li$_2$, subsequent in situ oxidation of arylcuprate species with tert-butyl hydroperoxide, and acidic workup delivered (+)-narciclasine (4). Importantly, we were able to run this oxidation on a 3 g scale, obtaining a 57% yield and isolating >1.8 g of (+)-narciclasine (4). Over the course of this study, we conveniently prepared >20 g of 3 and >5 g of 4 in total, demonstrating the scalability of the approach described herein.

Scheme 8

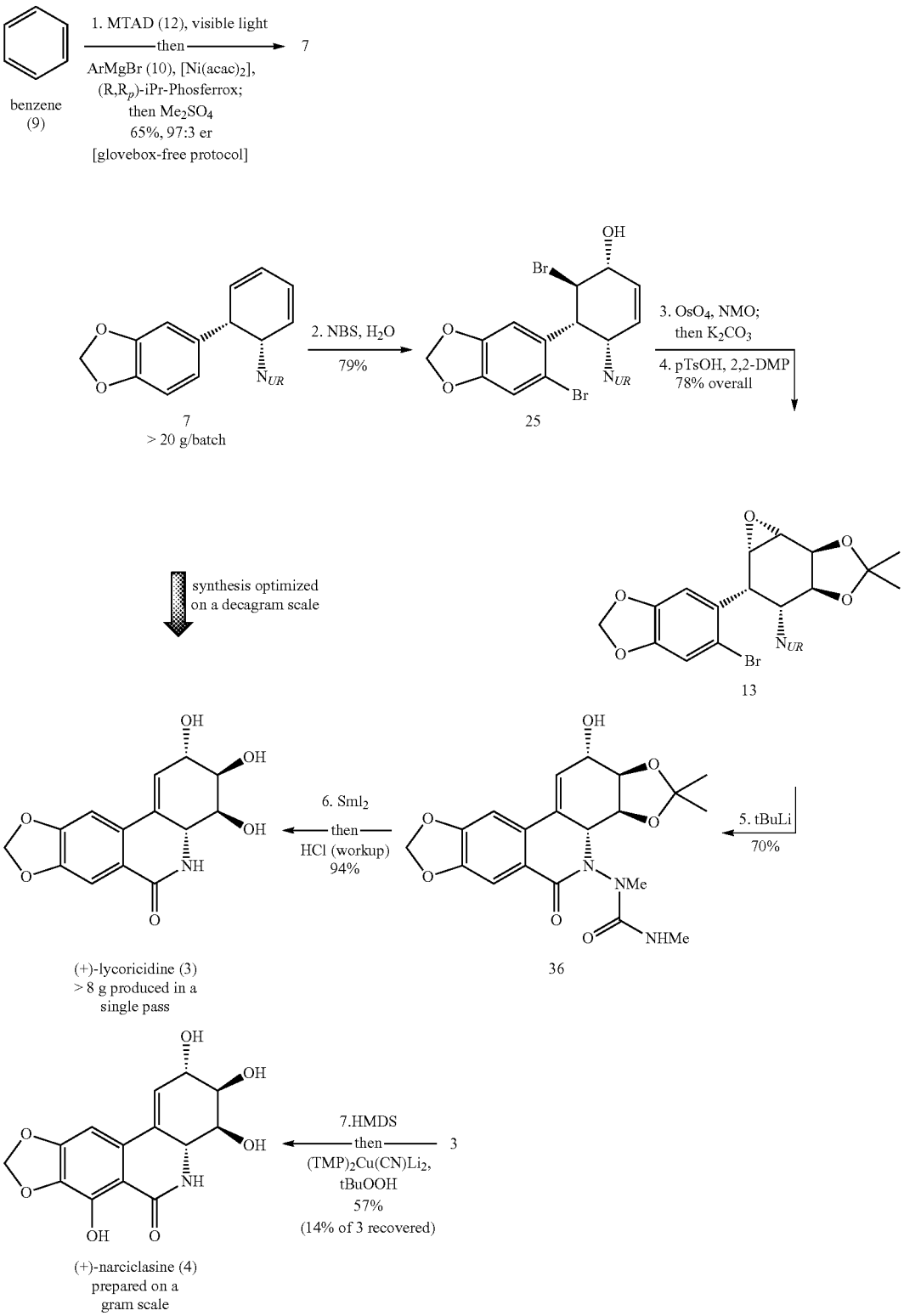

-continued

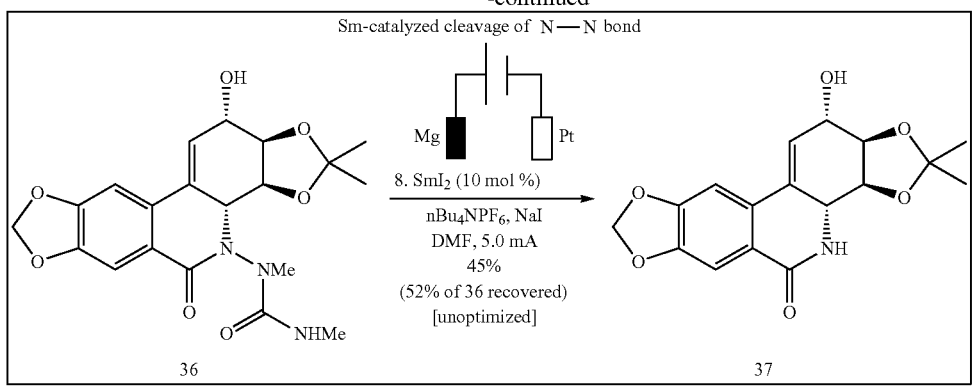

Synthesis of (+)-lycoricidine (3) and (+)-narciclasine (4). Reagents and conditions: 1. benzene (9), MTAD (12), CH$_2$Cl$_2$, visible light, -78° C.; then [Ni(acac)$_2$] (1.5 mol %), (R,R$_p$)-iPr-Phosferrox (2.0 mol %), Grignard reagent 10, CH$_2$Cl$_2$, THF, -78° C., to 25° C.; then Me$_2$SO$_4$, K$_2$CO$_3$, 65% (97:3); 2. NBS, H$_2$O, THF, 25° C., 79%; 3. OsO$_4$ (5 mol %), NMO, citric acid, acetone, H$_2$O, tBuOH, 25° C.; then K$_2$CO$_3$, 25° C.; 4. 2,2-dimethoxypropane, pTsOH (10 mol %), CH$_2$Cl$_2$, 25° C., 78% over two steps; 5. tBuLi, THF, -78° C., 70%; 6. SmI$_2$, MeOH, 0° C., then HCl, 0° C., 94%; 7. HMDS, TFA (1.0 mol %) MeCN, 25° C.; then solvent removal and (TMP)$_2$Cu(CN)Li$_2$, THF, -78° C. → 0° C.; then tBuOOH, THF, -78° C.; acidic work up, 57% (14% of 3 recovered); 8. NaI, nBu$_4$NPF$_6$, SmI$_2$ (10 mol %), DMF, 25° C., Mg anode, Pt cathode, 5.0 mA, 45% (52% of 36 recovered).

Synthesis and Biological Evaluation of C-7 Analogs. With gram amounts of (+)-lycoricidine (3) now readily available, as well as an established late-stage cupration procedure, we turned our attention to the preparation of the corresponding C-7 analogs (Scheme 9). Previous synthetic efforts have provided basic structure-activity correlations, revealing the importance of certain functionalities and their stereochemical orientation, mainly on the aminocyclitol core. However, the influence of C-7 substitution has not been significantly investigated. This comes as no surprise, as each C-7 derivative would previously require a multistep synthesis, making the preparation of a library of C-7 analogs very time consuming. By using Uchiyama's cupration-based strategy, alkyl- and amine-based functionalities were selectively introduced at position 7 in a single operation from 3 (Scheme 9a). For example, exposure of lycoricidine-derived cuprate intermediate I-4 to alkyl electrophiles or O-benzoyl hydroxylamines provided a range of C- (38-42, 44, and 46) and N-substituted analogs (47-51) respectively. Simple saponification of esters 42 and 44 provided carboxylic acids 43 and 45. This C-7 diversification could be also applied to the pancratistatin series, as demonstrated with the preparation of 7-aminopancratistatin (52, Scheme 9b). However, amine analogs 47, 48 and 52, could not be made directly due to purification issues and consequently had to be synthesized from the corresponding allyl substituted O-benzoyl hydroxylamine, followed by allyl deprotection (for example, see Scheme 9b).

With a small library of analogs in hand (38-52), their anticancer activities, as well as those of the natural products (1-4), were measured using human lung and colon cancer cell lines (A549 and HCT116). As expected, the C-7 substituent plays an important role in the activity of these compounds. Alkyl substituents drastically reduced the activity as C-analogs 38-45 displayed weaker potency than lycoricidine (3), with activities ranging from 29 to >100 μM. Even derivatives containing hydrogen-bond donor or acceptor groups, such as homologue 41, differing from narciclasine by an additional CH$_2$ group, proved to be less potent. Interestingly, 7-cyanolycoricidine (46) showed increased activity when compared to lycoricidine (3) in HCT116 cells. Furthermore, introduction of an amino group improved activity over lycoricidine, as exemplified with 7-aminolycoricidine (47) which possesses an IC$_{50}$ of 0.39 μM in HCT116 cells. However, other N-analogs containing alkylated amines, such as methylamine (48), acetamide (49), pyrrolidine (50), and morpholine (51) did not show significant cytotoxicity, pointing at the importance of an —XH type of motif (X=O, NH) for enhanced activity.

Finally, we also evaluated the solubility of the most active amino analogs (FIG. 1b). Natural isocarbostyril alkaloids 1-4 are known to be highly insoluble; however, 7-aminolycoricidine (47) and 7-aminopancratistatin (52) showed 11- and 6-fold increased solubility when compared to their natural counterparts. The improved aqueous solubility and comparable activity make these new C-7 amino analogs attractive targets for further diversification and study.

Metabolic Stability. Though numerous in vitro and several in vivo evaluations of isocarbostyril alkaloids gave promising results, there are no reports describing metabolism of these compounds, despite the fact that the results obtained from such studies would help with the planning or interpretation of clinical and toxicological studies. Over the years, many procedures have emerged for studying metabolic stability and the identification of metabolites, including deuterium labeling. By taking advantage of the kinetic isotope effect (KIE) one can increase the metabolic stability of a compound by incorporating deuterium at the potentially metabolically compromised site.

One of the unique advantages of the arenophile-based approach is the ability to provide selective access to tailored stable isotopologs, as most of the starting aromatic compounds are readily available in their deuterated forms (FIG. 1c). Using our previous synthetic strategy, substitution of benzene (9) for benzene-d$_6$ (9-d$_6$) led to narciclasine analog 4-d$_5$, which has each proton on the cyclitol core replaced with a deuterium. Likewise, employing selectively labeled Grignard precursor 11-d$_2$, which can be easily prepared using CD$_2$Cl$_2$, we have been able to synthesize narciclasine isotopolog 4-d$_2$, which has deuterium incorporated into the methylene bridge. With these differentially deuterated compounds in hand, we tested their activity and metabolic stability using a microsome assay. While both labeled compounds 4-d$_5$ and 4-d$_2$ have equipotent activity, they showed noticeably (~30%) greater metabolic stability when compared to narciclasine (4), suggesting that both the methylene bridge and the cyclitol core are susceptible to metabolic degradation.

Scheme 9

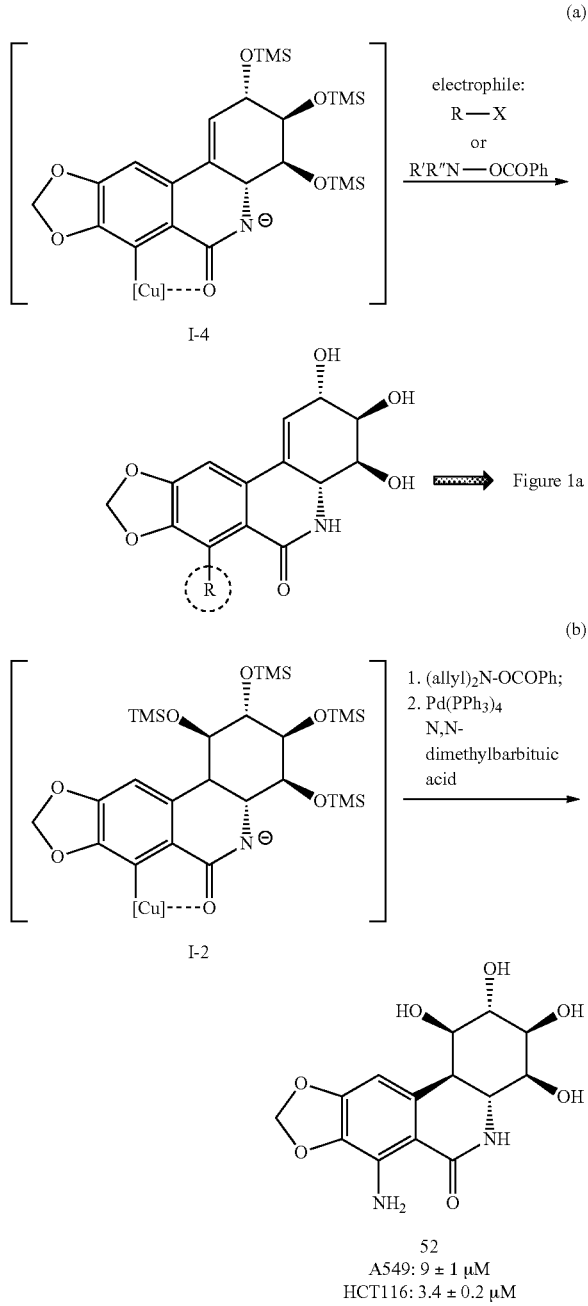

a) Late-stage preparation and anticancer activity of C-7 analogs of lycoricidine (3). Cell viability was assessed after 72 hours using the Alamar Blue assay, n ≥ 3, SEM for each measurement is in the Examples. Doxorubicin (Dox) was used as a reference (See Figure 1a for IC$_{50}$ values. b) Preparation and activity of 7-aminopancratistatin 52.

Conclusion. Our streamlined route to the pancratistatins featured three olefin-like difunctionalizations of benzene and a late stage carbonylative coupling reaction that gave (+)-7-deoxypancratistatin (1) in six steps and 19% overall yield. One pot amide-directed deprotonative cupration and subsequent arylcuprate oxidation allowed for the installation of the C-7 hydroxyl group present in (+)-pancratistatin (2). The route to lycoricidine (3) featured a base-promoted epoxide isomerization/lactam formation cascade reaction followed by Smb mediated N—N reductive cleavage, delivering the natural product in six steps and 26% overall yield. Utilizing this strategy, we have synthesized several grams of each natural product to date, showcasing the scalability of our approach. Furthermore, large scale access to these natural products, coupled with an enabling directed cupration, resulted in the synthesis of a small library of C-7 analogs. Of these, 7-aminolycoricidine (47) showed enhanced activity over its natural counterpart, as well as significantly improved aqueous solubility. The brevity of described approach and the availability of deuterated starting arenes also prompted the synthesis of differentially deuterated narciclasine isotopologs 4-d$_5$ and 4-d$_2$, both of which had improved metabolic stability when compared to non-labeled natural product 4. We anticipate that the concise and scalable syntheses, as well as new avenues for derivatization reported in this article, will provide a new practical means of supplying these medicinally important compounds and further invigorate their biological investigations.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; Protecting Groups (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective anti-tumor agents and have higher potency and/or reduced toxicity as compared to, pancratistatin. Preferably, compounds of the invention are more potent and less toxic than pancratistatin, and/or avoid a potential site of catabolic metabolism encountered with pancratistatin, i.e., have a different metabolic profile than pancratistatin.

The invention provides therapeutic methods of treating cancer in a subject, i.e, a mammal or invetebrate, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell-kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Methods and Synthesis

General experimental: Unless otherwise noted, all reactions were carried out under an ambient atmosphere. All chemicals were purchased from commercial suppliers and used as received. N-methyl-1,2,4-triazoline-3,5-dione (MTAD 12) was prepared based on the literature procedures (Tetrahedron Lett. 2014, 55, 4661) and was resublimed before use. (R,R$_p$)-iPr-Phosferrox was prepared based on the literature procedure (Org. Synth. 2009, 86, 181) from D-valinol. Cis-derivatized $SiO_2$ was prepared according to the literature procedure (J. Inorg. Chem. 1970, 9, 1932). Dry dichloromethane ($CH_2Cl_2$), and tetrahydrofuran (THF) were obtained by passing commercially available anhydrous, oxygen-free HPLC-grade solvents through activated alumina columns. Analytical thin-layer chromatography was performed on Merck silica gel 60 F254 aluminum plates. Visualization was accomplished with UV light and/or potassium permanganate ($KMnO_4$). Retention factor ($R_f$) values reported were measured using a 5×2 cm TLC plate in a developing chamber containing the solvent system described. Flash column chromatography was performed using Silicycle SiliaFlash® P60 ($SiO_2$, 40-63 μm particle size, 230-400 mesh). $^1H$ and $^{13}C$ NMR spectra were recorded on Bruker 500 (500 MHz, $^1H$; 126 MHz, $^{13}C$) or Varian Unity Inova 500 (500 MHz, $^1H$) spectrometers. Spectra are referenced to residual chloroform (δ=7.26 ppm, $^1H$; 77.16 ppm, $^{13}C$), residual methanol (δ=3.31 ppm, $^1H$; 49.00 ppm, $^{13}C$), residual benzene (δ=7.16 ppm, $^1H$; 128.06 ppm, $^{13}C$), residual $H_2O$ (δ=4.76 ppm, $^1H$) or residual dimethyl sulfoxide (δ=2.50 ppm, $^1H$; 39.5 ppm, $^{13}C$). Chemical shifts are reported in parts per million (ppm). Multiplicities are indicated by s (singlet), d (doublet), t (triplet), q (quartet), m (multiplet), and br (broad). Coupling constants J are reported in Hertz (Hz). Mass spectrometry (MS) was performed by the University of Illinois Mass Spectrometry Laboratory. Electrospray ionization (ESI+) spectra were performed using a time-of-flight (TOF) mass analyzer. Data are reported in the form of m/z (intensity relative to the base peak=100). For several compounds, Waters Q-TOF Ultima ESI and Agilent 6230 ESI TOF LC/MS spectrometers were used to obtain the high-resolution mass spectra. Infrared spectra were measured neat on a Perkin-Elmer spectrum BX FT-IR spectrometer. Peaks are reported in cm$^{-1}$ with indicated relative intensities: s (strong, 0-33% T); m (medium, 34-66% T), w (weak, 67-100% T), and br (broad). Visible-light spectrum of LED was recorded using an Avantes Sensline Avaspec-ULS TEC Spectrometer. Melting points of solids, compounds that solidified after chromatography, were measured on a Buchi B-540 melting point apparatus and are uncorrected. Optical rotations were recorded on a Jasco P-2000 polarimeter at 589 nm, and are reported in units of $10^{-1}$ (deg cm$^2$ g$^{-1}$). HPLC was performed on a Shimadzu Prominence HPLC system with SPD-M20A UV/VIS Photodiode array detector (220 nm). LC-MS was performed on a Shimadzu Nexera XR UHPLC system with SPD-M30A UV/VIS Photodiode array detector and LC-MS 2020 mass spectrometer. Electrochemical reactions were run using an IKA ElectraSyn 2.0. Electrodes were purchased from IKA and used as received. The x-ray diffraction experiments were conducted using Bruker D8 Venture/Photon 100 diffractometer or Bruker APEX-II CCD diffractometer. Using Olex2 (Appl. Cryst. 2009, 42, 339), the structure was solved with ShelXT (Acta Cryst. 2015, A71, 3) structure solution program using Intrinsic Phasing solution method, and the XL (Acta Cryst. 2008, A64, 112) refinement package using Least Squares minimization.

LED light source: Generic cool white light LED corn bulbs were used for the photochemical experiments. These can be obtained from several manufactures over amazon.com and proved to give consistent results as well as identical visible spectra.

Detailed Info:

Socket: G4; LED Chip: 48 LEDs SMD 2835; Consume wattage: 4W; Input voltage: AC/DC 12V; Beam degree: 360 degrees; Color temperature: 6500K (Cool White); Initial Lumens (lm): 290.

Ligand Scope for Ni-Catalyzed Dearomative Trans-1,2-Carboamination.

TABLE 1

Survey of bidentate ligands.[a]

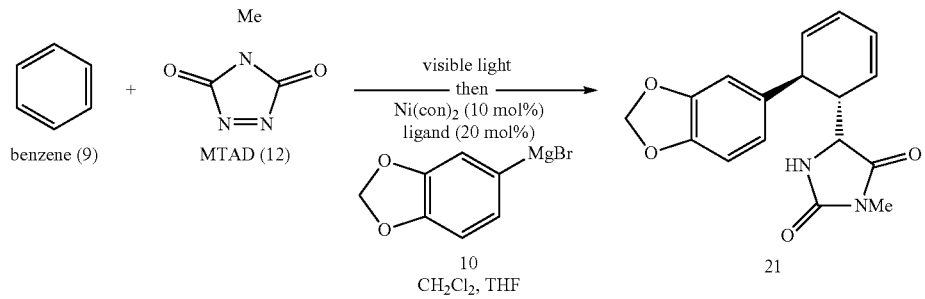

achiral P,P-ligands:

dppe (n = 2): 55%
dppp (n = 3): 24%
dppb (n = 4): 14%
dpppent (n = 5): 17%
dpphex (n = 6): 45%

TABLE 1-continued
Survey of bidentate ligands.[a]
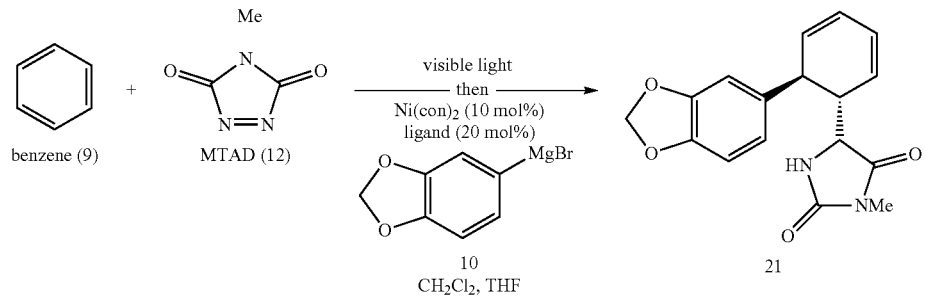
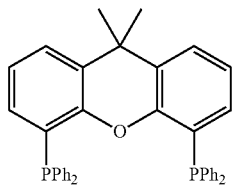
xantphos: 21%
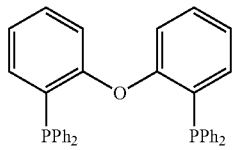
DPEPhos: 57%
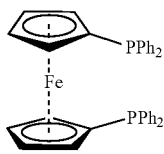
dppf: 74%
chiral P,P-ligands:
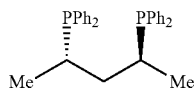
(S,S)-BDPP
27% (90:10 er)
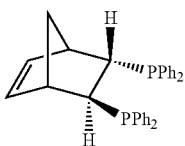
(S,S)-NORPHOS
65% (68:32 er)

TABLE 1-continued
Survey of bidentate ligands.[a]
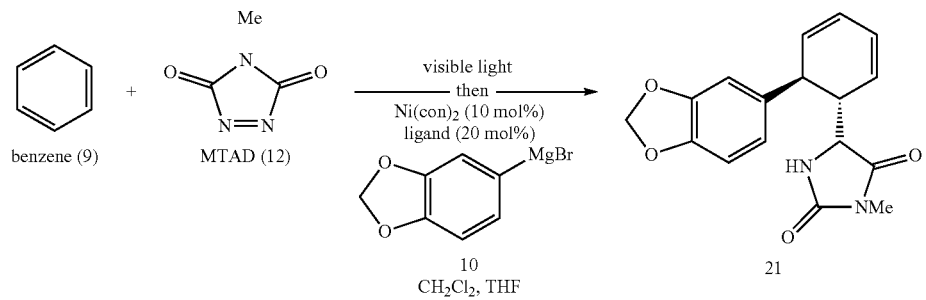
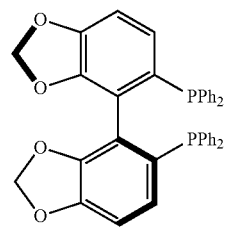
(S)-SEGPHOS
27% (62:38 er)
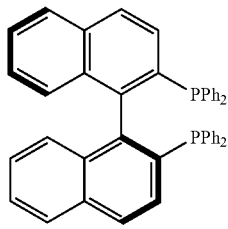
(S)-BINAP
11% (63:37 er)
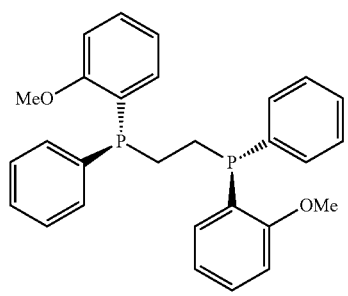
(S,S)-DIPAMP
no reaction TABLE 1-continued
Survey of bidentate ligands.[a]
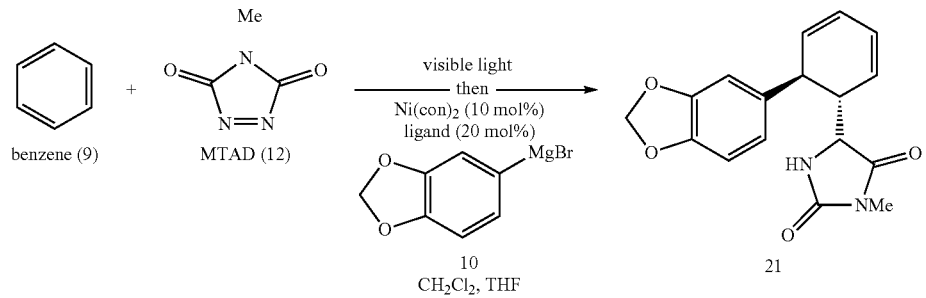
chiral P,N-ligands:
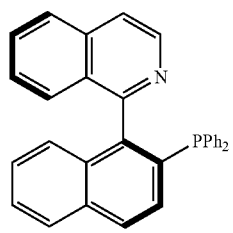
(S)-QUINAP
no reaction
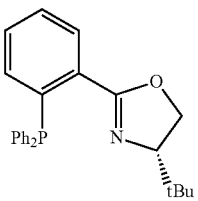
(S)-tBu-PHOX
30% (66:34 er)
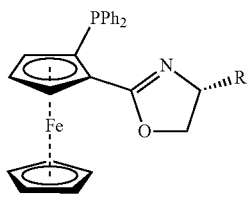
(R,R$_p$)-Phosferrox-type ligands
R = Bn (59%, 95:5 er)
R = iPr (75%, 98:2 er)
R = tBu (26%, 85:15 er)

Example 2. Synthesis and Characterization of Urazole Compound

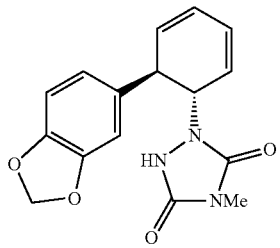

21

Synthesis of diene 21: In an oven-dried test tube, MTAD (12, 45.2 mg, 0.40 mmol, 1.0 equiv.) was dissolved in anhydrous $CH_2Cl_2$ (4 mL) under nitrogen atmosphere and cooled to −78° C. Benzene (9, 356 μL, 4.00 mmol, 10 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(cod)$_2$] (11.0 mg, 0.04 mmol, 10 mol %) and (R,R$_p$)-iPr-Phosferrox (38.5 mg, 0.08 mmol, 20 mol %) in $CH_2Cl_2$ (4 mL) was added, followed by dropwise addition of 3,4-methylenedioxyphenylmagnesium bromide (10, 400 μL, 3.0 M in THF, 1.20 mmol, 3.0 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then aq. HCl (2 mL, 1 M) was added. The organic phase was separated and the aqueous phase was extracted with $CH_2Cl_2$ (2×4 mL). The combined organic extracts were dried over $MgSO_4$, filtered and concentrated under reduced pressure. The residue was purified by flash chromatography (SiO$_2$, hexanes:EtOAc=3:1→2:1) to give the desired compound as a colorless solid [94.4 mg, 0.39 mmol, 75%, 98:2 er]. Enantiomeric ratio was determined with HPLC analysis using Diacel Chiracel® OJ-3 column, 25% iPrOH in hexanes, 0.8 mL/min t$_R$(minor)=11.6 min, t$_R$(major)=13.3 min. R$_f$=0.20 (SiO$_2$, hexanes:EtOAc=1:1); $[\alpha]_D^{24}$=+475.9 (c=1.00 in CHCl$_3$); m.p.=160-161° C.

$^1$H NMR (500 MHz, CDCl$_3$) δ 8.30 (s, 1H), 6.76 (d, J=1.2 Hz, 1H), 6.72 (d, J=1.2 Hz, 2H), 6.28 (ddt, J=9.6, 5.4, 1.4 Hz, 1H), 6.13 (dddd, J=9.6, 5.4, 2.0, 1.0 Hz, 1H), 5.96-5.88 (m, 3H), 5.60 (ddt, J=9.6, 4.5, 1.0 Hz, 1H), 4.94 (ddd, J=7.6, 4.5, 1.7 Hz, 1H), 3.68 (ddd, J=7.6, 4.5, 2.0 Hz, 1H), 3.03 (s, 3H).

$^{13}$C NMR (126 MHz, CDCl$_3$) δ 155.1, 153.3, 148.0, 147.0, 133.9, 130.1, 128.7, 123.3, 121.3, 121.1, 108.5, 108.4, 101.2, 57.3, 44.5, 25.3.

HRMS (ESI-TOF, m/z) calcd. For $C_{16}H_{15}N_3O_4$ [M]$^+$ calc.: 313.1063; Found: 313.1071.

IR (ATR, neat, cm$^{-1}$): 3452 (w), 3158 (w), 2891 (w), 1765 (w), 1689 (s), 1502 (m), 1483 (m), 1246 (m), 1037 (m).

Example 3. First Generation Approaches to (+)-7-Deoxypancratistatin (1)

3-1. Synthesis of Aminoteraol 5 Via Epoxidation:

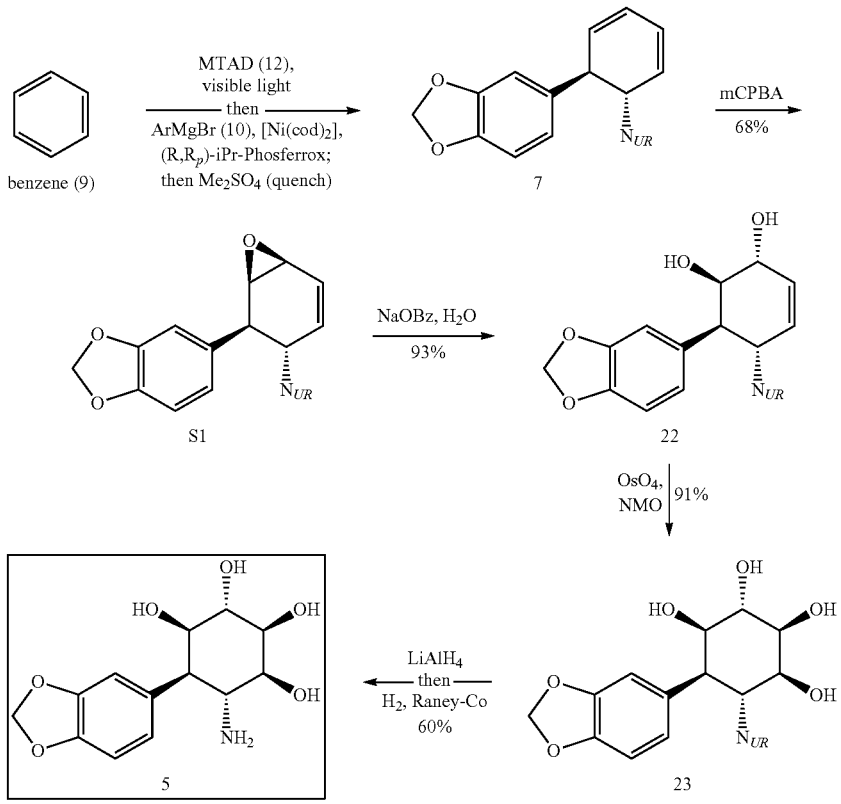

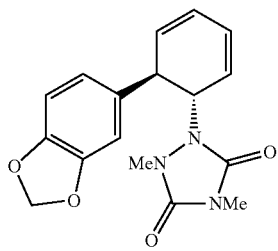

7

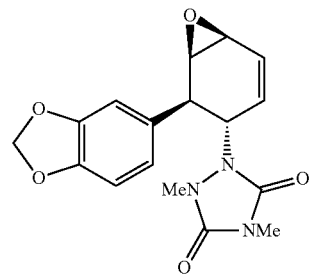

S1

Synthesis of (+)-diene 7: In an oven-dried 1 L media bottle, MTAD (12, 6.00 g, 53.1 mmol, 1.0 equiv.) was dissolved in anhydrous $CH_2Cl_2$ (265 mL) under nitrogen atmosphere and cooled to −78° C. Benzene (9, 47.3 mL, 531 mmol, 10 equiv.) was slowly added and the solution was stirred for five minutes. The pink solution was irradiated with LED lights at −78° C. until complete loss of color. Upon decolorization, the LED lights were turned off and a solution of [Ni(cod)$_2$] (730 mg, 2.65 mmol, 5.0 mol %) and (R,R$_p$)-iPr-Phosferrox (2.55 g, 5.31 mmol, 10 mol %) in $CH_2Cl_2$ (265 mL) was added, followed by dropwise addition of 3,4-methylenedioxyphenylmagnesium bromide (10, 53.1 mL, 3.0 M in THF, 159 mmol, 3.0 equiv.) at the rate to keep the internal temperature below −65° C. After addition, the cold bath temperature was warmed to −45° C. and allowed to slowly warm to 0° C. over 3 h. Reaction vessel was removed from the cold bath and after stirring at room temperature for 15 min, Me$_2$SO$_4$ 50.2 mL, 531 mmol, 10 equiv.) and K$_2$CO$_3$ (22.0 g, 159 mmol, 3.0 equiv.) were added sequentially and the mixture was stirred at 35° C. for 8 h. The mixture was cooled to 0° C. and 5% aq. NH$_4$OH (300 mL) was added, the phases were separated, and the aqueous phase was extracted with $CH_2Cl_2$ (2×200 mL). The combined organic extracts were washed with water (2×200 mL) and brine (200 mL), dried over MgSO$_4$, filtered and concentrated under reduced pressure. The residue was purified by flash chromatography (SiO$_2$, hexanes:EtOAc=5:1→3:1) to give the desired compound as a colorless solid [11.4 g, 34.8 mmol, 65%, 98:2 er].

R$_f$=0.36 (SiO$_2$, hexanes:EtOAc=1:1); $[\alpha]_D^{24}$=+275.9 (c=0.78 in CHCl$_3$); m.p.=121-122° C.

$^1$H NMR (500 MHz, CDCl$_3$) δ 6.75 (d, J=1.8 Hz, 1H), 6.68 (d, J=8.0 Hz, 1H), 6.64 (dd, J=8.0, 1.8 Hz, 1H), 6.15-6.10 (m, 1H), 6.08-6.03 (m, 1H), 5.92 (d, J=1.5 Hz, 1H), 5.91 (d, J=1.5 Hz, 1H), 5.83 (ddt, J=9.3, 3.1, 1.0 Hz, 1H), 5.68 (ddq, J=9.7, 3.1, 1.0 Hz, 1H), 5.12 (dt, J=13.6, 2.9 Hz, 1H), 3.89 (dt, J=13.6, 3.1 Hz, 1H), 3.18 (s, 3H), 2.89 (s, 3H).

$^{13}$C NMR (126 MHz, CDCl$_3$) δ 156.1, 155.1, 147.9, 147.0, 135.4, 130.9, 126.6, 125.5, 123.4, 121.5, 108.7, 108.2, 101.2, 61.0, 44.7, 35.1, 25.5.

HRMS (ESI-TOF, m/z) calcd. For $C_{17}H_{17}N_3O_4Na$ [M+Na]$^+$ calc.: 350.1117; Found: 350.1115.

IR (ATR, neat, cm$^{-1}$): 2895 (m), 2250 (w), 1767 (w), 1700 (s), 1481 (m), 1035 (m), 912 (w), 725 (m).

Synthesis of epoxide S1: To a stirred solution of diene 7 (627 mg, 1.92 mmol, 1.0 equiv.) in $CH_2Cl_2$ (19 mL) at 0° C. was added NaHCO$_3$ (1.61 g, 19.2 mmol, 10 equiv.) and mCPBA (880 mg, 75% w/w, 3.83 mmol, 2.0 equiv.). The resulting suspension was allowed to warm to room temperature and stirred overnight. Upon completion (TLC monitoring), the reagents were quenched with Na$_2$S$_2$O$_3$ (10% aq. 100 mL) and NaHCO$_3$ (sat. aq. 200 mL). The organic phase was separated and the aqueous phase was extracted with EtOAc (3×10 mL). The combined organic extracts were dried over MgSO$_4$, filtered and concentrated under reduced pressure. The residue was purified by flash chromatography (SiO$_2$, hexanes:EtOAc=3:1→1:1) to give the desired compound as a colorless solid [447 mg, 1.30 mmol, 68%].

R$_f$=0.22 (SiO$_2$, hexanes:EtOAc=1:1); $[\alpha]_D^{23}$=+154.9 (c=1.0 in CHCl$_3$); m.p.=154-156° C.

NMR analysis of epoxide S1 revealed several conformational structures at 20° C., which increased spectrum complexity. Therefore, a variable-temperature NMR spectroscopy was employed and a full coalescence of the peaks was observed at 100° C.

$^1$H NMR (500 MHz, DMSO-d$_6$, 20° C.) δ 6.97 (d, J=1.7 Hz, 0.05H), 6.94 (s, 0.05H), 6.84 (d, J=7.9 Hz, 1H), 6.79 (d, J=4.1 Hz, 1H), 6.72-6.66 (m, 1H), 6.53 (dd, J=7.9, 1.8 Hz, 0.05H), 6.26 (dt, J=10.2, 3.7 Hz, 1H), 6.06 (td, J=7.6, 6.2, 3.7 Hz, 1H), 6.01 (d, J=1.0 Hz, 1H), 5.97 (d, J=1.1 Hz, 1H), 5.94 (dd, J=2.7, 1.0 Hz, 0.05H), 4.95 (dt, J=6.9, 3.1 Hz, 0.05H), 4.62 (br, 1H), 3.61 (d, J=1.7 Hz, 0.05H), 3.55 (dd, J=4.1, 1.0 Hz, 1H), 3.51 (td, J=4.1, 1.7 Hz, 1H), 3.44 (dd, J=4.1, 1.8 Hz, 0.05H), 3.39 (dd, J=7.3, 1.8 Hz, 0.05H), 3.35 (t, J=3.5 Hz, 0.05H), 3.22 (s, 0.05H), 3.00 (br, 3H), 2.77 (s, 0.15H), 2.64 (br, 3H).

$^1$H NMR (500 MHz, DMSO-d$_6$, 100° C.) δ 6.84-6.78 (m, 2H), 6.74 (d, J=8.0 Hz, 1H), 6.26 (dt, J=7.6, 3.4 Hz, 1H), 6.04 (d, J=9.8 Hz, 1H), 5.97 (d, J=11.8 Hz, 2H), 4.55 (d, J=11.0 Hz, 1H), 3.55 (d, J=4.2 Hz, 1H), 3.50 (d, J=4.2 Hz, 1H), 3.35 (d, J=11.0 Hz, 1H), 2.95 (s, 3H), 2.73 (d, J=2.0 Hz, 3H).

$^{13}$C NMR (126 MHz, DMSO-d$_6$, 20° C.) δ 154.8, 154.1, 147.3, 146.5, 146.3, 134.3, 134.1, 133.6, 127.3, 125.8, 121.7, 121.6, 121.4, 108.5, 108.3, 108.1, 108.0, 107.7, 100.9, 60.4, 58.0, 57.2, 56.6, 46.5, 45.4, 44.7, 41.0, 34.8, 25.1, 24.9.

$^{13}$C NMR (126 MHz, DMSO-d$_6$, 100° C.) δ 155.6, 154.9, 148.2, 147.4, 134.8, 134.4, 126.5, 122.4, 109.1, 108.7, 101.6, 58.0, 57.3, 47.4, 42.1, 34.6, 25.5.

HRMS (ESI-TOF, m/z) calcd. For $C_{17}H_{18}N_3O_5$ [M+H]$^+$ calc.: 344.1246; Found: 344.1245.

IR (ATR, neat, cm$^{-1}$): 2902 (w), 1767 (w), 1700 (s), 1484 (s), 1245 (m), 1037 (m), 932 (w), 775 (m).

22

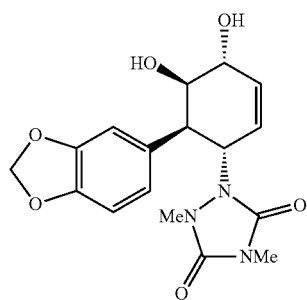

Synthesis of diol 22 from epoxide S1: To a stirred solution of epoxide S1 (816 mg, 2.38 mmol, 1.0 equiv.) in $H_2O$ (24 mL) was added NaOBz (24.0 mg, 0.17 mmol, 7.0 mol %) and the resulting mixture was then heated to 100° C. until judged complete by TLC. Upon completion, the aqueous phase was extracted with EtOAc (5×25 mL). The combined organic extracts were dried over $MgSO_4$, filtered and concentrated under reduced pressure. The residue was purified by flash chromatography ($SiO_2$, $CH_2Cl_2$:MeOH=50:1→10:1) to give the desired compound as a colorless solid [799 mg, 2.21 mmol, 93%].

$R_f$=0.32 ($SiO_2$, $CH_2Cl_2$:MeOH=9:1); $[\alpha]_D^{24}$=+87.2 (c=0.62 in EtOH); m.p.=187-188° C.

$^1$H NMR (500 MHz, $CD_3OD$) δ 7.02 (d, J=1.7 Hz, 1H), 6.78 (dd, J=8.0, 1.7 Hz, 1H), 6.67 (d, J=8.0 Hz, 1H), 6.03 (dd, J=10.2, 1.9 Hz, 1H), 5.97-5.93 (m, 1H), 5.88 (m, 2H), 5.25 (d, J=11.3 Hz, 1H), 4.03-3.99 (m, 1H), 3.87-3.83 (m, 1H), 3.35 (dd, J=11.3, 1.9 Hz, 1H), 3.17 (s, 3H), 2.69 (s, 3H).

$^{13}$C NMR (126 MHz, $CD_3OD$) δ 156.9, 156.8, 148.7, 148.2, 134.1, 132.9, 129.9, 123.9, 111.0, 108.4, 102.2, 75.9, 69.5, 57.6, 44.9, 35.1, 25.4.

HRMS (ESI-TOF, m/z) calcd. For $C_{17}H_{20}N_3O_6$ $[M+H]^+$ calc.: 362.1352; Found: 362.1352.

IR (ATR, neat, cm$^{-1}$): 3481 (m), 2902 (w), 1759 (w), 1689 (s), 1487 (s), 1251 (w), 1035 (m), 931 (w), 771 (w).

23

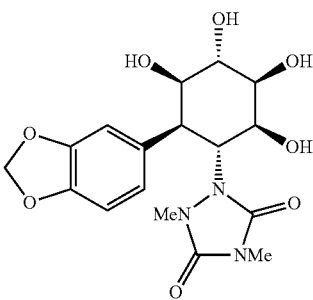

Synthesis of tetraol 23: To a stirred solution of diol 22 (7.15 g, 19.8 mmol, 1.0 equiv.) and NMO (3.48 g, 29.7 mmol, 1.5 equiv.) in tBuOH:$H_2O$ (80 mL, 1:1) at 25° C. was added $OsO_4$ (4.95 mL, 0.2 M in MeCN, 0.99 mmol, 5.0 mol %) and the resulting mixture was stirred overnight until complete conversion as judged by TLC. The reagents were quenched with excess $Na_2S_2O_3 \cdot 5H_2O$ (10 g), and the resulting solution was stirred for 30 min, and the solvent was completely removed under reduced pressure. The resulting residue was loaded onto silica and purified by flash chromatography (MeOH, $SiO_2$, $CH_2Cl_2$:MeOH=20:1→8:1) to give the desired compound as a colorless solid [7.13 g, 18.0 mmol, 91%].

$R_f$=0.28 ($SiO_2$, $CH_2Cl_2$:MeOH=8:1); $[\alpha]_D^{24}$=+22.8 (c=0.85 in EtOH); m.p.=148-150° C.

NMR analysis of tetraol 23 revealed several conformational structures at 20° C., which increased spectrum complexity. Therefore, a variable-temperature NMR spectroscopy was employed and a full coalescence of the peaks was observed at 80° C.

$^1$H NMR (500 MHz, DMSO-$d_6$, 20° C.) δ 6.98 (s, 0.2H), 6.86 (s, 0.8H), 6.79 (d, J=8.0 Hz, 0.8H), 6.74 (d, J=8.0 Hz, 0.2H), 6.70 (d, J=8.0 Hz, 0.8H), 6.67 (d, J=8.0 Hz, 0.2H), 5.94 (d, J=5.7 Hz, 1.7H), 5.92 (d, J=7.5 Hz, 0.3H), 4.77 (dd, J=12.9, 10.5 Hz, 1.0H), 4.12-4.03 (m, 0.2H), 3.98 (dd, J=10.6, 3.2 Hz, 0.8H), 3.92-3.87 (m, 1.0H), 3.87-3.81 (m, 1.0H), 3.59 (br, 1.0H), 3.40-3.31 (m, 1.0H), 3.02 (s, 2.3H), 2.92 (s, 0.7H), 2.78 (s, 2.3H), 2.73 (s, 0.7H).

$^1$H NMR (500 MHz, DMSO-$d_6$, 80° C.) δ 6.91 (s, 1H), 6.75 (d, J=8.0 Hz, 1H), 6.73 (dd, J=8.0, 1.5 Hz, 1H), 5.94-5.91 (m, 2H), 4.79 (s, 1H), 4.08 (br, 1H), 3.94 (s, 1H), 3.90 (t, J=3.3 Hz, 1H), 3.66 (s, 1H), 3.42 (br, 1H), 3.02 (s, 3H), 2.78 (s, 3H).

$^{13}$C NMR (126 MHz, DMSO-$d_6$, 20° C.) δ 156.3, 155.5, 153.3, 152.2, 146.6, 146.5, 145.7, 145.6, 133.3, 133.1, 122.6, 122.3, 109.7, 107.6, 107.4, 100.6, 75.8, 75.7, 74.3, 70.0, 68.0, 67.9, 67.3, 57.2, 56.9, 45.2, 43.4, 35.4, 31.3, 25.2, 24.5.

$^{13}$C NMR (126 MHz, DMSO-$d_6$, 80° C.) δ 146.2, 145.3, 132.8, 122.0, 109.4, 107.0, 100.1, 75.3 74.1, 69.9, 67.6, 56.9, 24.5.

HRMS (ESI-TOF, m/z) calcd. For $C_{17}H_{22}N_3O_8$ $[M+H]^+$ calc.: 396.1407; found: 396.1390.

IR (ATR, neat, cm$^{-1}$): 3396 (br), 2971 (w), 2902 (w), 1758 (w), 1689 (s), 1489 (m), 1250 (w), 1039 (m), 877 (w).

5

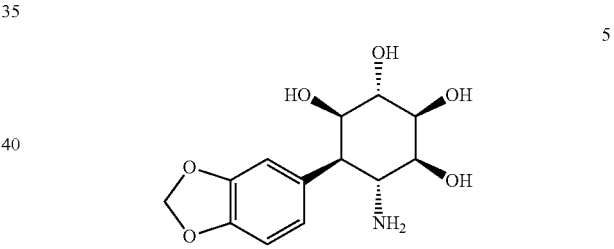

Synthesis of aminotetraol 5: To a stirred, 0° C. solution of tetraol 23 (6.83 g, 17.3 mmol, 1.0 equiv.) in THF (345 mL) under an inert atmosphere was carefully added $LiAlH_4$ (13.1 g, 345 mmol, 20 equiv.) and the resulting mixture was heated to 60° C. and stirred for 24 h. The gray suspension was cooled to 0° C., Rochelle salt (sat. aq. 345 mL) was carefully added and the resulting solution was stirred further 30 min at 25° C. To this solution was added Raney©-Co (slurry in $H_2O$, 32.0 mL) and the mixture was stirred under hydrogen atmosphere (1 atm) at 60° C. until completion as judged by TLC analysis. The mixture was filtered through a pad of Celite® and the remaining solids were further washed with $H_2O$ (3×200 mL) and MeOH (3×200 mL). The combined filtrate was concentrated and the slurry was filtered again over $SiO_2$ using MeCN: $NH_4OH$ (aq. 35%)=2:1. After removal of the solvent under reduced pressure, the resulting residue was purified by flash chromatography ($SiO_2$, $CH_2Cl_2$:MeOH:$NH_3$ (MeOH sat. sol.)=10:1:0 →6:1:0.1) to give the desired compound as a colorless solid [2.93 g, 10.3 mmol, 60%].

$R_f$=0.10 ($SiO_2$, MeCN:MeOH=9:1); $[\alpha]_D^{24}$=+29.1 (c=0.83 in EtOH); m.p.=257-259° C.

$^1$H NMR (500 MHz, CD$_3$OD) δ 6.97 (d, J=1.5 Hz, 1H), 6.83 (dd, J=8.1, 1.6 Hz, 1H), 6.78 (d, J=8.0 Hz, 1H), 5.92-5.90 (m, 2H), 4.07-4.05 (m, 1H), 3.98-3.95 (m, 1H), 3.73 (dd, J=9.9, 3.3 Hz, 1H), 3.69-3.67 (m, 1H), 3.58 (dd, J=11.5, 10.0 Hz, 1H), 2.95 (dd, J=11.6, 2.6 Hz, 1H).

$^{13}$C NMR (126 MHz, CD$_3$OD) δ 149.2, 148.0, 134.5, 123.8, 110.7, 109.0, 102.2, 76.7, 75.6, 74.4, 72.3, 50.1, 49.7.

HRMS (ESI-TOF, m/z) calcd. For C$_{13}$H$_{18}$NO$_6$ [M+H]$^+$ calc.: 284.1134; found: 284.1137.

IR (ATR, neat, cm$^{-1}$): 3348 (m), 3292 (m), 2901 (m), 1501 (m), 1487 (m), 1248 (m), 1233 (m), 1034 (s), 925 (w).

Control Experiments Showcasing that Cyclic Hydrazine 24 is an Intermediate En-Route to Amine 5

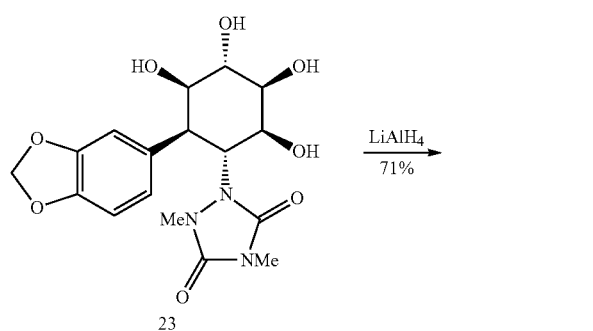

Conversion of 23→24: To a stirred, 0° C. solution of tetraol 23 (800 mg, 2.02 mmol, 1.0 equiv.) in THF (20 mL) under an inert atmosphere was carefully added LiAlH$_4$ (1.54 g, 40.5 mmol, 20 equiv.) and the resulting mixture was heated to 60° C. and stirred for 24 h. The gray suspension was cooled to 0° C., Rochelle salt (sat. aq. 20 mL) was carefully added and the solution was stirred further 30 min at 25° C. All solvents were removed under reduced pressure and the resulting residue was purified by flash chromatography (SiO$_2$, CH$_2$Cl$_2$:MeOH=20:1→8:1) to give the desired compound as a colorless solid [466 mg, 1.44 mmol, 71%]. This compound had a limited benchtop stability as noticeable decomposition (by TLC and $^1$H NMR) was observed within hours.

R$_f$=0.47 (SiO$_2$, CH$_2$Cl$_2$:MeOH=6:1); [α]$_D^{22}$=+33.4 (c=0.67 in EtOH); m.p.=143-144° C.

$^1$H NMR (500 MHz, CD$_3$OD) δ 6.92 (d, J=1.5 Hz, 1H), 6.78 (dd, J=8.0, 1.5 Hz, 1H), 6.75 (d, J=8.0 Hz, 1H), 5.91 (d, J=1.3 Hz, 1H), 5.90 (d, J=1.3 Hz, 1H), 4.48 (d, J=9.6 Hz, 1H), 4.42 (d, J=9.6 Hz, 1H), 4.10 (dd, J=11.8, 9.6 Hz, 1H), 4.06-4.04 (m, 1H), 4.02-3.98 (m, 1H), 3.72 (dd, J=9.6, 2.8 Hz, 1H), 3.71-3.69 (m, 1H), 2.93 (dd, J=11.8, 2.6 Hz, 1H), 2.62 (s, 3H).

$^{13}$C NMR (126 MHz, CD$_3$OD) δ 149.1, 148.0, 133.2, 123.6, 110.6, 109.0, 102.1, 87.1, 80.7, 77.3, 73.8, 72.4, 46.9, 46.4, 39.8.

HRMS (ESI-TOF, m/z) calcd. For C$_{15}$H$_{21}$N$_2$O$_6$ [M+H]$^+$ calc.: 325.1400; found: 325.1398.

IR (ATR, neat, cm$^{-1}$): 3306 (br), 2906 (m), 1503 (m), 1489 (s), 1443 (m), 1251 (m), 1233 (m), 1038 (s), 929 (m), 809 (m).

Conversion of 24→5: To a stirred solution of cyclic hydrazine 24 (285 mg, 0.88 mmol) in THF (10 mL) was added Raney®-Co (slurry in H$_2$O, 4.0 mL) and the mixture was stirred under hydrogen atmosphere (1 atm) at 60° C. until completion as judged by TLC analysis. The black suspension was cooled to room temperature, filtered through a pad of Celite®, and the remaining solids were further washed with H$_2$O (3×10 mL) and MeOH (3×10 mL). After removal of solvents under reduced pressure, the remaining residue was purified by flash chromatography (SiO$_2$, CH$_2$Cl$_2$:MeOH:NH$_3$ (MeOH sat. sol.)=10:1:0 →6:1:0.1) to give the desired amine as a colorless solid [195 mg, 0.69 mmol, 78%].

3-2. Synthesis of Aminoteraol 5 Via Bromohydrin 25:

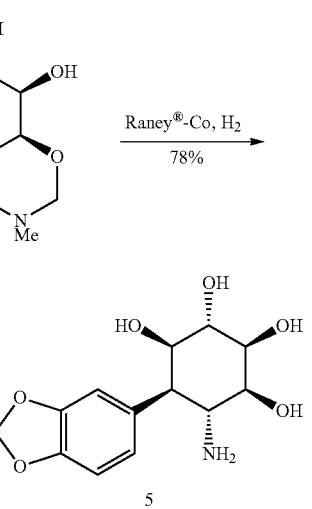

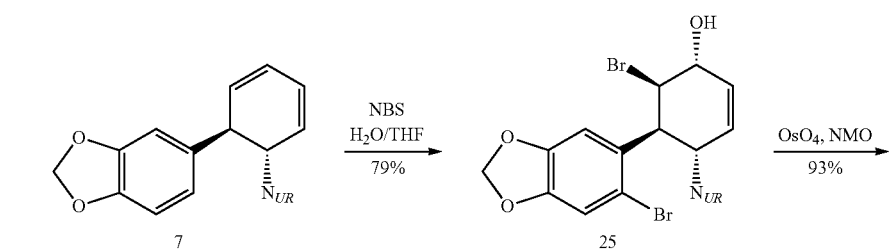

-continued

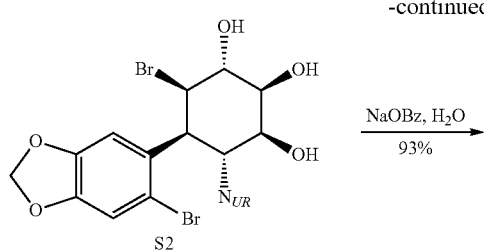 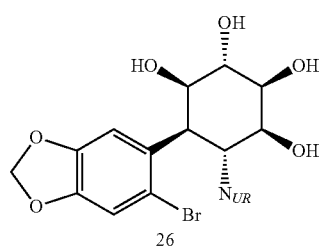

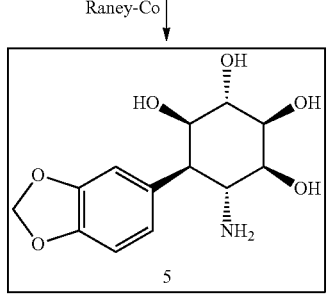

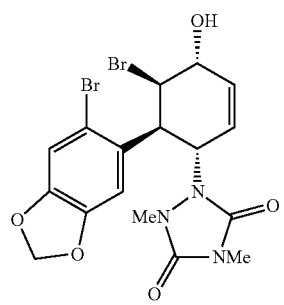

Synthesis of bromohydrin 25: To a stirred solution of (+)-diene 7 (22.5 g, 68.7 mmol, 1.00 equiv.) in THF:H$_2$O (687 mL, 1:1) at 0° C. in the absence of light was added N-bromosuccinimide (27.48 g, 154.6 mmol, 2.25 equiv.), and the resulting mixture was stirred for 6 h. Upon completion (TLC monitoring), the reagents were quenched with 10% aq. Na$_2$S2O3 (200 ml), then the resulting solution was diluted with H$_2$O (400 mL). The organic phase was separated, and the aqueous phase was extracted with CHCl$_3$ (2×600 mL). The combined organic layers were washed vigorously with sat. aq. NaHCO$_3$ (400 mL). The organic layer was dried over MgSO$_4$, filtered and concentrated under reduced pressure. The residue was purified by flash chromatography (SiO$_2$, hexanes:EtOAc=4:1→1:1) to give the desired compound as a colorless solid [27.3 g, 54.3 mmol, 79%].

R$_f$=0.44 (SiO$_2$, hexanes:EtOAc=1:3); [α]$_D^{23}$=+129.8 (c=1.0 in CHCl$_3$); m.p.=235-240° C. decomposition.

$^1$H NMR (500 MHz, CDCl$_3$) δ 7.14 (s, 1H), 7.03 (s, 1H), 6.11-6.06 (m, 1H), 5.99 (s, 2H), 5.92 (d, J=10.1 Hz, 1H), 5.30-5.10 (bs, 1H), 4.60-4.46 (m, 2H), 4.31 (s, 1H), 3.16 (s, 3H), 2.95 (s, 3H), 2.62-2.48 (bs, 1H).

$^{13}$C NMR (126 MHz, CDCl$_3$) δ 155.3, 155.2, 147.8, 147.1, 130.3, 128.8, 128.1, 115.8, 113.0, 110.0, 101.9, 69.2, 57.3, 55.6, 41.6, 34.6, 25.6.

HRMS (ESI-TOF, m/z) calcd. For C$_{17}$H$_{18}$Br$_2$N$_3$O$_5$ [M+H]$^+$ calc.: 501.9608; Found: 501.9605.

IR (ATR, neat, cm$^{-1}$): 3375 (br), 2904 (w), 1764 (m), 1694 (s), 1480 (s), 1231 (m), 1017 (m), 929 (w), 771 (w).

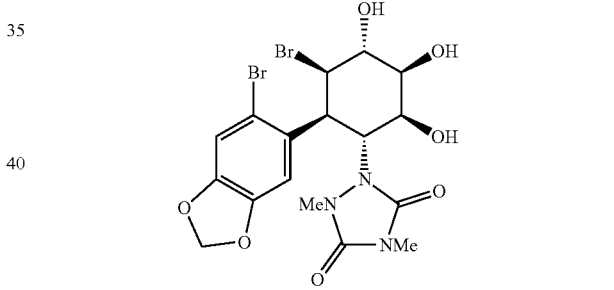

Synthesis of dibromotriol S2: To a stirred solution of (+)-bromohydrin 25 (350 mg, 0.696 mmol, 1.0 equiv.), N-methylmorpholine-N-oxide (123 mg, 1.04 mmol, 1.5 equiv.), and citric acid (292 mg, 1.39 mmol, 2.0 equiv.) in acetone:H$_2$O:tBuOH (5.6 mL, 1:1:2) at 25° C. was added OsO$_4$ (0.17 mL, 0.2 M in MeCN, 0.035 mmol, 5.0 mol %) and the resulting mixture was stirred overnight or until complete conversion as judged by TLC. The reagents were quenched with excess Na$_2$S$_2$O$_3$·5H$_2$O (10 g), the resulting solution was stirred for 30 min, and the solvent was completely removed under reduced pressure. The residue was purified by flash chromatography (SiO$_2$, CH$_2$Cl$_2$:MeOH=30:1-10:1) to give the desired compound as a colorless solid [348 mg, 0.648 mmol, 93%].

R$_f$=0.45 (SiO$_2$, CH$_2$Cl$_2$:MeOH=8:1); [α]$_D^{23}$=−93.6 (c=1.00 in CHCl$_3$); m.p.=165-167° C.

$^1$H NMR (500 MHz, DMSO-d$_6$) δ 7.18 (s, 1H), 6.90 (s, 1H), 6.05 (s, 2H), 5.97 (d, J=4.6 Hz, 1H), 5.01 (s, 1H), 4.82 (t, J=11.4 Hz, 1H), 4.76 (d, J=6.4 Hz, 1H), 4.25 (s, 1H), 4.18 (s, 1H), 4.15 (s, 1H), 4.06-4.00 (m, 2H), 3.93 (s, 1H), 2.90 (s, 3H), 2.87 (s, 3H).

$^{13}$C NMR (126 MHz, DMSO-d$_6$) δ 156.6, 155.8, 147.2, 146.4, 130.2, 114.1, 112.0, 111.0, 102.0, 73.3, 72.6, 68.3, 56.6, 54.9, 43.3, 35.4, 25.4.

HRMS (ESI-TOF, m/z) calcd. For C$_{17}$H$_{20}$N$_3$O$_7$Br$_2$ [M+H]$^+$ calcd.: 535.9668; found: 535.9674.

IR (ATR, neat, cm$^{-1}$): 3411 (br), 2910 (w), 1760 (w), 1689 (s), 1478 (s), 1400 (m), 1240 (m), 1036 (m), 729 (m).

HRMS (ESI-TOF, m/z) calcd. For C$_{17}$H$_{21}$N$_3$O$_8$Br [M+H]$^+$ calc.: 474.0512; found: 472.0516.

IR (ATR, neat, cm$^{-1}$): 3387 (br), 2907 (w), 1757 (w), 1683 (s), 1477 (s), 1401 (m), 1238 (w), 1035 (m), 845 (w).

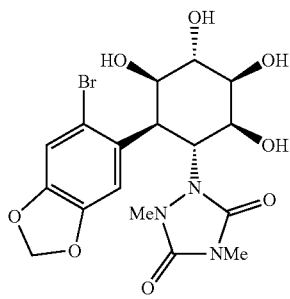

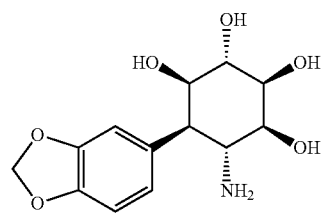

Synthesis of bromotetraol 26: To a stirred solution of dibromotriol S2 (250 mg, 0.47 mmol, 1.0 equiv.) in H$_2$O (18 mL) was added NaOBz (134 mg, 0.93 mmol, 2.0 equiv.) and the resulting mixture was then heated at 100° C. for seven days. Upon completion, the solvent was completely removed under reduced pressure. The resulting residue was loaded onto silica and purified by flash chromatography (SiO$_2$, hexanes:EtOAc=1:2→0:1) to give the desired compound as a colorless solid [100 mg, 0.21 mmol, 45%].

R$_f$ 0.30 (SiO$_2$, CH$_2$Cl$_2$:MeOH=8:1); [α]$_D^{23}$=−6.23 (c=1.00 in MeOH); m.p.=161-162° C.

$^1$H NMR (500 MHz, CD$_3$OD) δ 7.08 (s, 1H), 7.02 (s, 1H), 5.98-5.90 (m, 2H), 5.00 (dd, J=13.0, 10.5 Hz, 1H), 4.18 (dd, J=10.5, 2.5 Hz, 1H), 4.13 (dd, J=13.0, 2.7 Hz, 1H), 4.08 (d, J=2.7 Hz, 2H), 3.87 (q, J=2.5 Hz, 1H), 3.16 (s, 3H), 2.93 (s, 3H).

$^{13}$C NMR (126 MHz, CD$_3$OD) δ 158.6, 157.6, 148.6, 148.5, 131.6, 115.8, 113.3, 112.4, 103.2, 76.1, 75.3, 71.6, 70.1, 58.4, 45.4, 36.2, 25.9.

Synthesis of aminotetraol 5: To a stirred, 0° C. solution of bromotetraol 26 (2.00 g, 4.22 mmol, 1.0 equiv.) in THF (42 mL) under an inert atmosphere was carefully added LiAlH$_4$ (3.20 g, 84.34 mmol, 20 equiv.) and the resulting mixture was heated to 60° C. and stirred for 24 h. The gray suspension was cooled to 0° C., Rochelle salt (sat. aq. 42 mL) was carefully added and the resulting solution was stirred further 30 min at 25° C. To this solution was added Raney®-Co (slurry in H$_2$O, 10.3 mL) and the mixture was stirred under hydrogen atmosphere (1 atm) at 60° C. until completion as judged by TLC analysis. The mixture was filtered through a pad of Celite® and the remaining solids were further washed with H$_2$O (3×100 mL) and MeOH (3×100 mL). The combined filtrate was concentrated and the slurry was filtered again over SiO$_2$ using MeCN: NH$_4$OH (aq. 35%)=2:1. After removal of the solvent under reduced pressure, the resulting residue was purified by flash chromatography (SiO$_2$, CH$_2$Cl$_2$:MeOH:NH$_3$ (MeOH sat. sol.) =10:1:0 →6:1:0.1) to give the desired compound as a colorless solid [820 mg, 2.89 mmol, 69%]. Characterization data of this compound were in accordance with the values reported above.

3-3. Conversion of Aminotetraol 5 to (+)-7-Deoxypancratistatin (1)

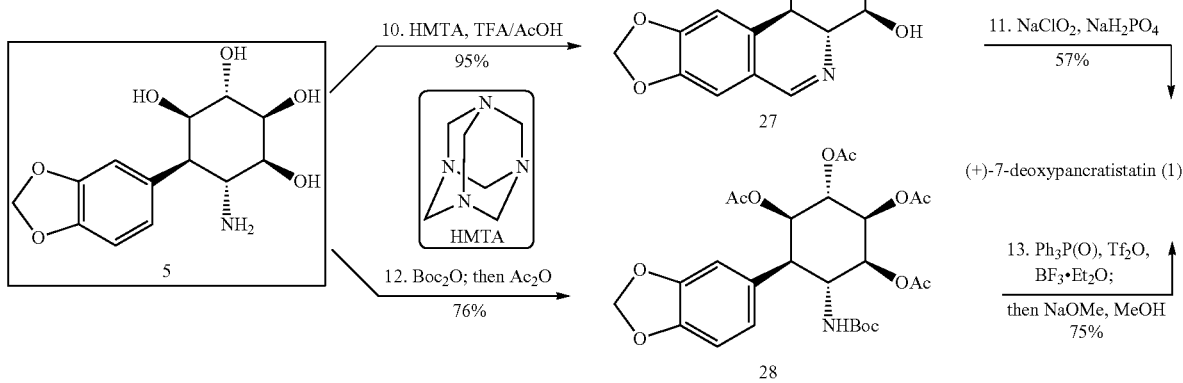

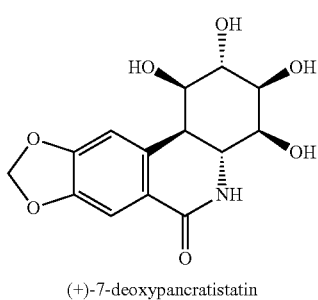

(+)-7-deoxypancratistatin

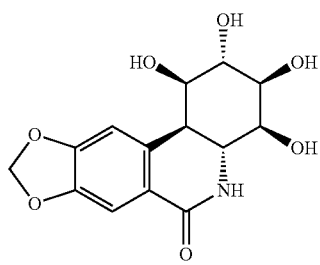

7-deoxypancratistatin

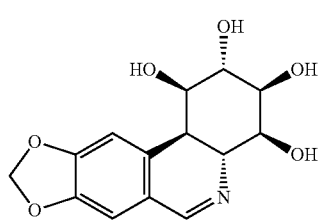

27

Synthesis of dihydroisoquinoline 27: To a stirred solution of amine 5 (100 mg, 0.35 mmol, 1.0 equiv.) in AcOH:TFA (1.2 mL, 3:1) at 25° C. was added hexamethylenetetramine (247 mg, 1.77 mmol, 5.0 equiv.) and the resulting mixture was heated to 90° C. and stirred overnight until complete conversion as judged by TLC. The reaction mixture was concentrated under reduced pressure and dissolved in MeOH (10 mL) and NaHCO$_3$ (2.50 g) was carefully added. The reaction mixture was then loaded onto Celite© and purified by flash chromatography (Cis functionalized SiO$_2$, H$_2$O:MeOH=5:1→3:1, and then SiO$_2$, CH$_2$Cl$_2$:MeOH=20:1→6:1) to give the desired compound as a colorless solid [98.0 mg, 0.33 mmol, 95%].

$R_f$=0.45 (SiO$_2$, CH$_2$Cl$_2$:MeOH:NH$_3$ (MeOH sat. sol.)=6:1:0.1); $[\alpha]_D^{23}$=−7.0 (c=0.62 in DMF); m.p.=222-224° C. decomposition.

$^1$H NMR (500 MHz, DMSO-d$_6$) δ 8.20 (d, J=3.1 Hz, 1H), 7.04 (s, 1H), 6.91 (s, 1H), 6.05 (s, 2H), 5.34-4.58 (br, 4H), 4.34 (s, 1H), 4.03-3.84 (m, 2H), 3.76 (dd, J=10.3, 2.9 Hz, 1H), 3.28 (d, J=15.7 Hz, 1H), 2.73 (dd, J=15.7, 2.6 Hz, 1H).

$^{13}$C NMR (126 MHz, DMSO-d$_6$) δ 158.2, 149.3, 145.5, 132.7, 123.5, 107.3, 105.7, 101.3, 74.2, 70.9, 70.0, 69.3, 55.9, 37.0.

HRMS (ESI-TOF, m/z) calcd. For C$_{14}$H$_{16}$NO$_6$ [M+H]$^+$ calc.: 294.0978; found: 294.0977.

IR (ATR, neat, cm$^{-1}$): 3280 (br), 2916 (w), 1656 (m), 1593 (m), 1485 (m), 1373 (m), 1264 (s), 1034 (s), 935 (m).

Synthesis of (+)-7-deoxypancratistatin (1) from dihydroisoquinoline 27: To a stirred solution of dihydroisoquinoline 27 (20.0 mg, 0.068 mmol, 1.0 equiv.) in THF (0.68 mL) and 2-methyl-2-butene (0.72 mL, 6.82 mmol, 100 equiv.) at 0° C. was added NaClO$_2$ (308 mg, 80% w/w, 2.73 mmol, 40 equiv.) and NaH$_2$PO$_4$.2H$_2$O (425 mg, 2.73 mmol, 40 equiv.) as a solution in H$_2$O (0.27 mL) dropwise. The reaction was allowed to warm to 25° C. and was stirred until completion (TLC monitoring). If full conversion was not observed after 24 hours, another 20 equiv. of NaClO$_2$ and NaH$_2$PO$_4$.2H$_2$O would need to be added to drive the reaction to completion. Upon completion, the reagents were quenched with Na$_2$S$_2$O$_3$·5H$_2$O before the resulting solution was loaded onto silica gel and purified by flash chromatography (Cis functionalized SiO$_2$, H$_2$O:MeOH=5:1→3:1, and then SiO$_2$, CH$_2$Cl$_2$:MeOH=9:1→6:1) to give (+)-7-deoxypancratistatin (1) as a colorless solid [12.0 mg, 0.039 mmol, 57%]. Characterization data of this compound were in accordance with the literature values.

$R_f$=0.30 (SiO$_2$, CHCl$_3$:MeOH=4:1); $[\alpha]_D^{24}$=+75.5 (c=0.75 in DMF); Reported values: lit. $[\alpha]_D^{25}$=+78.5 (c=0.75 in DMF) (Acta Cryst. 2015, A71, 3); lit. $[\alpha]_D^{23}$=+72.7 (c=2.3 in DMF) (Acta Cryst. 2008, A64, 112); m.p.=310-312° C.

$^1$H NMR (500 MHz, DMSO-d$_6$) δ 7.32 (s, 1H), 6.91 (s, 1H), 6.84 (s, 1H), 6.07 (s, 2H), 5.36 (d, J=3.9 Hz, 1H), 5.07 (d, J=5.7 Hz, 1H), 5.05 (d, J=6.0 Hz, 1H), 4.78 (d, J=7.5 Hz, 1H), 4.37-4.29 (m, 1H), 3.98 (q, J=3.4 Hz, 1H), 3.91-3.83 (m, 1H), 3.79-3.66 (m, 2H), 2.99 (dd, J=12.0, 2.0 Hz, 1H).

$^{13}$C NMR (126 MHz, DMSO-d$_6$) δ 164.0, 150.5, 145.8, 135.3, 123.8, 106.7, 105.5, 101.5, 73.4, 70.3, 70.2, 68.7, 50.4, 40.1, (39.8 observed by HSQC).

HRMS (ESI-TOF, m/z) calcd. For C$_{14}$H$_{16}$NO$_7$ [M+H]$^+$ calc.: 310.0927; found: 310.0925.

IR (ATR, neat, cm$^{-1}$): 3347 (br), 2923 (w), 1650 (s), 1505 (w), 1469 (s), 1267 (m), 1203 (m), 1039 (s).

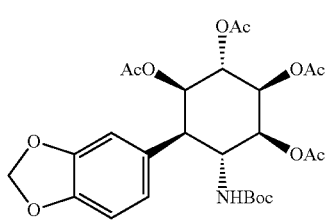

28

Synthesis of protected aminotetraol 28: To a stirred solution of amine 5 (1.20 g, 4.24 mmol, 1.0 equiv.) in dioxane:H$_2$O (42 mL, 1:1) at 25° C. was added Et$_3$N (1.80 mL, 12.7 mmol, 3.0 equiv.) and Boc$_2$O (1.39 g, 6.35 mmol, 1.5 equiv.) and the reaction was stirred overnight at 25° C. until complete conversion as judged by TLC. Upon completion, the reaction was concentrated under reduced pressure and complete removal of water was achieved with azeotropic distillation using acetonitrile (3×2 mL). The crude residue was then suspended in CH$_2$Cl$_2$ (42 mL) and Et$_3$N (2.90 mL, 21.2 mmol, 5.0 equiv.), DMAP (51.8 mg, 0.42 mmol, 10 mol %) and Ac$_2$O (1.80 mL, 19.1 mmol, 4.5 equiv.) were added. The reaction was stirred at 25° C. until complete conversion as judged by TLC. Upon completion, the reagents were carefully quenched with NaHCO$_3$ and the resulting solution was stirred vigorously for 30 min. The phases were separated, and the aqueous phase was extracted with CH$_2$Cl$_2$ (3×20 mL). The combined organics were washed with aq. HCl (20 mL, 1M) and brine (20 mL), dried over MgSO$_4$, filtered, and concentrated. The resulting residue was loaded onto silica and purified by flash chromatography (SiO$_2$, hexanes:EtOAc=3:1→1:1) to give the desired compound as a colorless solid [1.78 g, 3.22 mmol, 76%].

R$_f$ 0.38 (SiO$_2$, hexanes:EtOAc=1:1); [α]$_D^{23}$=+20.6 (c=1.00 in CHCl$_3$); m.p.=60-62° C.

$^1$H NMR (500 MHz, CDCl$_3$) δ 6.77 (s, 1H), 6.71 (s, 2H), 5.91 (dd, J=13.9, 1.5 Hz, 2H), 5.33 (d, J=3.5 Hz, 1H), 5.17 (dd, J=10.5, 3.5 Hz, 1H), 5.10 (t, J=3.0 Hz, 1H), 5.00 (td, J=3.0, 1.5 Hz, 1H), 4.70 (q, J=11.1 Hz, 1H), 4.16 (d, J=10.5 Hz, 1H), 3.19-2.99 (m, 1H), 2.17 (s, 3H), 2.16 (s, 3H), 2.02 (s, 3H), 1.97 (s, 3H), 1.29 (s, 9H).

$^{13}$C NMR (126 MHz, CDCl$_3$) δ 170.7, 169.6, 169.1, 168.4, 155.5, 147.8, 147.0, 129.9, 122.4, 109.4, 108.2, 101.1, 79.6, 72.3, 71.3, 68.9, 68.3, 47.6, 47.2, 28.2, 21.0*, 20.9, 20.8. (* Overlap of 2 peaks).

HRMS (ESI-TOF, m/z) calcd. For C$_{26}$H$_{34}$NO$_{12}$ [M+H]$^+$ calc.: 552.2081; found: 552.2062.

IR (ATR, neat, cm$^{-1}$): 3370 (w), 2977 (w), 1743 (s), 1712 (s), 1505 (m), 1492 (m), 1219 (s), 1039 (s), 730 (s).

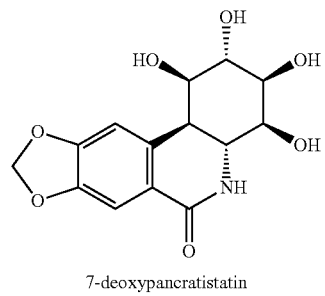

(1)

7-deoxypancratistatin

Synthesis of (+)-7-deoxypancratistatin (1) from protected amine 28: To a stirred solution of PPh$_3$O (2.15 g, 7.72 mmol, 2.4 equiv.) in CH$_2$Cl$_2$ (54 mL) at 0° C. under nitrogen atmosphere was added Tf$_2$O (3.86 mL, 1.0 M in CH$_2$Cl$_2$, 3.86 mmol, 1.2 equiv.) dropwise. The reaction was stirred 30 min at the same temperature before the 7-deoxypancratistatin (1) addition of protected amine 28 (1.78 g, 3.22 mmol, 1.0 equiv.) in CH$_2$Cl$_2$ (54 mL) dropwise. The mixture was stirred 15 min before the addition of BF$_3$·OEt$_2$ (2.04 mL, 16.1 mmol, 5.0 equiv.). The reaction was stirred for 15 min before warming to 25° C., then stirred another 45 min before CH$_2$Cl$_2$ (20 mL) was added and reagents were carefully quenched with sat. aq. NaHCO$_3$ (20 mL). The phases were separated and the aqueous phase was extracted with CH$_2$Cl$_2$ (3×20 mL). The combined organics were washed with brine (20 mL), dried over MgSO$_4$, filtered, and concentrated. The crude residue was then taken up in MeOH (32 mL) and NaOMe (3.58 mL, 25% w/w in MeOH, 16.1 mmol, 5.0 equiv.) was added. The reaction was stirred until completion by TLC before cooling to 0° C. and carefully neutralizing with HCl (1.34 mL, 12M), loading onto Celite® purification by flash chromatography (Cis functionalized SiO$_2$, H$_2$O:MeOH=5:1→3:1, and then SiO$_2$, CH$_2$Cl$_2$:MeOH=9:1→6:1) to give (+)-7-deoxypancratistatin (1) as a colorless solid [743 mg, 2.40 mmol, 75% overall]. Characterization data of this compound were in accordance with the values reported above.

Example 4. First Generation Approach to (+)-Pancratistatin (2)

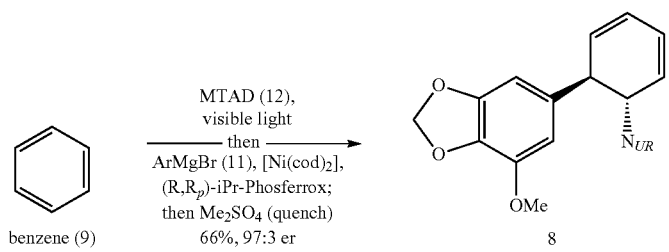

-continued

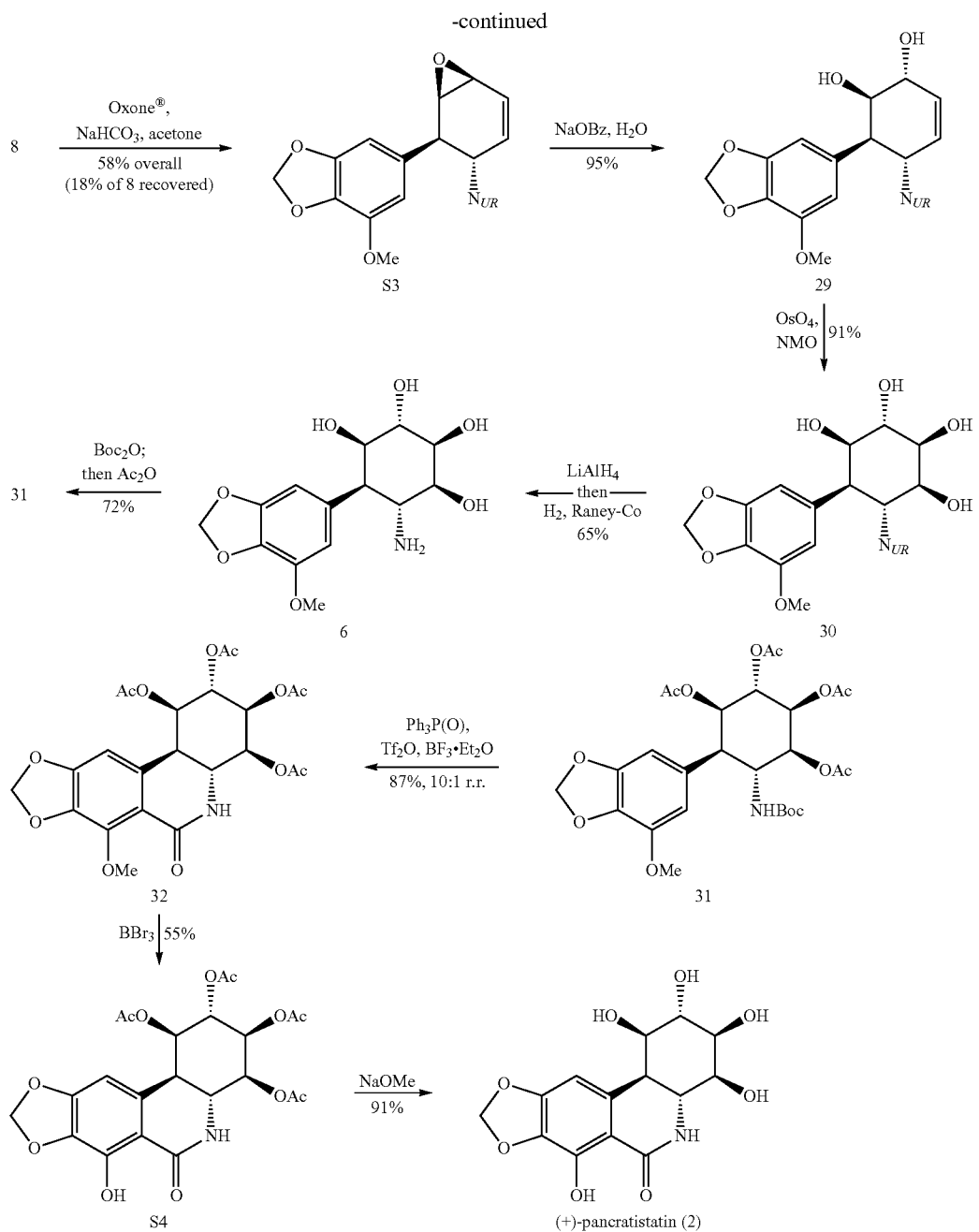

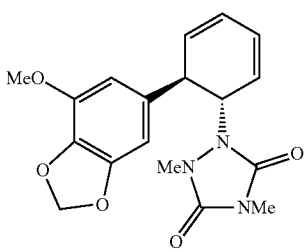

Synthesis of diene 8: (+)-Diene 8 was prepared using the procedure to synthesize (+)-diene 7, employing the Grignard reagent derived from 3,4-methylenedioxy-5-methoxy-phenyl bromide 11 (synthesized according to literature procedure: J. Am. Chem. Soc. 1998, 120, 5341). The reaction was run on 53 mmol scale, with MTAD (6.00 g) as the limiting reagent. The residue was purified by flash chromatography ($SiO_2$, hexanes:EtOAc=5:1→3:1) to give the desired compound as a colorless solid [11.39 g, 34.8 mmol, 66%, 97:3 er].

Enantiomeric ratio was determined with HPLC analysis using Daicel Chiracel© OJ-H column, 50% iPrOH in hexanes, 0.8 mL/min, $t_R$(minor)=12.4 min, $t_R$(major)=19.6 min.

$R_f$=0.35 ($SiO_2$, hexanes:EtOAc=1:1); $[\alpha]_D^{24}$=+217.2 (c=1.0 in $CHCl_3$); m.p.=117-121° C.

¹H NMR (500 MHz, CDCl₃) δ 6.46 (d, J=1.5 Hz, 1H), 6.38 (d, J=1.5 Hz, 1H), 6.15-6.10 (m, 1H), 6.06 (ddd, J=8.4, 5.3, 2.7 Hz, 1H), 5.94 (d, J=1.6 Hz, 1H), 5.93 (d, J=1.6 Hz, 1H), 5.85 (dd, J=9.6, 3.1 Hz, 1H), 5.69 (dd, J=9.6, 3.3 Hz, 1H), 5.16 (dt, J=13.7, 3.1 Hz, 1H), 3.92-3.86 (m, 1H), 3.85 (s, 3H), 3.20 (s, 3H), 2.91 (s, 3H).

¹³C NMR (126 MHz, CDCl₃) δ 156.2, 155.1, 149.1, 143.5, 136.1, 134.6, 130.8, 126.5, 125.7, 123.5, 107.6, 102.4, 101.6, 61.0, 56.7, 45.1, 35.2, 25.5.

HRMS (ESI-TOF, m/z) calcd. For C₁₈H₁₉N₃O₅Na [M+Na]⁺ calc.: 380.1222; Found: 380.1218.

IR (ATR, neat, cm⁻¹): 2928 (m), 2244 (w), 1766 (w), 1706 (s), 1451 (m), 1093 (m), 963 (m), 723 (m).

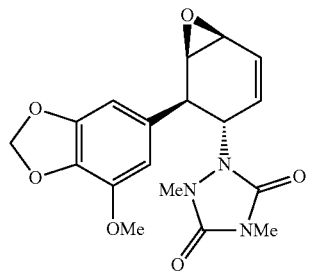

S3

Synthesis of epoxide S3: To a vigorously stirred solution of diene 8 (3.00 g, 8.39 mmol, 1.0 equiv.) and EDTA (31.2 mg, 83.9 μmol, 1.0 mol %) in a mixture of acetone, CH₂Cl₂, and sat. aq. NaHCO₃ (118 mL 1:10:20) was dropwise added Oxone© (10.3 g, 16.8 mmol. 2.0 equiv.) in water (46 mL) at 0° C. The reaction was stirred at 0° C. for 30 minutes then was allowed to warm to 25° C. and stir for 8 hours. Then another aliquot of Oxone© (10.3 g, 16.8 mmol. 2.0 equiv.) in water (46 mL) at 0° C. and the reaction was stirred at 0° C. for another 30 minutes then was allowed to warm to 25° C. over 8 hours. The organic phase was separated and the aqueous phase was extracted with CH₂Cl₂ (3×200 mL). The combined organic extracts were dried over MgSO₄, filtered and concentrated under reduced pressure. The residue was purified by flash chromatography (SiO₂, hexanes:EtOAc=4:1→1:1) to give the desired compound as a colorless solid [1.82 g, 4.88 mmol, 58%] as well as recovered starting material 8 [0.54 g, 1.52 mmol, 18%].

$R_f$=0.37 (SiO₂, hexanes:EtOAc=1:3); $[\alpha]_D^{23}$=+139.5 (c=1.0 in CHCl₃); m.p.=68-70° C.

NMR analysis of epoxide S3 revealed several conformational structures at 20° C., which increased spectrum complexity. Unfortunately, when variable-temperature NMR spectroscopy was employed full coalescence of the peaks was not observed.

¹H NMR (500 MHz, DMSO-d₆, 100° C.) δ 6.54-6.50 (m, 2H), 6.50-6.49 (m, 0.8H), 6.28-6.24 (m, 1.4 H), 6.06-6.02 (m, 1.4 H), 5.96 (s, 1H), 5.95 (s, 0.4H), 5.94 (s, 1H), 5.92 (s, 0.4H), 4.66 (d, J=10.9 Hz, 0.4H), 4.57 (d, J=11.0 Hz, 1H), 3.81 (s, 3H), 3.80 (s, 1.2H), 3.59 (t, J=3.5 Hz, 0.4H), 3.56 (d, J=4.2 Hz, 1H), 3.51-3.48 (m, 1H), 3.45 (d, J=4.6 Hz, 0.4H), 3.32 (d, J=11.1 Hz, 1H), 3.26 (d, J=4.3 Hz, 0.4H), 3.20 (s, 1.2 H), 2.97 (s, 3. H), 2.74 (s, 3H), 2.67 (s, 1.2H).

¹³C NMR (126 MHz, DMSO-d₆, 100° C.) δ 155.0, 154.5, 154.0, 153.7, 148.3, 148.1, 142.7, 142.5, 134.1, 134.0, 133.8*, 125.3, 119.1 108.5, 108.4, 101.8, 101.7, 100.7*, 56.8, 56.2, 56.1, 55.9, 55.7, 54.7, 51.8, 49.4, 46.2, 41.2, 24.5, 24.4. (*Overlap of 2 peaks) HRMS (ESI-TOF, m/z) calcd. For C₁₈H₂₀N₃O₆ [M+H]⁺ calc.: 374.1352; Found: 374.1361.

IR (ATR, neat, cm⁻¹): 2902 (w), 1765 (w), 1698 (s), 1450 (s), 1234 (m), 1040 (m), 926 (w), 775 (m).

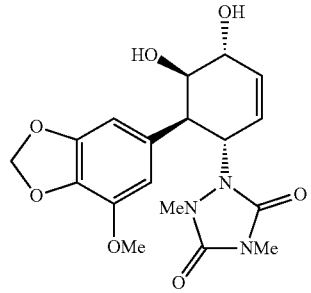

29

Synthesis of diol 29: Diol 29 was prepared using the procedure to synthesize diol 22. Epoxide S3 (1.70 g, 4.55 mmol) was subjected to the reaction conditions. The residue was purified by flash chromatography (SiO₂, CH₂Cl₂:MeOH=50:1→20:1) to give the desired compound as a colorless solid [1.69 g, 4.32 mmol, 95%].

$R_f$=0.40 (SiO₂, CH₂Cl₂:MeOH=8:1); $[\alpha]_D^{23}$=+102.4 (c=1.0 in CHCl₃); m.p.=173-176° C.

¹H NMR (500 MHz, CD₃OD) δ 6.65 (d, J=1.5 Hz, 1H), 6.62 (d, J=1.5 Hz, 1H), 6.03 (dd, J=10.0, 1.9 Hz, 1H), 5.95 (ddd, J=10.0, 4.5, 2.6 Hz, 1H), 5.87 (s, 2H), 5.25 (d, J=11.0 Hz, 1H), 4.02 (ddd, J=4.5, 2.6, 1.3 Hz, 1H), 3.87 (dd, J=3.0, 1.3 Hz, 1H), 3.83 (s, 3H), 3.33 (s, 1H), 3.17 (s, 3H), 2.71 (s, 3H).

¹³C NMR (126 MHz, CD₃OD) δ 157.0, 156.9, 149.9, 144.3, 135.7, 134.7, 132.9, 129.8, 110.4, 104.6, 102.4, 75.9, 69.5, 57.6, 57.0, 45.2, 35.1, 25.4.

HRMS (ESI-TOF, m/z) calcd. For C₁₈H₂₁N₃O₇Na [M+Na]⁺ calc.: 414.1277; Found: 414.1287.

IR (ATR, neat, cm⁻¹): 3399 (br), 2911 (w), 1747 (w), 1682 (s), 1495 (m), 1452 (m), 1044 (m).

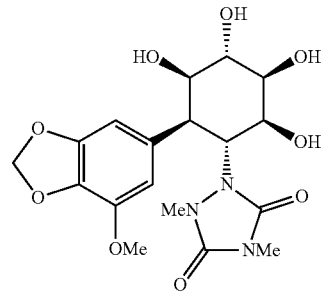

30

Synthesis of tetraol 30: Tetraol 30 was prepared using the procedure to synthesize tetraol 23. Diol 29 (1.50 g, 3.83 mmol) was subjected to the reaction conditions. The residue was purified by flash chromatography (SiO₂, CH₂Cl₂:MeOH=20:1→8:1) to give the desired compound as a colorless solid [1.48 g, 3.48 mmol, 91%].

$R_f$=0.23 (SiO₂, CH₂Cl₂:MeOH=8:1); $[\alpha]_D^{24}$=+19.3 (c=1.0 in MeOH); m.p.=134-138° C.

NMR analysis of tetraol 30 revealed several conformational structures at 20° C., which increased spectrum complexity. Therefore, a variable-temperature NMR spectroscopy was employed and a full coalescence of the peaks was observed at 100° C.

$^1$H NMR (500 MHz, DMSO-d$_6$, 20° C.) δ 6.60 (s, 0.25H), 6.57-6.54 (m, 1H), 6.53 (s, 1.25H), 5.95-5.87 (m, 2.5H), 5.41 (d, J=3.7 Hz, 1H), 5.34-5.28 (m, 1.25H), 5.24 (d, J=5.3 Hz, 0.25H), 4.96 (d, J=7.4 Hz, 0.25H), 4.92 (d, J=7.7 Hz, 1H), 4.82-4.70 (m, 2.25H), 4.35 (ddd, J=9.9, 6.5, 3.0 Hz, 0.25H), 4.07 (t, J=11.2 Hz, 0.25H), 4.00 (ddd, J=10.2, 6.7, 3.1 Hz, 1H), 3.93-3.84 (m, 2.5H), 3.78 (s, 3H), 3.75 (s, 0.75H), 3.69-3.61 (m, 1H), 3.37 (s, 1H), 3.04 (s, 3H), 2.94 (s, 0.75H), 2.79 (s, 3H), 2.75 (s, 0.75H).

$^1$H NMR (500 MHz, DMSO-d$_6$, 100° C.) δ 6.57 (s, 2H), 5.89 (s, 2H), 5.07 (s, 1H), 4.94 (s, 1H), 4.73 (s, 1H), 4.28 (s, 1H), 4.15 (s, 1H), 3.97 (s, 1H), 3.93 (d, J=3.4 Hz, 1H), 3.81 (s, 3H), 3.71 (s, 1H), 3.49 (br, 1H), 3.04 (s, 3H), 2.98 (s, 1H), 2.79 (s, 3H).

$^{13}$C NMR (126 MHz, DMSO-d$_6$, 20° C.) δ 156.2, 155.5, 153.3, 152.2, 147.8, 147.7, 142.6, 142.3, 133.9*, 133.4, 133.2, 109.1, 108.8, 103.4, 103.2, 100.8*, 75.7, 75.2, 74.6, 74.4, 70.6, 70.2, 67.9, 67.5, 57.3, 56.9, 56.2*, 45.5, 43.7, 35.4, 31.2, 25.2, 24.5. (* Overlap of 2 peaks) $^{13}$C NMR (126 MHz, DMSO-d$_6$, 100° C.) δ 147.5, 142.2, 133.3, 133.2, 109.6, 103.0, 100.2, 75.2, 74.1, 70.0, 67.7, 56.9, 56.1, 24.3.

HRMS (ESI-TOF, m/z) calcd. For $C_{18}H_{24}N_3O_9$ [M+H]$^+$ calc.: 426.1513; found: 426.1510.

IR (ATR, neat, cm$^{-1}$): 3378 (br), 2910 (w), 1757 (w), 1686 (s), 1487 (m), 1244 (w), 1041 (m), 771 (w).

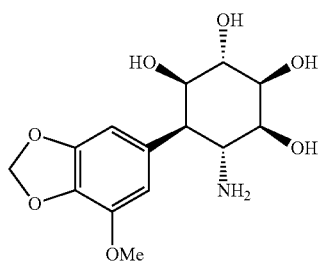

6

Synthesis of amine 6: Amine 6 was prepared using the procedure to synthesize amine 5. Tetraol 30 (1.40 g, 3.54 mmol) was subjected to the reaction conditions. The residue was purified by flash chromatography (SiO$_2$, CH$_2$Cl$_2$: MeOH=10:1→4:1) to give the desired compound as a yellow solid [652 mg, 2.30 mmol, 65%].

$R_f$=0.15 (SiO$_2$, CH$_2$Cl$_2$:NH$_3$ (MeOH sat. sol.)=4:1); [α]$_D^{23}$=+18.9 (c=0.5 in MeOH); m.p.=248-252° C.

$^1$H NMR (500 MHz, CD$_3$OD) δ 6.68 (s, 1H), 6.66 (s, 1H), 6.01-5.85 (m, 2H), 4.09 (t, J=3.2 Hz, 1H), 4.05-4.01 (m, 1H), 3.95 (dd, J=10.3, 3.2 Hz, 1H), 3.91 (s, 3H), 3.81 (dd, J=12.0, 10.3 Hz, 1H), 3.78-3.75 (m, 1H), 3.17 (dd, J=12.0, 2.5 Hz, 1H).

$^{13}$C NMR (126 MHz, CD$_3$OD) 150.8, 145.2, 136.5, 132.1, 110.9, 104.5, 102.7, 76.2, 75.1, 71.7, 71.1, 57.3, 52.8, 47.2.

HRMS (ESI-TOF, m/z) calcd. For $C_{14}H_{20}NO_7$ [M+H]$^+$ calc.: 314.1240; Found: 314.1237.

IR (ATR, neat, cm$^{-1}$): 3231 (br), 2906 (br), 1634 (w), 1512 (m), 1435 (s), 1256 (m), 1075 (s), 1038 (s).

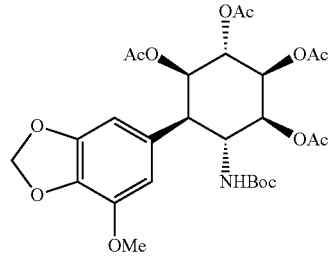

31

Synthesis of protected amine 31: Protected amine 31 was prepared using the procedure to synthesize protected amine 28. Amine 6 (600 mg, 2.12 mmol) was subjected to the reaction conditions. The residue was purified by flash chromatography (SiO$_2$, hexanes:EtOAc=3:1→1:1) to give the desired compound as a colorless solid [844 mg, 1.53 mmol, 72%].

$R_f$=0.34 (SiO$_2$, hexanes:EtOAc=1:1); [α]$_D^{23}$=+19.5 (c=1.0 in CHCl$_3$); m.p.=110-116° C.

$^1$H NMR (500 MHz, CDCl$_3$) δ 6.46 (s, 1H), 6.40 (s, 1H), 5.90 (s, 1H), 5.87 (s, 1H), 5.30 (d, J=3.6 Hz, 1H), 5.13 (dd, J=10.4, 3.6 Hz, 1H), 5.06 (t, J=2.9 Hz, 1H), 4.98 (d, J=2.9 Hz, 1H), 4.68 (q, J=11.1 Hz, 1H), 4.28 (d, J=10.4 Hz, 1H), 3.84 (s, 3H), 3.11 (dd, J=11.1, 3.0 Hz, 1H), 2.13 (s, 6H), 1.98 (s, 3H), 1.93 (s, 3H), 1.27 (s, 9H).

$^{13}$C NMR (126 MHz, CDCl$_3$) δ 170.5, 169.4, 168.8, 168.3, 155.5, 148.7, 143.3, 134.4, 130.4, 108.0, 103.1, 101.4, 79.5, 72.1, 71.1, 68.6, 68.0, 56.4, 47.5, 47.0, 28.1, 20.9, 20.8, 20.6, 20.5.

HRMS (ESI-TOF, m/z) calcd. For $C_{27}H_{36}NO_{13}$ [M+H]$^+$ calc.: 582.2187; Found: 582.2161.

IR (ATR, neat, cm$^{-1}$): 2977 (w), 1744 (s), 1711 (m), 1367 (m), 1219 (s), 1041 (s), 927 (m).

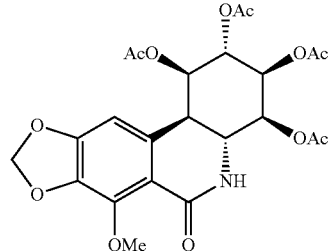

32

Synthesis of (+)-7-methoxy-pancratistatin tetraacetate 32: To a OAc stirred solution of PPh$_3$O (861 mg, 3.10 mmol, 2.4 equiv.) in CH$_2$Cl$_2$ (21 mL) at 0° C. under nitrogen atmosphere was added Tf$_2$O (1.55 mL, 1.0 M in CH$_2$Cl$_2$, 1.55 mmol, 1.2 equiv.) dropwise. The reaction was stirred 30 min at the same temperature before the addition of 32 protected amine 31 (750 mg, 1.29 mmol, 1.0 equiv.) in CH$_2$Cl$_2$ (21 mL) dropwise. The mixture was stirred 15 min before the addition of BF$_3$·OEt$_2$ (0.82 mL, 6.45 mmol, 5.0 equiv.). The reaction was stirred for 15 min before warming to 25° C., then stirred another 45 min before CH$_2$Cl$_2$ (20 mL) was added and reagents were carefully quenched with sat. aq. NaHCO$_3$ (20 mL). The phases were separated and the aqueous phase was extracted with CH$_2$Cl$_2$ (3×20 mL). The combined organics were washed with brine (20 mL), dried over MgSO$_4$, filtered, and concentrated. The residue was purified by flash chromatography (SiO$_2$, hexanes:EtOAc=3:

1→1:3) to give the desired compound as a mixture of constitutional isomers [569 mg, 1.12 mmol, 87%, 10:1 r.r]. Characterization data of (+)-7-methoxy-pancratistatin tetraacetate 32 were in accordance with the literature values (J. Am. Chem. Soc. 1998, 120, 5341).

$R_f$=0.38 (SiO$_2$, CH$_2$Cl$_2$:MeOH=16:1); $[\alpha]_D^{23}$=+77.8 (c=0.5 in MeOH).

For clarity, only the major constitutional isomer is described.

$^1$H NMR (500 MHz, CDCl$_3$) δ 6.30 (s, 1H), 6.03 (d, J=1.4 Hz, 1H), 5.98 (d, J=1.4 Hz, 1H), 5.93 (s, 1H), 5.52 (d, J=3.0 Hz, 1H), 5.45 (t, J=3.2 Hz, 1H), 5.22 (t, J=3.0 Hz, 1H), 5.13 (dd, J=10.8, 3.2 Hz, 1H), 4.18 (dd, J=12.8, 10.8 Hz, 1H), 4.09-4.04 (m, 3H), 3.37 (dd, J=12.8, 2.9 Hz, 1H), 2.16 (s, 3H), 2.07 (s, 6H), 2.03 (s, 3H).

$^{13}$C NMR (126 MHz, CDCl$_3$) δ 170.2, 169.7, 169.2, 168.4, 163.5, 152.6, 145.6, 137.7, 133.4, 115.9, 102.0, 99.1, 71.8, 67.8, 67.0, 66.7, 61.0, 47.7, 40.5, 21.0, 20.9, 20.8, 20.7.

HRMS (ESI-TOF, m/z) calcd. For C$_{23}$H$_{26}$NO$_{12}$ [M+H]$^+$ calc.: 508.1455; Found: 508.1457.

IR (ATR, neat, cm$^{-1}$): 2923 (w), 1744 (s), 1667 (s), 1651 (w), 1481 (s), 1369 (m) 1212 (s), 1038 (s), 728 (w).

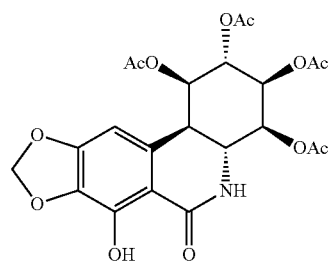

Synthesis of (+)-pancratistatin tetraacetate S4: (+)-pancratistatin tetraacetate S4 was prepared according to literature procedure (J. Am. Chem. Soc. 1998, 120, 5341). To the mixture of constitutional isomers 32 (500 mg, 985 µmol, 1.0 equiv.) in CH$_2$Cl$_2$ (49 mL) was added BBr$_3$ (985 µL, 985 µmol, 1.0 equiv.) at −78° C. The reaction mixture was then warmed to 0° C. and stirred for 30 min. Then, 10% aq. NH$_4$OH (20 mL) was added at 0° C. and stirred for 20 mins. The phases were separated and the aqueous phase was extracted with CH$_2$Cl$_2$ (5×100 mL). The combined organics were washed with brine (100 mL) and water (100 mL), dried over MgSO$_4$, filtered, and concentrated. The residue was purified by flash chromatography (SiO$_2$, hexanes:EtOAc=3: 1→1:3) to give the desired compound as a colorless solid [269 mg, 541 µmol, 55%]. Characterization data of (+)-pancratistatin tetraacetate S4 were in accordance with the literature values (J. Am. Chem. Soc. 1998, 120, 5341).

$R_f$=0.32 (SiO$_2$, hexanes:EtOAc=1:1); $[\alpha]_D^{23}$=+32.8 (c=1.0 in CHCl$_3$); m.p.=239-242° C.

$^1$H NMR (500 MHz, CDCl$_3$) δ 12.37 (s, 1H), 6.22-6.17 (m, 1H), 6.13 (s, 1H), 6.05-6.03 (m, 1H), 5.55 (d, J=2.9 Hz, 1H), 5.46 (t, J=3.4 Hz, 1H), 5.22 (t, J=2.9 Hz, 1H), 5.17 (dd, J=10.8, 3.4 Hz, 1H), 4.28 (dd, J=13.2, 10.8 Hz, 1H), 3.48-3.38 (m, 1H), 2.16 (s, 3H), 2.09 (s, 6H), 2.04 (s, 3H).

$^{13}$C NMR (126 MHz, CDCl$_3$) δ 170.1, 170.0, 169.7, 169.2, 168.4, 153.4, 146.9, 133.6, 131.8, 107.4, 102.6, 96.7, 71.8, 67.8, 67.0, 66.3, 48.4, 39.4, 21.0, 20.9, 20.8, 20.7.

HRMS (ESI-TOF, m/z) calcd. For C$_{22}$H$_{24}$NO$_{12}$ [M+H]$^+$ calc.: 494.1299; Found: 494.1293.

IR (ATR, neat, cm$^{-1}$): 3351 (br), 2915 (w), 1741 (s), 1668 (w), 1370 (m), 1215 (s), 1081 (m), 1036 (s).

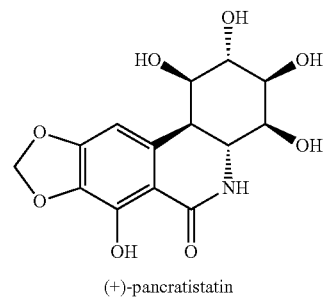

(+)-pancratistatin

Synthesis of (+)-pancratistatin 2 from (+)-pancratistatin tetraacetate S4: To (+)-pancratistatin tetracetate S4 (250 mg, 507 µmol, 1.0 equiv.) in MeOH (5 mL) was added NaOMe (1.0 mL, 25% w/w in MeOH, 3.67 mmol, 7.5 equiv.). The reaction was stirred until completion by TLC before cooling to 0° C. and carefully neutralizing with HCl (313 µL, 12 M). The solution was then concentrated, and the residue was purified by flash chromatography (wet loaded with DMSO and purified using C$_{18}$-functionalized SiO$_2$, H$_2$O:MeCN=1: 0→5:1) to give the desired compound as a colorless solid [152 mg, 461 µmol, 91%].

$R_f$=0.40 (SiO$_2$, CHCl$_3$:MeOH=4:1); $[\alpha]_D^{22}$=+37.0 (c=1.0 in DMSO); Reported values: lit. $[\alpha]_D^{23}$=+38.0 (c=1.08 in DMSO) (J. Am. Chem. Soc. 1998, 120, 5341); lit. $[\alpha]_D^{25}$=+ 44.0 (c=1.0 in DMSO) (J. Am. Chem. Soc. 1995, 117, 10143); lit. $[\alpha]_D^{26}$=+41.0 (c=1.0 in DMSO) (J. Am. Chem. Soc. 1995, 117, 3643); lit. $[\alpha]_D^{25}$=+45.0 (c=0.7 in DMSO) (J. Am. Chem. Soc. 2000, 122, 6624); lit. $[\alpha]_D^{20}$=+46.0 (c=1.0 in DMSO) (J. Org. Chem., 2012, 77, 11377); lit. $[\alpha]_D^{28}$=+36.8 (c=1.0 in DMSO) (Asian J. Org. Chem. 2013, 2, 299); lit. $[\alpha]_D^{34}$=+48.0 (c=1.0 in DMSO) (Eur. J. Org. Chem., 2009, 4666); lit. $[\alpha]_D^{21}$=+37.0 (c=1.0 in DMSO) (J. Chem. Soc., Chem. Commun. 1984, 1693); m.p.=260-264° C. decomposition.

Note: Due to large differences in reported optical rotations, we have prepared peracetylated (+)- and rac-pancratistatin using our synthetic blueprint and subject both to HPLC analysis on a chiral stationary phase. Accordingly, the enantiomeric ratio of our material was determined to be 98:2. See experimental for detailed preparation and characterization of pentaacetate and HPLC trace comparison.

$^1$H NMR (500 MHz, DMSO-d$_6$) δ 13.06 (s, 1H), 7.50 (s, 1H), 6.49 (s, 1H), 6.05 (s, 1H), 6.03 (s, 1H), 5.36 (d, J=4.0 Hz, 1H), 5.08 (d, J=5.7 Hz, 1H), 5.05 (d, J=6.1 Hz, 1H), 4.83 (d, J=7.5 Hz, 1H), 4.42-4.20 (m, 1H), 4.07-3.92 (m, 1H), 3.93-3.80 (m, 1H), 3.81-3.67 (m, 2H), 2.97 (d, J=12.2 Hz, 1H).

$^{13}$C NMR (126 MHz, DMSO-d$_6$) δ 169.5, 152.1, 145.4, 135.7, 131.7, 107.5, 101.8, 97.7, 73.3, 70.2, 70.0, 68.5, 50.5, (39.5 observed by HSQC).

HRMS (ESI-TOF, m/z) calcd. For C$_{14}$H$_{16}$NO$_8$ [M+H]$^+$ calc.: 326.0876; found: 326.0872.

IR (ATR, neat, cm$^{-1}$): 3348 (m), 2926 (w), 1673 (m), 1615 (w), 1597 (m), 1462 (m), 1416 (m), 1347 (s), 1297 (m), 1228 (m), 1082 (s), 1065 (s), 1036 (s), 877 (m).

Example 5. Streamlined Synthesis of Pancratistatins 1 and 2

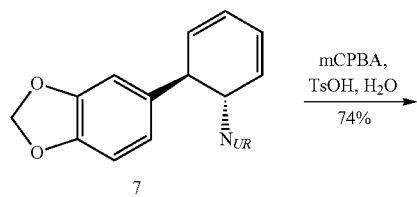

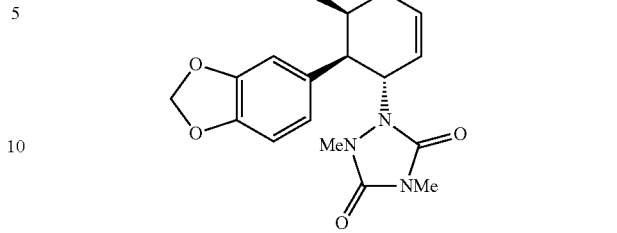

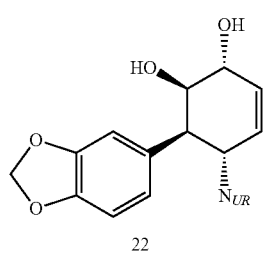

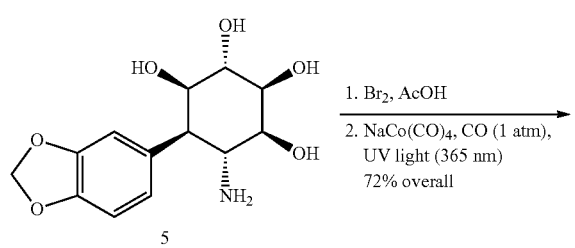

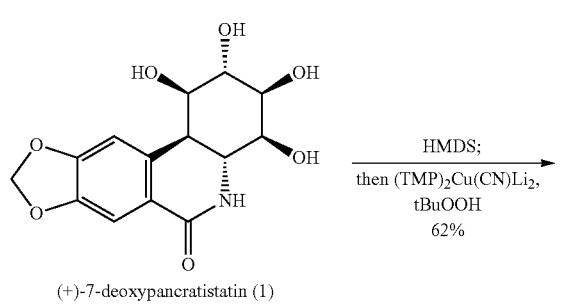

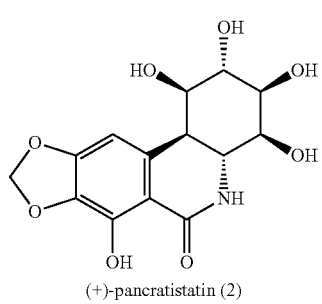
(+)-pancratistatin (2)

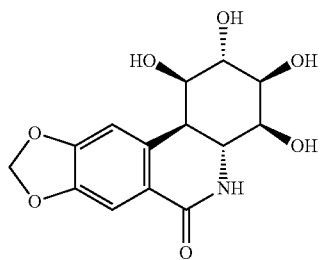
7-deoxypancratistatin

Synthesis of diol 22 from diene 7: To a stirred solution of diene 7 (9.16 g, 28.0 mmol, 1.0 equiv.) in CH$_2$Cl$_2$:HFIP:H$_2$O (110 mL, 8:3:1) at 0° C. was added pTsOH H$_2$O (532 mg, 2.80 mmol, 10 mol %) and mCPBA (7.84 g, 77% w/w, 35.0 mmol, 1.25 equiv.) and the resulting mixture was stirred for 10 min. The solution was then heated to 50° C. for 8 h. Upon completion (TLC monitoring), the reagents were quenched with Na$_2$S2O3 (10% aq. 100 mL) and NaHCO$_3$ (sat. aq. 200 mL). The organic phase was separated and the aqueous phase was extracted with EtOAc (5×250 mL). The combined organic extracts were dried over MgSO$_4$, filtered and concentrated under reduced pressure. The residue was purified by flash chromatography (SiO$_2$, CH$_2$Cl$_2$:MeOH=50:1-10:1) to give the desired compound as a colorless solid [7.44 g, 20.6 mmol, 74%]. Characterization data of this compound were in accordance with the values reported above.

Synthesis of (+)-7-deoxypancratistatin (1) from amine 5: To a stirred solution of amine 5 (2.1 g, 7.4 mmol, 1.0 equiv.) in AcOH (25 mL) was added Br$_2$ (9.63 mL, 1.0 M in AcOH, 9.63 mmol, 1.3 equiv.) dropwise. The resulting mixture was stirred in the dark at room temperature for 3 h. The solvent was removed under reduced pressure and the residual bromine was removed by co-evaporation with PhMe (3×5 mL) under reduced pressure. Then, nBu$_4$NBr (1.43 g, 4.45 mmol, 0.6 equiv.) and NaCo(CO)$_4$ (431 mg, 2.22 mmol, 30 mol %) were added followed by NaHCO$_3$ (sat. aq. 37 mL) and 1,4-dioxane (37 mL) and the flask was sealed with a septum. The suspension and reaction vessel were purged with CO and the reaction was stirred under a CO atmosphere (1 atm) at 60° C. under 365 nm irradiation for 8 h. Upon completion, the reaction was purged with N$_2$ and the solvent was removed under reduced pressure. The resulting residue was purified by flash chromatography (Cis functionalized SiO$_2$, H$_2$O:MeOH=5:1→3:1, and then SiO$_2$, CH$_2$Cl$_2$:MeOH=9:1→6:1) to give (+)-7-deoxypancratistatin (1) as a colorless solid [1.64 g, 5.3 mmol, 72% overall]. Characterization data of this compound were in accordance with the values reported above.

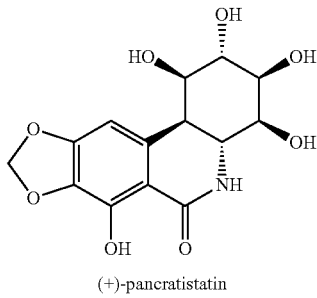

(+)-pancratistatin

Synthesis of (+)-pancratistatin (2): To (+)-7-deoxypancratistatin (1, 100 mg, 0.32 mmol) was added MeCN (2.0 mL), HMDS (2.03 mL, 9.70 mmol, 30 equiv.), and iodine (0.8 mg, 0.003 mmol, 1 mol %), and (+)-pancrattatin (2) the resulting mixture was stirred at 80° C. for 12 h under an inert atmosphere. The resulting clear solution was cooled to room temperature and the volatiles were removed under reduced pressure. Trace amounts of HMDS were completely removed by azeotropic co-evaporation using toluene (3×2 mL). The flask containing leftover residue was flushed with nitrogen and sealed with rubber septa. THF (1.00 mL) was introduced and the resulting solution was cooled to −78° C. Then freshly prepared $(TMP)_2Cu(CN)Li_2$ (3.73 mL, 0.195 M in THF, 0.73 mmol, 2.0 equiv.) was added and the mixture was warmed to 0° C. and stirred for 2 h at this temperature. The reaction was cooled again to −78° C. and tBuOOH (0.15 mL, 5.5 M in decane, 1.62 mmol, 2.5 equiv.) was added dropwise and solution was further stirred for 30 min before a mixture of sat. aq. $NH_4Cl$ and 10% aq. $Na_2S_2O_3$ (10 mL, 1:1) were added. After warming to room temperature, phases were separated and the aqueous phase was extracted with EtOAc (4×5 mL). A mixture of $CF_3COOH$:MeOH (20 mL, 1:1) was added to the combined organic extracts and volatiles were removed under reduced pressure. The residue was purified by flash chromatography (wet loaded with DMSO and purified using $C_{18}$-functionalized $SiO_2$, $H_2O$:MeCN=1: 0→5:1; and then dry loaded using MeOH, $SiO_2$, $CHCl_3$: MeOH=10:1→4:1) to give pancratistatin (2) as a colorless solid [65.0 mg, 0.20 mmol, 62%]. Characterization data of this compound were in accordance with the values reported above.

Control Experiments Showcasing that Tetra-O-TMS Protected 7-Deoxypancratistatin (33) is an Intermediate En-Route to Pancratistatin (2)

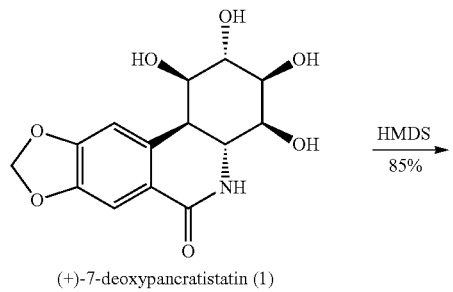

(+)-7-deoxypancratistatin (1)

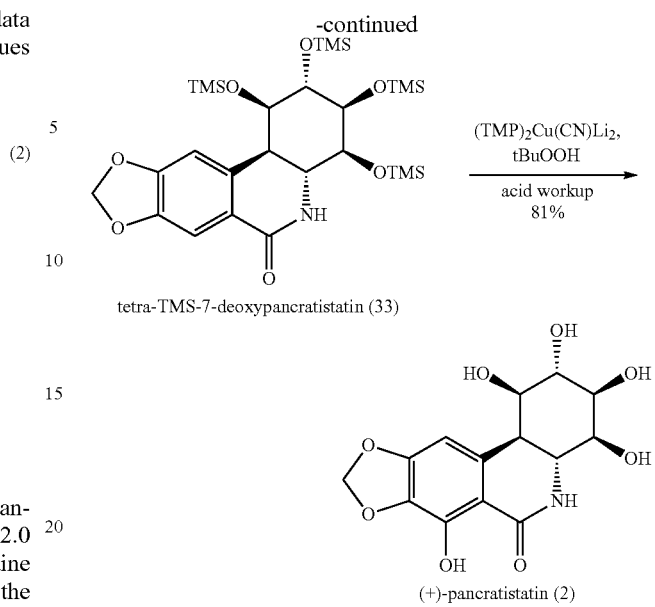

tetra-TMS-7-deoxypancratistatin (33)

Conversion of 1→33: To (+)-7-deoxypancratistatin (1, 100 mg, 0.32 mmol, 1 equiv.) was added MeCN (2.0 mL), HMDS (2.03 mL, 9.70 mmol, 30 equiv.), and iodine (0.8 mg, 0.003 mmol, 1.0 mol %), and the resulting mixture was stirred at 80° C. for 12 h under an inert atmosphere. The resulting clear solution was cooled to room temperature and the volatiles were removed under reduced pressure. The residue was purified by flash chromatography ($SiO_2$, hexanes:EtOAc, containing 1% $Et_3N$=8:1→4:1) to give the desired compound as a colorless solid [165 mg, 0.28 mmol, 85%].

$R_f$=0.40 ($SiO_2$, hexanes:EtOAc 1% TEA=4:1); $[\alpha]_D^{22}$=+104.7 (c=1.0 in benzene); m.p.=56-57° C.

$^1$H NMR (500 MHz, $C_6D_6$) δ 8.16-8.11 (m, 1H), 6.71 (s, 1H), 6.10-5.93 (m, 1H), 5.31-5.19 (m, 2H), 4.56-4.43 (m, 1H), 4.38 (t, J=2.9 Hz, 1H), 4.08-4.00 (m, 2H), 3.94 (td, J=2.9, 1.0 Hz, 1H), 3.28 (dd, J=12.7, 1.7 Hz, 1H), 0.21 (s, 9H), 0.17-0.14 (m, 18H), 0.11 (s, 9H).

$^{13}$C NMR (126 MHz, $C_6D_6$) δ 164.8, 151.1, 146.9, 134.5, 125.3, 108.9, 105.2, 101.4, 76.0, 74.8, 74.1, 71.9, 49.0, 42.1, 1.02, 1.01, 0.2, 0.0.

HRMS (ESI-TOF, m/z) calcd. For $C_{26}H_{48}NO_7Si_4$ [M+H]$^+$ calc.: 598.2502; found: 598.2508.

IR (ATR, neat, cm$^{-1}$): 3418 (w), 2955 (w), 2899 (w), 1669 (m), 1619 (w), 1483 (w), 1250 (m), 1133 (m), 1082 (m), 886 (m), 837 (s).

Conversion of 33→2: In an oven-dried vial, tetra-TMS-7-deoxypancratistatin (33, 39.0 mg, 0.065 mmol, 1 equiv.) was dissolved in THF (0.20 mL) and cooled to −78° C. Then freshly prepared $(TMP)_2Cu(CN)Li_2$ (0.67 mL, 0.195 M in THF, 0.13 mmol, 2.0 equiv.) was added and the mixture was warmed to 0° C. and stirred for 2 h at this temperature. The reaction was cooled again to −78° C. and tBuOOH (0.03 mL, 5.5 M in decane, 0.16 mmol, 2.5 equiv.) was added dropwise and solution was further stirred for 30 min before a mixture of sat. aq. $NH_4Cl$ and 10% aq. $Na_2S_2O_3$ (2 mL, 1:1) were added. After warming to room temperature, phases were separated and the aqueous phase was extracted with EtOAc (4×2 mL). A mixture of $CF_3COOH$:MeOH (5 mL, 1:1) was added to the combined organic extracts and volatiles were removed under reduced pressure. The remaining residue was purified with two chromatographic separations (wet loaded with DMSO and purified using Cis functionalized SiO$_2$, H$_2$O:MeCN=1:0-5:1; and then dry loaded with MeOH, SiO$_2$, CHCl$_3$:MeOH=10:1→4:1) to give pancratistatin (2) as a colorless solid [17.0 mg, 0.05 mmol, 81%]. Characterization data of this compound were in accordance with the values reported above.

Determination of Optical Purity of (+)-Pancratistatin (2) by HPLC Analysis of Pancratistatin Pentaacetate (S5)

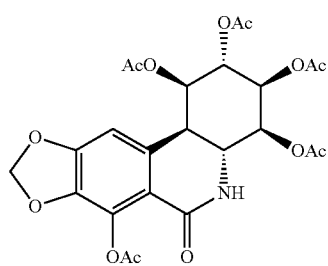

S5

Pancratistatin pentaacetate (S5): To a stirred suspension of pancratistatin 2 (97.0 mg, 0.30 mmol, 1 equiv.) in THF (3.0 mL) was added DMAP (3.7 mg, 0.03 mmol, 10 mol %), triethylamine (0.25 mL, 1.79 mmol, 6.0 equiv.), and acetic anhydride (0.17 mL, 1.79 mmol, 6.0 equiv.) and reaction was stirred at room temperature under inert atmosphere overnight. Upon completion, the reaction was partitioned between 1N HCl (5 mL) and EtOAc (5 mL). The organic phase was separated and the aqueous phase was extracted with EtOAc (3×5 mL). The combined organic extracts were washed vigorously with NaHCO$_3$ (sat. aq. 10 mL), dried over MgSO$_4$, filtered and concentrated under reduced pressure. The resulting residue was purified by flash chromatography (SiO$_2$, hexanes:EtOAc=2:1→1:2) to give pancratistatin pentaacetate as a colorless solid [145 mg, 0.27 mmol, 91%]. Characterization data for this compound were in accordance with the literature values (Asian J. Org. Chem. 2013, 2, 299).

Enantioselectivity of 98:2 was determined with HPLC using Daicel Chiralpak® IA-3 column 50% iPrOH in hexanes, 0.8 mL/min, t$_R$(minor)=7.7 min, t$_R$(major)=16.8 min.

R$_f$=0.37 (SiO$_2$, hexanes:EtOAc=1:2); [α]$_D^{22}$=+64.6 (c=1.0 in CHCl$_3$); m.p.=162-166° C.

$^1$H NMR (500 MHz, CDCl$_3$) δ 6.46 (s, 1H), 6.10-6.02 (m, 2H), 5.83 (s, 1H), 5.60-5.51 (m, 1H), 5.50-5.40 (m, 1H), 5.23-5.17 (m, 1H), 5.12 (dd, J=10.8, 3.5 Hz, 1H), 4.24 (dd, J=12.9, 10.8 Hz, 1H), 3.43 (dd, J=12.9, 2.9 Hz, 1H), 2.35 (s, 3H), 2.15 (s, 3H), 2.07 (s, 3H), 2.05-2.03 (m, 6H)

$^{13}$C NMR (126 MHz, CDCl$_3$) δ 170.1, 169.8, 169.17, 169.16, 168.4, 163.0, 152.7, 139.9, 134.5, 132.9, 116.2, 103.1, 101.9, 71.7, 67.7, 66.9, 66.5, 47.9, 40.0, 21.0, 20.9, 20.85, 20.81, 20.7.

HRMS (ESI-TOF, m/z) calcd. For C$_{24}$H$_{26}$NO$_{13}$ [M+H]$^+$ calc.: 536.1404; found: 536.1411.

IR (ATR, neat, cm$^{-1}$): 3355 (w), 1745 (s), 1669 (s) 1634 (w), 1505 (w), 1484 (m), 1369 (m), 1340 (w), 1289 (w), 1247 (m), 1211 (s), 1176 (m), 1080 (m), 1042 (s), 949 (w), 925 (m), 861 (w), 815 (w), 754 (m), 639 (w).

Example 6. Total Synthesis of (+)-Narciclasine (4)

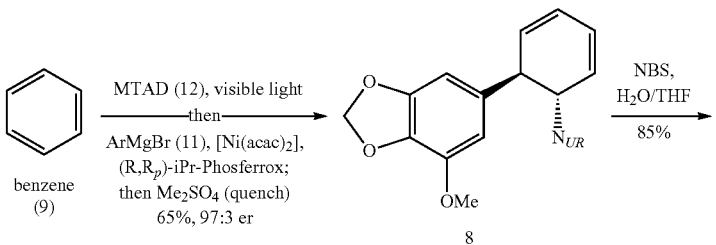

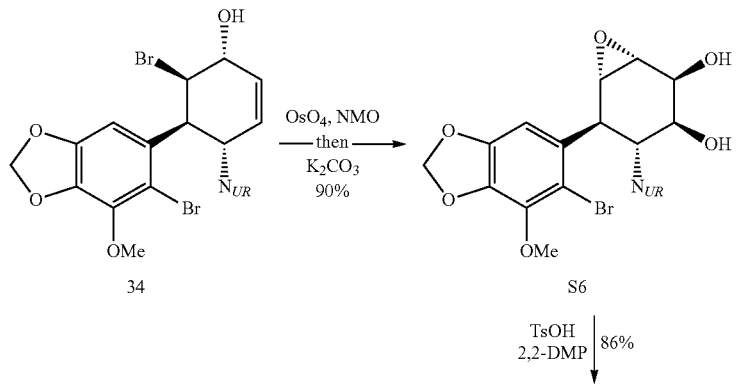

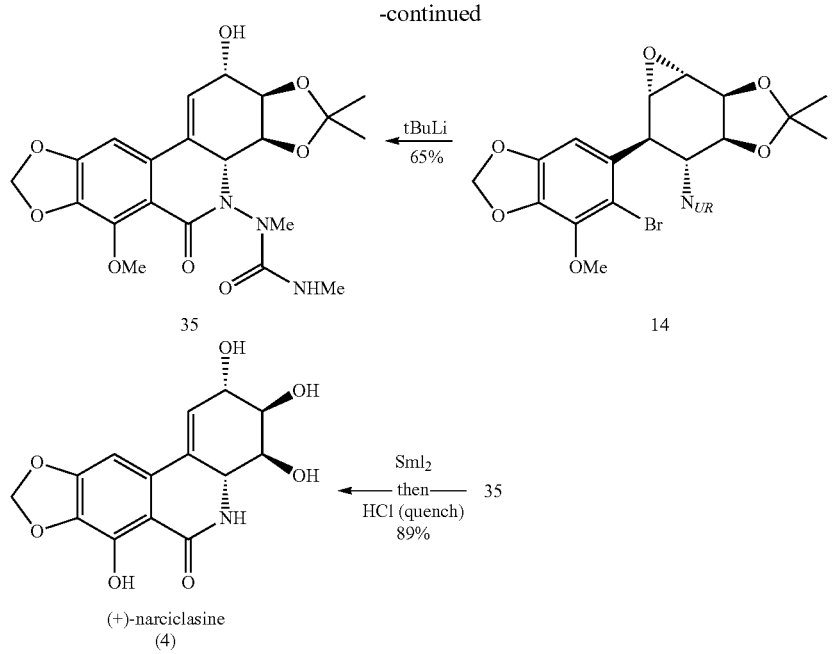

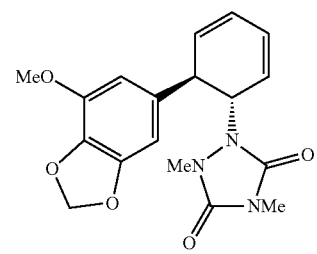

Synthesis of diene 8: In an oven-dried 1 L media bottle, MTAD (12, 6.00 g, 53 mmol, 1.0 equiv.) was dissolved in anhydrous $CH_2Cl_2$ (265 mL) under nitrogen atmosphere and cooled to −78° C. Benzene (9) (47.3 mL, 0.53 mol, 10 equiv.) was slowly added and the solution was stirred for five minutes. The pink solution was irradiated with LED lights at −78° C. until complete loss of color. Upon decolorization, the LED lights were turned off and a solution of [Ni(acac)$_2$] (204.5 mg, 0.79 mmol, 1.5 mol %) and (R,R$_p$)-iPr-Phosferrox (501 mg, 1.06 mmol, 2.0 mol %) in $CH_2Cl_2$ (32 mL) (pre-stirred at 20° C. for 45 minutes then cooled to −78° C.) was added, followed by dropwise addition of 3,4-methylenedioxy-5-methoxy-phenyl bromide (11, 44.2 mL, 3.0 M in THF, 133 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath and after stirring at room temperature for 15 min, $Me_2SO_4$ (25.2 mL, 265 mmol, 5.0 equiv.) and $K_2CO_3$ (18.0 g, 133 mmol, 2.5 equiv.) were added sequentially and the mixture was stirred at 35° C. for 8 h. The mixture was cooled to 0° C. and 5% aq. $NH_4OH$ (300 mL) was added, the phases were separated, and the aqueous phase was extracted with $CH_2Cl_2$ (2×200 mL). The combined organic extracts were washed with water (2×200 mL) and brine (200 mL), dried over $MgSO_4$, filtered and concentrated under reduced pressure. The residue was purified by flash chromatography ($SiO_2$, hexanes:EtOAc=5:1→3:1) to give the desired compound as a colorless solid [22.5 g, 68.7 mmol, 66% 97:3 er]. Characterization data of this compound were in accordance with the values reported above.

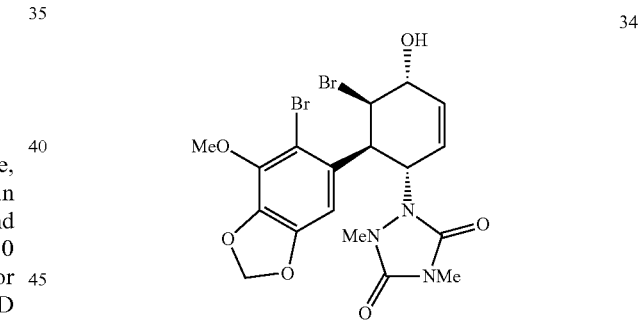

Synthesis of bromohydrin 34: Bromohydrin 34 was prepared using the procedure to synthesize bromohydrin 25. Diene 8 (6.00 g, 16.8 mmol) was subjected to the reaction conditions. The residue was purified by flash chromatography ($SiO_2$, hexanes:EtOAc=4:1→1:1) to give the desired compound as a colorless solid [7.61 g, 14.3 mmol, 85%].

$R_f$=0.56 ($SiO_2$, hexanes:EtOAc=1:3); $[\alpha]^{22}$=+134.2 (c=1.0 in $CHCl_3$); m.p.=248-250° C. decomposition.

NMR analysis of bromohydrin 34 revealed several conformational structures at 20° C., which increased spectrum complexity. Unfortunately, when variable-temperature NMR spectroscopy was employed, no coalescence of the peaks was observed.

$^1$H NMR (500 MHz, $CDCl_3$) δ 6.90 (s, 1H), 6.82 (s, 0.1H), 6.12-6.06 (m, 1H), 6.05 (s, 0.1H), 5.99-5.97 (m, 2.3H), 5.89 (d, J=10.3, 1H), 5.35 (bs, 0.1H), 5.17 (bs, 1H), 4.68-4.51 (m, 2.2H), 4.34 (s, 1H), 4.30 (s, 0.1H), 4.03 (s, 3H), 3.94 (s, 0.3H), 3.17 (s, 0.3H), 3.15 (s, 3H), 2.97 (s, 3H), 2.92 (s, 0.3H), 2.76-2.55 (m, 1.1H).

$^{13}$C NMR (126 MHz, CDCl$_3$) δ 155.4, 155.3, 148.5, 140.6, 137.1, 130.1, 128.3, 110.4, 109.7, 104.5, 102.0, 69.5, 60.3, 57.3, 55.8, 41.9, 34.7, 25.7.

HRMS (ESI-TOF, m/z) calcd. For C$_{18}$H$_{20}$Br$_2$N$_3$O$_6$ [M+H]$^+$ calc.: 531.9719; Found: 531.9736.

IR (ATR, neat, cm$^{-1}$): 3404 (br), 2888 (w), 1763 (m), 1687 (s), 1482 (s), 1234 (m), 1054 (m), 935 (w), 774 (w).

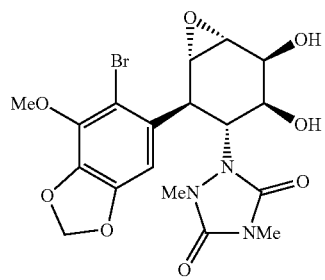

S6

Synthesis of epoxydiol S6: To a stirred solution of (+)-bromohydrin 34 (7.00 g, 13.1 mmol, 1.0 equiv.), N-methylmorpholine-N-oxide (2.33 g, 19.7 mmol, 1.5 equiv.), and citric acid (5.52 g, 26.3 mmol, 2.0 equiv.) in acetone:H$_2$O:tBuOH (105 mL, 1:1:2) at 25° C. was added OsO$_4$ (3.3 mL, 0.2 M in MeCN, 0.66 mmol, 5.0 mol %) and the resulting mixture was stirred overnight or until complete conversion as judged by TLC. The reagents were quenched with 10% aq. Na$_2$S$_2$O$_3$ (50 ml) and the resulting solution was stirred for 30 min, before diluting with H$_2$O (100 mL), then K$_2$CO$_3$ (18.1 g, 131 mmol, 10 equiv.) was added and the reaction was stirred until complete conversion as judged by TLC. The organic phase was separated, and the aqueous phase was extracted with EtOAc (2×100 mL). The combined organic extracts were dried over MgSO$_4$, filtered and concentrated under reduced pressure. The residue was purified by flash chromatography (SiO$_2$, CH$_2$Cl$_2$:MeOH=30:1→15:1) to give the desired compound as a colorless solid [5.72 g, 11.8 mmol, 90%].

R$_f$=0.37 (SiO$_2$, CH$_2$Cl$_2$:MeOH=8:1); [α]$_D^{22}$=+62.9 (c=1.0 in CHCl$_3$); m.p.=163-165° C.

NMR analysis of epoxydiol S6 revealed several conformational structures at 20° C., which increased spectrum complexity. Therefore, a variable-temperature NMR spectroscopy was employed, and a full coalescence of the peaks was observed at 100° C. For clarity only the two major conformers at 20° C. are described.

$^1$H NMR (500 MHz, DMSO-d$_6$, 20° C.) δ 6.94 (s, 1H), 6.79 (s, 0.8H), 6.11 (s, 1.8H), 6.08-6.04 (m, 1.8H), 5.71 (d, J=4.5 Hz, 1H), 5.63 (d, J=4.4 Hz, 0.8H), 4.93-4.88 (m, 1.8H), 4.49 (t, J=10.3 Hz, 1H), 4.37-4.30 (m, 1.8H), 4.26 (d, J=9.8 Hz, 0.8H), 4.08 (d, J=9.9 Hz, 1H), 3.96-3.90 (m, 5.4H), 3.88-3.82 (m, 1.8H), 3.63 (t, J=10.3 Hz, 0.8H), 3.36 (t, J=3.3 Hz, 1.8H), 3.22 (s, 3H), 2.96 (s, 0.8H), 2.91 (s, 1H), 2.88 (s, 2.4H), 2.79 (s, 3H), 2.46 (s, 2.4H).

$^1$H NMR (500 MHz, DMSO-d$_6$, 100° C.) δ 6.89 (s, 1H), 6.08 (s, 1H), 6.05 (s, 1H), 5.29 (s, 1H), 4.42 (d, J=6.6 Hz, 1H), 4.39-4.37 (m, 1H), 4.29-4.05 (m, 2H), 3.94 (s, 3H), 3.01-2.93 (m, 3H), 3.01-2.81 (m, 1H) 2.84 (s, 3H).

$^{13}$C NMR (126 MHz, DMSO-d$_6$, 20° C.) δ 155.6, 155.1, 153.9, 152.8, 149.1, 148.8, 140.2, 139.5, 137.0, 136.6, 134.6, 133.6, 109.2, 108.9, 103.3, 102.6, 102.2*, 67.7, 67.4, 65.9, 64.7, 60.3, 60.1, 60.0, 59.9, 55.5, 55.2**, 47.1, 43.0, 34.9, 31.2, 25.2, 24.8. (* Overlap of 2 peaks, ** Overlap of 3 peaks)

$^{13}$C NMR (126 MHz, DMSO-d$_6$, 100° C.) δ 148.5, 139.4, 136.4, 133.4, 108.8, 102.8, 101.6, 67.3, 65.2, 59.5, 59.3, 55.0*, 42.9, 24.3. (* Overlap of 2 peaks) HRMS (ESI-TOF, m/z) calcd. For C$_{18}$H$_{21}$BrN$_3$O$_8$ [M+H]$^+$ calc.: 486.0512; Found: 486.0526.

IR (ATR, neat, cm$^{-1}$): 3414 (m), 2945 (w), 1747 (w), 1695 (s), 1477 (s), 1217 (m), 1085 (m), 922 (m), 728 (m).

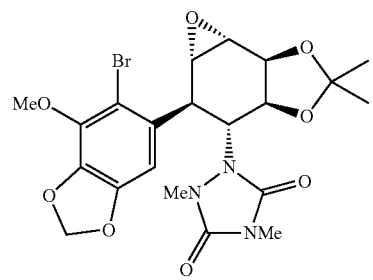

14

Synthesis of epoxyacetonide 14: To a stirred solution of (+)-epoxydiol S6 (5.00 g, 10.3 mmol, 1.0 equiv.) and 2,2-dimethoxypropane (2.5 mL, 20.6 mmol, 2.0 equiv.) in CH$_2$Cl$_2$ (59 mL) at 0° C. was added pTsOH H$_2$O (0.20 g, 1.0 mmol, 10 mol %) and the resulting mixture was stirred for 5 min before it was warmed to 25° C. and stirred for an additional 1 h or until complete conversion as judged by TLC. The reagents were quenched with aq. NaOH (20 ml, 2.0 M) and the resulting solution was stirred for 5 min, then diluted with H$_2$O (100 mL). The phases were separated, and the aqueous phase was extracted with CH$_2$Cl$_2$ (3×100 mL). The combined organic layers were dried over MgSO$_4$, filtered and concentrated under reduced pressure. The residue was purified by flash chromatography (SiO$_2$, hexanes:EtOAc=2:1→1:3) to give the desired compound as a colorless solid [4.65 g, 8.84 mmol, 86%].

R$_f$=0.36 (SiO$_2$, hexanes:EtOAc=1:1); [α]$_D^{23}$=+190.7 (c=1.0 in CHCl$_3$); m.p.=209-213° C.

NMR analysis of epoxyacetonide 14 revealed several conformational and rotameric structures at 20° C., which increased spectrum complexity. Therefore, variable-temperature NMR spectroscopy was employed, and a full coalescence of the peaks was observed at 100° C. For clarity only the two major conformers at 20° C. are described.

$^1$H NMR (500 MHz, DMSO-d$_6$, 20° C.) δ 6.82 (s, 1H), 6.79 (s, 0.2H), 6.11-6.06 (m, 2H), 6.05-6.04 (m, 0.4H), 5.01 (dd, J=12.6, 10.4 Hz, 0.2H), 4.83 (dd, J=11.8, 5.5 Hz, 1H), 4.44 (s, 1H), 4.25 (dd, J=10.4, 5.2 Hz, 0.2H), 4.17 (dd, J=12.1, 9.8 Hz, 0.2H), 3.93 (s, 3H), 3.91 (s, 0.6H), 3.83-3.72 (m, 1H), 3.66-3.61 (m, 0.2H), 3.51-3.46 (m, 1H), 3.16 (s, 0.2H), 3.13 (s, 1H), 2.94 (s, 3.6H), 2.84 (s, 0.6H), 2.82 (s, 3H), 2.71 (s, 0.2H), 2.68 (s, 1H), 1.47 (s, 0.6H), 1.44 (s, 3H), 1.35 (s, 0.6H), 1.32 (s, 3H).

$^1$H NMR (500 MHz, DMSO-d$_6$, 100° C.) δ 6.79 (s, 1H), 6.06 (s, 1H), 6.05 (s, 1H), 4.83 (d, J=5.5 Hz, 1H), 4.50 (s, 1H), 4.18 (s, 1H), 3.94 (s, 3H), 3.89-3.78 (m, 1H), 3.50 (s, 1H), 3.16 (s, 1H), 2.95 (s, 3H), 2.83 (s, 3H), 1.49 (s, 3H), 1.37 (s, 3H).

$^{13}$C NMR (126 MHz, DMSO-d$_6$, 20° C.) δ 155.7, 155.5, 153.9, 153.2, 148.8, 147.8, 140.2, 139.8, 137.1, 136.7, 131.7, 130.8, 110.2, 110.0, 109.7, 109.5, 108.2, 103.1, 102.2*, 73.0, 72.9, 72.8, 72.6, 60.0, 59.9, 59.5, 58.5, 57.8, 57.5, 53.0, 51.6, 45.7, 43.4, 36.0, 32.1, 27.4, 27.2, 26.1, 25.7, 25.2, 24.7. (* Overlap of 2 peaks)

¹³C NMR (126 MHz, DMSO-d₆, 100° C.) δ 154.8, 154.5, 148.4, 139.7, 136.5, 131.4, 109.5, 109.3, 102.7, 101.7, 72.8, 72.4, 59.5, 59.3, 57.9, 51.3, 43.1, 34.2, 26.9, 25.2, 24.4.

HRMS (ESI-TOF, m/z) calcd. For C$_{21}$H$_{25}$BrN$_3$O$_8$ [M+H]$^+$ calc.: 526.0825; Found: 526.0820.

IR (ATR, neat, cm$^{-1}$): 2986 (w), 1767 (w), 1704 (s), 1477 (s), 1249 (m), 1216 (s), 1077 (s), 921 (m), 774 (m).

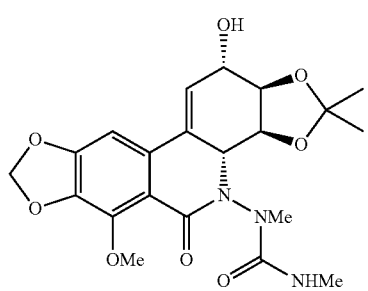

Synthesis of lactam 35: To a stirred solution of (+)-epoxyacetonide 14 (4.00 g, 7.60 mmol, 1.0 equiv.), in THF (304 mL) at −78° C. was added a solution of tBuLi (25.5 mL, 0.7 M in hexanes, 17.9 mmol, 2.35 equiv.) over 3 h. The reagents were then quenched with sat. aq. NH$_4$Cl (40 mL) at −78° C. then the reaction was warmed to 25° C. The resulting mixture was diluted with H$_2$O (100 mL) and the phases were separated. The aqueous phase was extracted with EtOAc (5×300 mL) and the combined organic layers were dried over MgSO$_4$, filtered and concentrated under reduced pressure. The residue was purified by flash chromatography (SiO$_2$, CH$_2$Cl$_2$:MeOH=50:1→30:1) to give the desired compound as a colorless solid [2.21 g, 4.94 mmol, 65%].

R$_f$=0.31 (SiO$_2$, CH$_2$Cl$_2$:MeOH=8:1); [α]$_D^{22}$=−5.9 (c=0.5 in CHCl$_3$); m.p.=161-163° C. decomposition.

NMR analysis of lactam 35 revealed several conformational structures at 20° C., which increased spectrum complexity. Unfortunately, when variable-temperature NMR spectroscopy was employed no coalescence of the peaks was observed.

¹H NMR (500 MHz, CDCl$_3$) δ 6.84 (s, 1H), 6.81 (s, 0.4H), 6.40 (t, J=3.1 Hz, 1H), 6.35 (t, J=3.1 Hz, 0.4H), 6.04 (s, 2H), 6.02-6.00 (m, 1H), 5.05 (q, J=4.8 Hz, 1H), 4.57 (bs, 0.4H), 4.55-4.49 (m, 1.4H), 4.45-4.40 (m, 1H), 4.35-4.26 (m, 2H), 4.06-4.01 (m, 1.4H), 4.04 (s, 3H), 4.02 (s, 1.2H), 3.28 (s, 1.2H), 3.13 (s, 3H), 3.06 (s, 0.4 H), 2.95 (s, 1H), 2.81 (d, J=4.6 Hz, 1.2H), 2.76 (d, J=4.8 Hz, 3H), 1.54-1.45 (m, 4.2H), 1.36 (s, 1.2H), 1.34 (s, 3H).

¹³C NMR (126 MHz, CDCl$_3$) δ 161.9*, 159.1, 157.7, 153.2, 152.8, 145.2, 145.2, 139.4, 139.2, 131.4, 130.4, 128.4, 128.4, 126.9*, 113.1*, 111.4, 110.3, 102.3, 102.2, 97.8, 97.2, 79.6, 78.8, 78.4, 76.1, 72.5, 71.0, 63.0, 61.1, 61.0, 60.5, 38.8, 31.9, 27.7, 27.6, 27.5, 27.2, 25.2, 24.9. (* Overlap of 2 peaks) HRMS (ESI-TOF, m/z) calcd. For C$_{21}$H$_{26}$N$_3$O$_8$ [M+H]$^+$ calc.: 448.1720; Found: 448.1716.

IR (ATR, neat, cm$^{-1}$): 3397 (m), 2924 (w), 1661 (s), 1526 (m), 1480 (s), 1213 (s), 1049 (m), 932 (m), 771 (s).

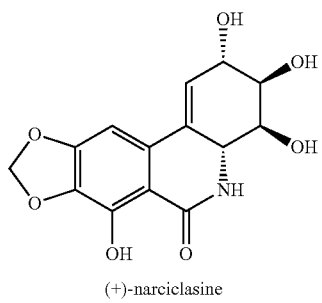

(+)-narciclasine

Synthesis of (+)-narciclasine 4: To a stirred solution of (−)-lactam 35 (1.00 g, 2.23 mmol, 1.0 equiv.), in degassed MeOH (30 mL) at 0° C. was added dropwise a solution of SmI$_2$ (44.7 mL, 0.1 M in THF, 4.47 mmol, 2.0 equiv.) over 30 min. The solution was then heated to (+)-narciclasine (4) 40° C. and was allowed to stir until complete conversion as judged by TLC. Then aq. HCl (40 mL, 6.0 M) was added and the resulting solution was stirred until complete conversion as judged by TLC. The solution was then carefully neutralized with solid NaHCO$_3$ (20 g). The resulting suspension was filtered and concentrated under reduced pressure. The residue was purified by flash chromatography (wet loaded with DMSO and purified using C$_{18}$-functionalized SiO$_2$, H$_2$O:MeOH=1:0→5:1) to give (+)-narciclasine as a colorless solid [610 mg, 1.99 mmol, 89%]. Characterization data of (+)-narciclasine (4) were in accordance with the literature values.

R$_f$=0.33 (SiO$_2$, CHCl$_3$:MeOH=4:1); [α]$_D^{23}$=+144.0 (c=0.7 in MeOH); [α]$_D^{23}$=+165.2 (c=1.0 in DMSO); Reported Values: Lit [α]$_D^{25}$=+141.8 (c=0.7 in MeOH) (J. Am. Chem. Soc., 1997, 119, 12655); Lit [α]$_D^{25}$=+142.8 (c=0.7 in MeOH) (Phytochem. 1985, 24, 1825); m.p.=200-216° C. decomposition.

¹H NMR (500 MHz, DMSO-d$_6$) δ 13.26 (s, 1H), 7.89 (s, 1H), 6.86 (s, 1H), 6.16-6.14 (m, 1H), 6.11-6.07 (m, 2H), 5.20-5.18 (m, 2H), 5.02 (d, J=3.7 Hz, 1H), 4.19 (ddd, J=8.6, 2.6, 1.4 Hz, 1H), 4.03-3.99 (m, 1H), 3.80 (ddd, J=8.6, 5.5, 2.2 Hz, 1H), 3.71-3.68 (m, 1H).

¹³C NMR (126 MHz, DMSO-d$_6$) δ 168.9, 152.3, 144.8, 133.4, 132.1, 129.2, 124.8, 105.6, 102.1, 95.8, 72.4, 69.1, 68.8, 52.9.

HRMS (ESI-TOF, m/z) calcd. For C$_{14}$H$_{17}$N$_2$O$_7$ [M+NH$_4$]$^+$ calc.: 325.1030; Found: 325.1039.

IR (ATR, neat, cm$^{-1}$): 3441 (br), 3205 (m), 2908 (m), 1666 (s), 1468 (s), 1355 (s), 1281 (m), 1079 (s), 1033 (s).

Example 7. Scalable Synthesis of (+)-Lycoricidine (3) and (+)-Narciclasine (4)

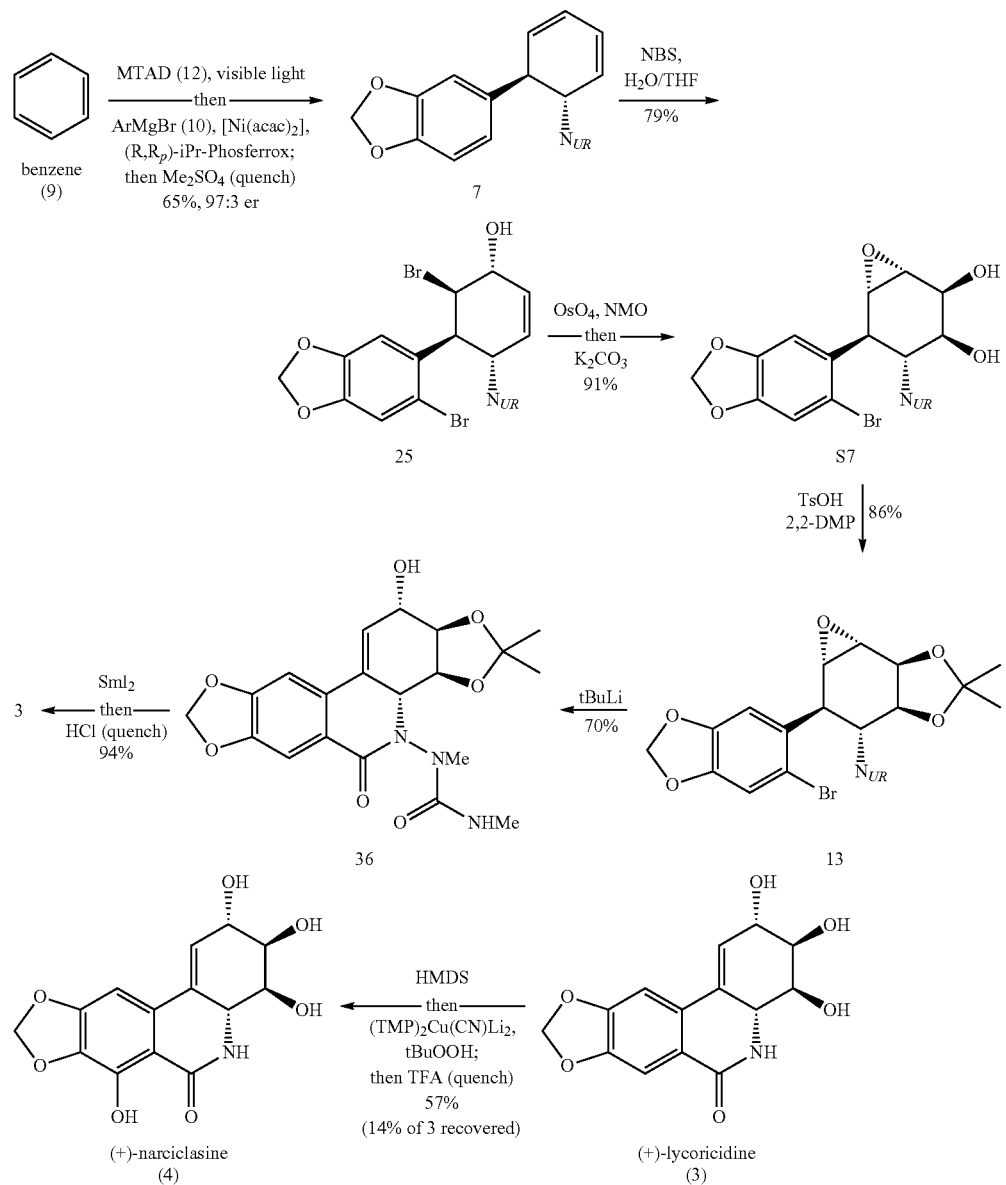

Synthesis of (+)diene 7: In an oven-dried 1 L media bottle, MTAD (12, 12.00 g, 106 mmol, 1.0 equiv.) was dissolved in anhydrous $CH_2Cl_2$ (531 mL) under nitrogen atmosphere and cooled to −78° C. Benzene (9) (94.6 mL, 1.06 mol, 10 equiv.) was slowly added and the solution was stirred for five minutes. The pink solution was irradiated with LED lights at −78° C. until complete loss of color. Upon decolorization, the LED lights were turned off and a solution of [Ni(acac)$_2$] (408.9 mg, 1.59 mmol, 1.5 mol %) and (R,R$_p$)-iPr-Phosferrox (1.02 g, 2.12 mmol, 2.0 mol %) in $CH_2Cl_2$ (64 mL) (pre-stirred at 20° C. for 45 minutes then cooled to −78° C.) was added, followed by dropwise addition of 3,4-methylenedioxyphenylmagnesium bromide (10, 88.4 mL, 3.0 M in THF, 265 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath and after stirring at room

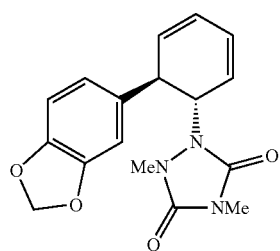

temperature for 15 min, Me$_2$SO$_4$ (50.3 mL, 530 mmol, 5.0 equiv.) and K$_2$CO$_3$ (36.0 g, 265 mmol, 2.5 equiv.) were added sequentially and the mixture was stirred at 35° C. for 8 h. The mixture was cooled to 0° C. and 5% aq. NH$_4$OH (600 mL) was added, the phases were separated, and the aqueous phase was extracted with CH$_2$Cl$_2$ (2×400 mL). The combined organic extracts were washed with water (2×400 mL) and brine (400 mL), dried over MgSO$_4$, filtered and concentrated under reduced pressure. The residue was purified by flash chromatography (SiO$_2$, hexanes:EtOAc=5: 1→3:1) to give the desired compound as a colorless solid [22.5 g, 68.7 mmol, 65%]. Characterization data of this compound were in accordance with the values reported above.

HPLC Determination of Enantioselectivity for Carboamination Reaction

A small sample of carboamination reaction mixture, before methylation with Me$_2$SO$_4$, was removed and hydrolyzed with aq. HCl (1M) and extracted with CH$_2$C$_2$. The organic extract was dried over MgSO$_4$, filtered, loaded onto silica and concentrated under reduced pressure. Purification by flash chromatography (SiO$_2$, hexanes:EtOAc=3:1→2:1) afforded the product (21) as a colorless solid.

Enantiomeric ratio of 97:3 was determined by HPLC analysis using Daicel Chiracel® OJ-3 column, 25% iPrOH in hexanes, 0.8 mL/min, t$_R$(minor)=11.3 min, t$_R$(major)= 12.8 min.

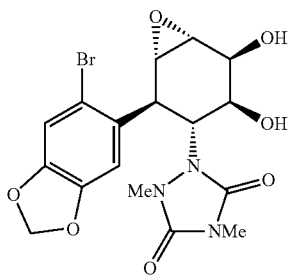

S7

Synthesis of epoxydiol S7: Epoxydiol S7 was prepared using the procedure to synthesize epoxydiol S6. Bromohydrin 25 (27.3 g, 54.3 mmol) was subjected to the reaction conditions. The residue was purified by flash chromatography (SiO$_2$, CH$_2$Cl$_2$:MeOH=30:1-15:1) to give the desired compound as a colorless solid [22.5 g, 49.3 mmol, 91%].

R$_f$=0.42 (SiO$_2$, CH$_2$Cl$_2$:MeOH=8:1); [α]$_D^{22}$=+117.9 (c=1.0 in CHCl$_3$); m.p.=158-160° C.

NMR analysis of epoxydiol S7 at 20° C. revealed several conformational isomers. Variable-temperature NMR spectroscopy was employed, and full coalescence of the peaks was observed at 100° C.

$^1$H NMR (500 MHz, DMSO-d$_6$, 20° C.) δ 7.21 (s, 0.1H), 7.16 (s, 2H), 7.14 (s, 1H), 7.01 (s, 1H), 6.68 (s, 0.1H), 6.09 (s, 2H), 6.05 (m, 2.2H), 5.74 (d, J=4.5 Hz, 1H), 5.64 (d, J=4.5 Hz, 1H), 5.38 (d, J=3.9 Hz, 0.1H), 4.93 (d, J=6.4 Hz, 2H), 4.93 (d, J=7.4 Hz, 0.1H), 4.46 (t, J=10.3 Hz, 1H), 4.32 (m, 3H), 4.25 (t, J=11.2 Hz, 0.1H), 4.13 (d, J=9.9 Hz, 1H), 3.96 (d, J=9.5 Hz, 1H), 3.84 (bs, 1H), 3.72 (d, J=11.2 Hz, 0.1H), 3.60 (t, J=10.3 Hz, 1H), 3.29 (m, 0.1H), 3.22 (s, 3H), 2.96 (bs, 1H), 2.91 (bs, 1H), 2.87 (s, 3H), 2.85 (s, 0.3H), 2.78 (s, 3H), 2.49 (s, 0.3H), 2.44 (s, 3H).

$^1$H NMR (500 MHz, DMSO-3$_6$, 100° C.) δ 7.10 (s, 2H), 6.04 (d, J=13.25, 2H), 5.28 (bs, 2H), 4.41 (s, 2H), 4.37 (d, J=3.2 Hz, 1H), 4.08 (bs, 2H), 3.36 (t, J=3.2 Hz, 1H), 3.03-2.77 (m, 7H).

$^{13}$C NMR (126 MHz, DMSO-d$_6$, 20° C.) δ 156.1, 155.6, 154.5, 153.7, 153.3, 148.4, 148.3, 148.1, 147.9, 147.8, 147.4, 133.5, 132.6, 131.2, 114.7, 114.4, 113.9, 113.7, 112.5, 112.4, 109.3, 108.6, 102.7, 68.3, 68.2, 67.9, 66.4, 65.7, 65.1, 60.8, 60.6, 57.1, 56.3, 55.9, 55.8, 55.7, 55.6, 47.1, 43.3, 35.3, 31.6, 25.6, 25.3, 25.2.

$^{13}$C NMR (126 MHz, DMSO-d$_6$, 100° C.) δ 154.4, 154.3, 147.4, 147.1, 140.7 132.4, 113.7, 111.6, 108.4, 101.6, 67.3, 65.3, 59.5, 55.03, 55.00, 42.6, 24.4.

HRMS (ESI-TOF, m/z) calcd. For C$_{17}$H$_{18}$BrN$_3$O$_7$K [M+K]$^+$ calc.: 495.9942; Found: 495.9944.

IR (ATR, neat, cm$^{-1}$): 3409 (br), 2893 (w), 1759 (w), 1691 (s), 1480 (s), 1234 (m), 1021 (m), 1035 (m), 928 (m), 775 (m).

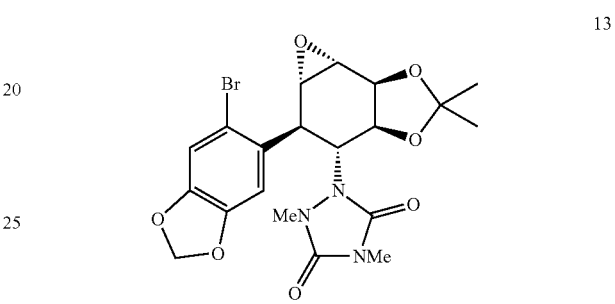

13

Synthesis of epoxyacetonide 13: Epoxyacetonide 13 was prepared using the procedure to synthesize epoxyacetonide 14. Epoxydiol S7 (22.5 g, 49.3 mmol) was subjected to the reaction conditions. The residue was purified by flash chromatography (SiO$_2$, hexanes:EtOAc=2:1→1:3) to give the desired compound as a colorless solid [21.0 g, 42.2 mmol, 86%].

R$_f$=0.52 (SiO$_2$, CH$_2$Cl$_2$:MeOH=16:1); [α]$_D^{22}$=+17.5 (c=1.0 in CHCl$_3$); m.p.=201-204° C.

NMR analysis of epoxyacetonide 13 at 20° C. revealed several conformational and rotameric isomers. Variable-temperature NMR spectroscopy was employed, and a full coalescence of the peaks was observed at 80° C.

$^1$H NMR (500 MHz, DMSO-d$_6$, 20° C.) δ 7.26 (s, 0.1H), 7.23 (bs, 1H), 7.20 (s, 0.2H), 7.12-7.01 (bs, 1H), 7.03 (s, 0.2H), 6.66 (s, 0.1H), 6.08 (d, J=7.8 Hz, 2H), 6.04 (m, 0.6H), 4.96 (dd, J=12.6, 10.4 Hz, 0.2H), 4.84 (d, J=5.2 Hz, 1H), 4.82 (d, J=5.9 Hz, 0.2H), 4.62 (m, 0.1H), 4.52-4.36 (bs, 1H), 4.25 (dd, J=10.4, 5.9 Hz, 0.2H), 4.13 (dd, J=12.2, 9.9 Hz, 0.1H), 3.75-3.62 (bs, 1H), 3.63 (m, 0.3H), 3.59 (s, 0.1H), 3.56 (s, 0.1H), 3.54 (s, 0.1H), 3.50 (bs, 1H), 3.47 (d, J=3.4 Hz, 0.2H), 3.42 (s, 0.1H), 3.39 (s, 0.1H), 3.33 (s, 0.1H), 3.16 (s, 1H), 3.15 (bs, 1H), 3.00-2.89 (bs, 3H), 2.84 (s, 0.3H), 2.82 (s, 3H), 2.72 (s, 0.3H), 2.68 (s, 0.6H), 1.47 (s, 0.6H), 1.44 (m, 4H), 1.35 (s, 0.3H), 1.32 (s, 3H).

$^1$H NMR (500 MHz, DMSO-d$_6$, 80° C.) δ 7.15 (s, 1H), 7.07-6.99 (bs, 1H), 6.04 (d, J=6.0 Hz, 2H), 4.81 (d, J=5.5 Hz, 1H), 4.52-4.43 (bs, 1H), 4.21-4.11 (bs, 1H), 3.75-3.66 (bs, 1H), 3.52-3.45 (bs, 1H), 3.20-3.10 (bs, 1H), 2.99-2.89 (bs, 3H), 2.81 (s, 3H), 1.47 (s, 3H), 1.34 (s, 3H).

$^{13}$C NMR (126 MHz, DMSO-d$_6$, 20° C.) δ 155.7, 155.5, 155.1, 154.0, 153.2, 153.3, 148.0, 147.7 147.6, 147.4, 147.1, 146.6, 130.6, 129.8, 129.7, 114.7, 113.6, 113.5, 113.1, 112.8, 112.4, 110.2, 109.9, 109.7, 108.6, 102.3, 102.2, 102.1, 73.0, 72.9, 72.8, 72.7, 72.6, 59.5, 58.6, 57.8, 57.6, 57.4, 57.3, 53.0, 52.8, 51.6, 45.2, 44.2, 43.3, 36.0, 32.1, 28.02, 27.5, 27.3, 26.2, 25.7, 25.2, 25.0, 24.8.

$^{13}$C NMR (126 MHz, DMSO-d$_6$, 80° C.) δ 155.1, 154.8, 147.4, 147.2, 130.5, 112.1, 109.7, 108.4, 107.9, 101.9, 72.9, 72.5, 59.7, 58.2, 51.5, 43.1, 34.4, 27.1, 25.5, 24.8.

HRMS (ESI-TOF, m/z) calcd. For C$_{20}$H$_{22}$BrN$_3$O$_7$K [M+K]$^+$ calc.: 536.0255; Found: 536.0231.

IR (ATR, neat, cm$^{-1}$): 2924 (w), 1768 (w), 1704 (s), 1479 (s), 1235 (s), 1219 (s), 1034 (s), 927 (m), 774 (m).

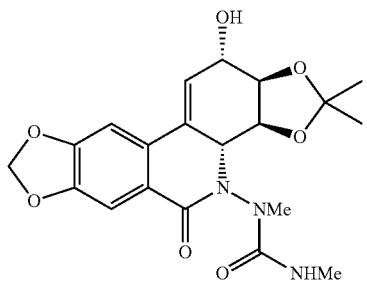

36

Synthesis of lactam 36: Lactam 36 was prepared using the procedure to synthesize lactam reaction conditions. The residue was purified by flash chromatography (SiO$_2$, CH$_2$Cl$_2$:MeOH=50:1→30:1) to give the desired compound as a white solid [12.4 g, 29.8 mmol, 70%].

R$_f$=0.46 (SiO$_2$, CH$_2$Cl$_2$:MeOH=8:1); [α]$_D^{22}$-24.1 (c=1.0 in EtOH); m.p.=150-155° C. decomposition.

NMR analysis of lactam 36 at 20° C. revealed several conformational isomers. When variable-temperature NMR spectroscopy was employed no coalescence of the peaks was observed. Only the two major isomers are described for clarity.

$^1$H NMR (500 MHz, CDCl$_3$) δ 7.51 (s, 1H), 7.48 (s, 0.5H), 7.00 (s, 1H), 6.89 (s, 0.5H), 6.41 (t, J=3.0 Hz, 1H), 6.34 (t, J=3.2 Hz, 0.5H), 6.03 (s, 2H), 5.99 (d, J=8.4 Hz, 1H), 5.10 (d, J=4.9 Hz, 1H), 4.66 (d, J=4.7 Hz, 0.5H), 4.62 (m, 0.5H), 4.51 (m, 2H), 4.33 (t, J=7.7 Hz, 0.5H), 4.29-4.23 (m, 1.5H), 4.04 (m, 1.5H), 3.74 (s, 0.5H), 3.46 (s, 1H), 3.28 (s, 1.5H), 3.12 (s, 3H), 2.81 (d, J=4.7 Hz, 1.5H), 2.76 (d, J=4.9 Hz, 3H), 1.48 (s, 4.5H), 1.35 (s, 1.5H), 1.32 (s, 3H).

$^{13}$C NMR (126 MHz, CDCl$_3$) δ 163.0, 162.2, 158.8, 157.5, 152.6, 152.1, 148.8, 148.5, 129.3, 128.6, 127.6, 127.4, 126.7, 126.3, 120.5, 120.3, 111.3, 110.4, 107.9, 107.8, 102.3, 102.2, 101.8, 101.3, 79.4, 78.6, 78.5, 76.6, 72.2, 71.4, 63.1, 61.0, 38.6, 31.9, 27.7, 27.5, 27.4, 27.2, 24.9, 24.8.

HRMS (ESI-TOF, m/z) calcd. For C$_{20}$H$_{23}$N$_3$O$_7$Na [M+Na]$^+$ calc.: 440.1428; Found: 440.1434.

IR (ATR, neat, cm$^{-1}$): 3380 (br), 2987 (w), 2916 (w), 1655 (s), 1535 (m), 1481 (s), 1259 (s), 1063 (m), 1035 (m), 764 (s), 750 (s).

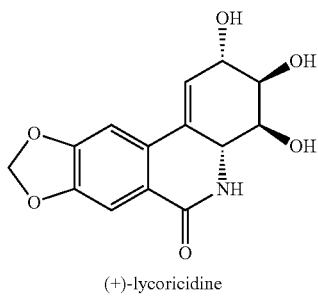

(3)

(+)-lycoricidine

Synthesis of (+)-lycoricidine (3): To a stirred solution of lactam 36 (12.4 g, 29.7 mmol, 1.0 solution of SmI$_2$ (595 mL, 0.1 M in THF, 59.5 mmol, 2.0 equiv.) over 30 min. Then aq. HCl (500 mL, 6.0 M) was added and the resulting solution was stirred until complete conversion as judged by TLC. The (+)-lycoricidine (3) solution was then carefully neutralized with solid NaHCO$_3$ (250 g). The resulting suspension was filtered and concentrated under reduced pressure. The residue was purified by flash chromatography (wet loaded with DMSO and purified using Cis-functionalized SiO$_2$, H$_2$O:MeOH=1:0→5:1) to give lycoricidine as a colorless solid [8.10 g, 27.8 mmol, 94%]. Characterization data of (+)-lycoricidine (3) were in accordance with the literature values.

R$_f$=0.38 (SiO$_2$, CHCl$_3$:MeOH=4:1); [α]$_D^{22}$=+178.2 (c=0.45 in C$_5$H$_5$N); [α]$_D^{22}$=+157.2 (c=1.0 in DMSO); Reported Values: Lit [α]$_D^{20}$=+180 (c=0.45 in C$_5$H$_5$N) (Liebigs Ann. Chem. 1983, 535); Lit [α]$_D^{20}$=+182 (c=0.45 in C$_5$H$_5$N) (Org. Lett., 2010, 12, 2544); m.p.=216-218° C. decomposition.

$^1$H NMR (500 MHz, DMSO-d$_6$) δ 7.32 (s, 1H), 7.26 (s, 1H), 7.20 (s, 1H), 6.12 (m, 3H), 5.19 (m, 2H), 4.99 (d, J=3.8 Hz, 1H), 4.19 (ddd, J=8.6, 2.5, 1.3 Hz, 1H), 4.06-4.02 (bs, 1H), 3.79 (ddd, J=8.6, 5.6, 2.2 Hz, 1H), 3.73-3.69 (bs, 1H).

$^{13}$C NMR (126 MHz, DMSO-d$_6$) δ 163.2, 151.0, 147.2, 131.8, 130.0, 123.7, 121.9, 106.2, 103.4, 101.9, 72.6, 69.3, 69.2, 52.8 HRMS (ESI-TOF, m/z) calcd. For C$_{14}$H$_{14}$N$_{06}$ [M+H]$^+$ calc.: 292.0816; Found: 292.0815.

IR (ATR, neat, cm$^{-1}$): 3274 (br), 2918 (m), 1661 (s), 1472 (s), 1392 (s), 1275 (m), 1086 (s), 1027 (s).

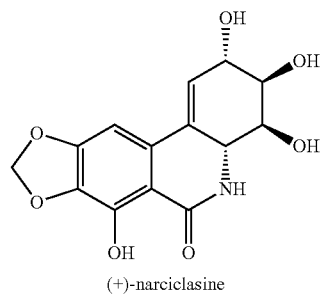

(4)

(+)-narciclasine

Synthesis of (+)-narciclasine (4) from lycoricidine (3): To (+)-lycoricidine (3) (3.00 g, 10.3 mmol, 1.0 equiv.) was added MeCN (60 mL), HMDS (65 mL, 309 mmol, 30 equiv.), and TFA (7.9 μL, 0.10 mmol, 1.0 mol %), and the resulting mixture was stirred at 25° C. for 2 h under an inert atmosphere. The volatiles were then removed under reduced pressure, and trace amounts of HMDS remaining were completely removed by azeotropic co-evaporation using toluene (3×60 mL). The flask containing leftover residue was flushed with nitrogen and sealed with rubber septa. THF (31 mL) was introduced and the resulting solution was cooled to −78° C. Then, freshly prepared (TMP)$_2$Cu(CN)Li$_2$ (106 mL, 0.195 M in THF, 20.6 mmol, 2.0 equiv.) was added, and the mixture was warmed to 0° C., and further stirred for 2 h at this temperature. The reaction was cooled again to −78° C. and tBuOOH (3.7 mL, 5.5 M in decane, 20.6 mmol, 2.0 equiv.) was added dropwise. After stirring the resulting mixture for 30 min, the reagents were quenched with mixture of sat. aq. NH$_4$Cl and 10% aq. Na$_2$S203 (50 mL, 1:1), then warmed to room temperature. The phases were separated, and the aqueous phase was extracted with EtOAc (4×50 mL). A mixture of CF₃COOH:MeOH (100 mL, 1:1) was added to the combined organic extracts and volatiles were removed under reduced pressure. The residue was recrystallized from a H₂O and MeOH mixture and then purified by flash chromatography (wet loaded with DMSO and purified using $C_{18}$-functionalized $SiO_2$, H₂O:MeCN=1:0→5:1) to give (+)-narciclasine (4) as a colorless solid [1.80 g, 5.86 mmol, 57%], as well as recovered lycoricidine [3, 0.43 g, 1.47 mmol, 14%]. Characterization data of this compound were in accordance with the values reported above.

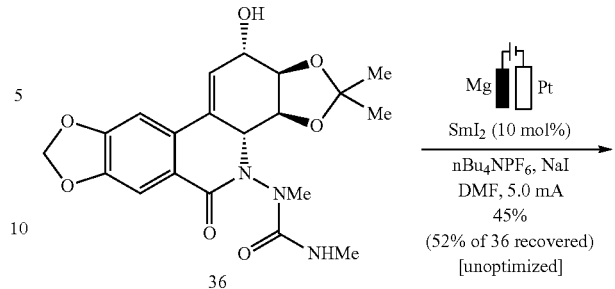

36

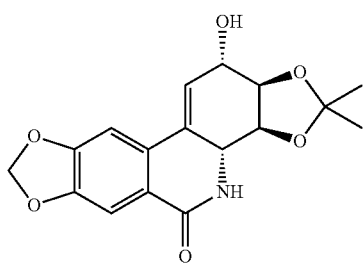

37

Synthesis of (−)-lycoricidine 3,4-acetonide 37: To a stirred solution of lactam 36 (1.00 g, 2.4 mmol, 1.0 equiv.), in degassed MeOH (32 mL) at 0° C. was added dropwise a solution of SmI₂ (48.0 mL, 0.1 M in THF, 4.8 mmol, 2.0 equiv.) over 30 min. Then sat. aq. Rochelle's Salt (25 mL) was added and the resulting solution was diluted with H₂O (100 mL). The phases were separated, and the aqueous phase was extracted with EtOAc (4×150 mL). The combined organic layers were dried over MgSO₄, filtered and concentrated under reduced pressure. The residue was purified by flash chromatography (SiO₂, CH₂Cl₂:MeOH=60:1→40:1) to give the desired compound as a colorless solid [667 mg, 2.0 mmol, 83%]. Characterization data of (−)-lycoricidine 3,4-acetonide 37 were in accordance with the literature values. Optical purity of 97:3 was determined by HPLC analysis using Daicel Chiracel® OJ-3 column, 10% iPrOH in hexanes, 1.0 mL/min, $t_R$(major)=22.3 min, $t_R$(minor)=28.8 min.

$R_f$=0.54 (SiO₂, CH₂Cl₂:MeOH=8:1); $[\alpha]_D^{22}$=−33.3 (c=0.76 in MeOH); Reported Values: Lit $[\alpha]_D^{22}$=−34.3 (c=0.76 in MeOH) (J. Am. Chem. Soc., 1999, 121, 5176); Lit $[\alpha]_D^{25}$=−32.6 (c=0.61 in MeOH) (J. Nat. Prod., 2006, 69, 7); m.p.=233-236° C. decomposition.

¹H NMR (500 MHz, CDCl₃) δ 7.53 (s, 1H), 6.96 (s, 1H), 6.23-6.21 (m, 1H), 6.20-6.17 (m, 1H), 5.98-5.95 (m, 2H), 4.34-4.31 (m, 1H), 4.10-4.04 (m, 3H), 2.91-2.55 (bs, 1H), 1.46 (s, 3H), 1.32 (s, 3H).

¹³C NMR (126 MHz, CDCl₃) δ 162.5, 151.9, 148.8, 128.5, 127.7, 124.0, 121.0, 111.6, 107.8, 102.1, 101.6, 79.7, 79.0, 73.0, 56.1, 27.2, 24.9.

HRMS (ESI-TOF, m/z) calcd. For $C_{17}H_{18}NO_6$ [M+H]⁺ calc.: 332.1129; Found: 332.1130.

IR (ATR, neat, cm⁻¹): 3323 (br), 2904 (w), 1652 (s), 1614 (m), 1473 (s), 1378 (m), 1254 (s), 1023 (s), 878 (m), 772 (s).

Electrochemical Cleavage of N—N bond: For the catalytic SmI₂-mediated N—N bond cleavage, the following literature procedure was employed (J. Am. Chem. Soc. 2018, 140, 7913): Lactam 36 (100 mg, 0.24 mmol, 1.0 equiv.), NaI (71.0 mg, 0.48 mmol, 2.0 equiv.) and nBu₄NPF₆ (186 mg, 0.48 mmol, 2.0 equiv.) in degassed DMF (4.8 mL) were added to an undivided cell, with a magnesium anode (7 mm×52 mm×1 mm) and a platinum cathode (7 mm×52 mm×1 mm). Then SmI₂ (0.1 M in THF, 0.24 mL, 10 mol %) was added dropwise while stirring. At 25° C., electrolysis was started with a constant current of 5.0 mA which was maintained for 3 days. Then, H₂O (4.8 mL) was added to the mixture. The resulting slurry was filtrated through a celite pad, which was washed with EtOAc (40 mL×3). The combined organic phases were washed with H₂O (20.0 mL), brine (20.0 mL) then dried over MgSO₄, filtered and concentrated under reduced pressure. The residue was purified by flash chromatography (SiO₂, CH₂Cl₂:MeOH=60:1→40:1) to give the desired compound as a colorless solid [36.2 mg, 0.11 mmol, 45%] as well as recovered starting material 36 [51.9 mg, 0.12 mmol, 52%]. Characterization data of this compound were in accordance with the values reported above.

Example 8. C-7 Functionalization of (+)-Lycoricidine (3)

General Procedure for the C-7 Functionalization of (+)-Lycoricidine (3):

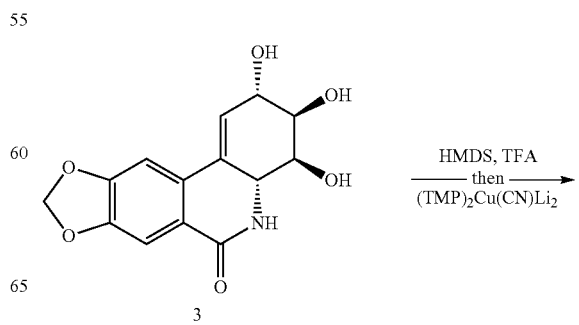

3

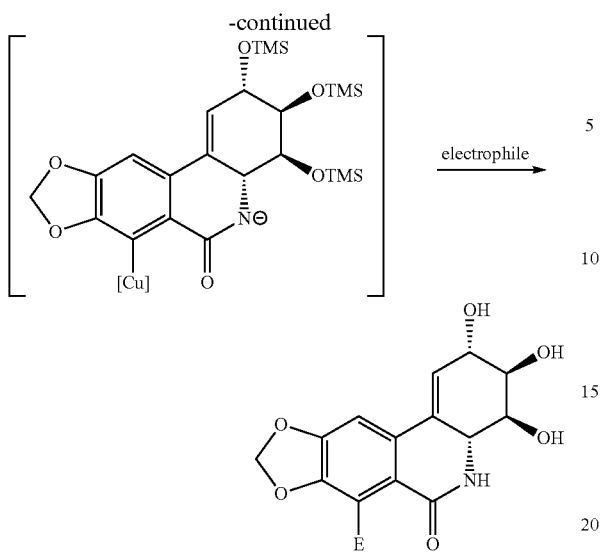

R$_f$=0.46 (SiO$_2$, CHCl$_3$:MeOH=4:1); [α]$_D^{23}$=+127.1 (c=1.0 in MeOH); m.p.=88-91° C. decomposition.

$^1$H NMR (500 MHz, DMSO-d$_6$) δ 7.18 (s, 1H), 7.11 (s, 1H), 6.11-6.09 (m, 1H), 6.08-6.06 (m, 2H), 5.97 (ddt, J=16.7, 10.1, 6.3 Hz, 1H), 5.17 (t, J=6.3 Hz, 2H), 5.01-4.85 (m, 3H), 4.09-4.00 (m, 2H), 3.90 (dd, J=13.7, 6.8 Hz, 1H), 3.80-3.76 (m, 1H), 3.78-3.69 (m, 1H), 3.71-3.66 (m, 1H).

$^{13}$C NMR (126 MHz, DMSO-d$_6$) δ 164.1, 149.3, 147.0, 136.8, 133.3, 131.4, 123.4, 122.1, 119.6, 114.9, 102.4, 101.6, 72.5, 69.3, 69.2, 52.6, 30.7.

HRMS (ESI-TOF, m/z) calcd. For C$_{17}$H$_{18}$NO$_6$ [M+H]$^+$ calc.: 332.1134; Found: 332.1125.

IR (ATR, neat, cm$^{-1}$): 3277 (br), 2909 (w), 1638 (s), 1605 (m), 1466 (s), 1382 (m), 1224 (m), 1019 (s), 931 (m).

To (+)-lycoricidine (3) (100 mg, 343 μmol, 1.0 equiv.) was added MeCN (2.2 mL), HMDS (2.2 mL, 10.3 mmol, 30 equiv.), and TFA (2.6 μL, 34.3 μmol, 10 mol %), and the resulting mixture was stirred at 25° C. for 30 minutes under an inert atmosphere. The volatiles were then removed under reduced pressure, and trace amounts of HMDS remaining were completely removed by azeotropic co-evaporation using toluene (3×4.0 mL). The flask containing leftover residue was flushed with nitrogen and sealed with rubber septa. THF (1.0 mL) was introduced and the resulting solution was cooled to −78° C. Then freshly prepared (TMP)$_2$Cu(CN)Li$_2$ (3.52 mL, 0.195 M in THF, 686 μmol, 2.0 equiv.) was added, and the mixture was warmed to 0° C. After stirring the reaction mixture for 2 h at this temperature, the electrophile (1.7 mmol, 5.0 equiv.) was added dropwise and solution was stirred until complete conversion as judged by TLC, then a mixture of sat. aq. NH$_4$Cl and 10% aq. Na$_2$S$_2$O$_3$ (3 mL, 1:1) was added. Upon warming to room temperature, the phases were separated and the aqueous phase was extracted with EtOAc (4×10 mL). A mixture of CF$_3$COOH:MeOH (10 mL, 1:1) was added to the combined organic extracts and volatiles were removed under reduced pressure. The product was purified by flash chromatography (either SiO$_2$ or C$_{18}$-functionalized SiO$_2$).

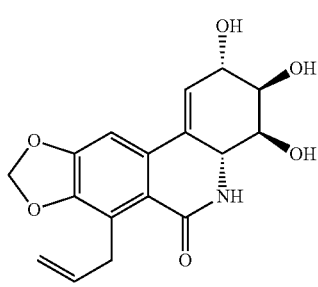 [SMILES: C=CCc1c2c(cc3c1C(=O)N[C@@H]1C3=C[C@H](O)[C@@H](O)[C@H]1O)OCO2]

7-allyl lycoricidine 38: Following the general procedure, with allylbromide as an electrophile, the title compound was purified by flash chromatography (SiO$_2$, CH$_2$Cl$_2$:MeOH=20:1→8:1) to yield a yellow solid [79.0 mg, 237 μmol, 69%].

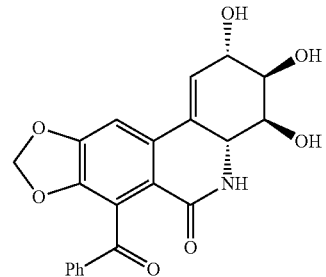 [SMILES: O=C1N[C@@H]2C(=C[C@H](O)[C@@H](O)[C@H]2O)c2cc3c(c(C(=O)c4ccccc4)c21)OCO3]

7-oxophenyl lycoricidine 39: Following the general procedure, with benzoylchloride as an electrophile, the title compound was purified by flash chromatography (SiO$_2$, CH$_2$Cl$_2$:MeOH=20:1→8:1) to yield a colorless solid [114.0 mg, 289 μmol, 84%].

R$_f$=0.43 (SiO$_2$, CHCl$_3$:MeOH=4:1); [α]$_D^{24}$=+138.2 (c=1.0 in MeOH); m.p.=180-184° C. decomposition.

NMR analysis of 7-oxophenyl lycoricidine 39 at 20° C. revealed two conformational isomers.

When variable-temperature NMR spectroscopy was employed no coalescence of the peaks was observed.

$^1$H NMR (500 MHz, DMSO-d$_6$) δ 7.71-7.65 (m, 2H), 7.61-7.55 (m, 1H), 7.50-7.45 (m, 2H), 7.40 (s, 1H), 7.24 (s, 1H), 6.27-6.24 (m, 1H), 6.14-6.03 (m, 2H), 5.43-5.00 (m, 3H), 4.24-4.19 (m, 1H), 4.12-4.08 (m, 1H), 3.79 (d, J=8.5 Hz, 1H), 3.75-3.72 (m, 1H)

$^{13}$C NMR (126 MHz, DMSO-d$_6$) δ 192.6, 191.7, 162.8*, 151.5, 151.1, 145.8, 145.0, 137.5, 137.2, 133.2, 133.0, 132.9, 132.4, 130.2, 130.0, 128.8*, 128.6, 128.2, 125.1*, 121.4, 120.7, 120.7*, 104.2, 104.1 102.9*, 72.7*, 69.3*, 69.2*, 53.0, 52.8. (* Overlap of 2 peaks) HRMS (ESI-TOF, m/z) calcd. For C$_{21}$H$_{18}$NO$_7$ [M+H]$^+$ calc.: 396.1083; Found: 396.1095.

IR (ATR, neat, cm$^{-1}$): 3309 (br), 2921 (w), 1650 (s), 1596 (m), 1461 (m), 1391 (m), 1246 (s), 1032 (s), 1018 (s), 927 (m).

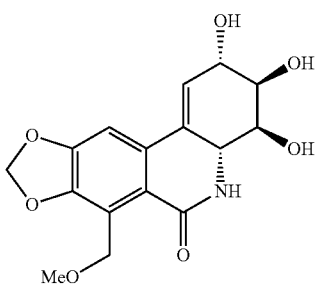 [SMILES: COCc1c2c(cc3c1C(=O)N[C@@H]1C3=C[C@H](O)[C@@H](O)[C@H]1O)OCO2]

40

7-methoxymethyl lycoricidine 40: Following the general procedure, with chloromethyl methyl ether as an electrophile, the title compound was purified by flash chromatography (SiO$_2$, CH$_2$Cl$_2$:MeOH=20:1→8:1) to yield a yellow solid [87.0 mg, 261 μmol, 76%].

R$_f$=0.36 (SiO$_2$, CHCl$_3$:MeOH=4:1); [α]$_D^{24}$=+75.5 (c=1.0 in MeOH); m.p.=122-125° C. decomposition.

$^1$H NMR (500 MHz, DMSO-d$_6$) δ 7.45 (s, 1H), 7.17 (s, 1H), 6.16-6.13 (m, 1H), 6.11-6.05 (m, 2H), 5.61 (d, J=6.3 Hz, 1H), 5.30 (d, J=5.5 Hz, 1H), 5.12 (d, J=10.2 Hz, 1H), 5.06 (d, J=3.4 Hz, 1H), 4.61 (d, J=10.2 Hz, 1H), 4.06-4.01 (m, 2H), 3.82-3.74 (m, 1H), 3.71-3.69 (m, 1H), 3.22 (s, 3H).

$^{13}$C NMR (126 MHz, DMSO-d$_6$) δ 163.1, 149.5, 147.8, 133.2, 131.4, 123.6, 120.5, 119.6, 103.7, 101.8, 72.6, 69.14, 69.11, 64.7, 57.6, 52.9.

HRMS (ESI-TOF, m/z) calcd. For C$_{16}$H$_{18}$NO$_7$ [M+H]$^+$ calc.: 336.1083; Found: 336.1095.

IR (ATR, neat, cm$^{-1}$): 3380 (br), 3275 (br), 2922 (w), 1643 (s), 1608 (m), 1469 (s), 1395 (m), 1230 (m), 1016 (s), 927 (w).

IR (ATR, neat, cm$^{-1}$): 3265 (br), 2922 (m), 1646 (s), 1608 (m), 1464 (s), 1387 (m), 1228 (m), 1032 (s), 938 (w).

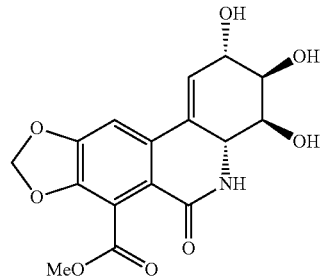

42

7-carboxymethyl lycoricidine 42: Following the general procedure, with methyl chloroformate as an electrophile, the title compound was purified by flash chromatography (C$_{18}$-functionalized SiO$_2$, H$_2$O:MeCN=1:0→5:1) to yield a colorless solid [93.0 mg, 265 μmol, 77%].

R$_f$=0.41 (SiO$_2$, CHCl$_3$:MeOH=4:1); [α]$_D^{23}$=+206.7 (c=1.0 in DMSO); m.p.=201-205° C. decomposition.

$^1$H NMR (500 MHz, DMSO-d$_6$) δ 7.38 (s, 1H), 7.34 (s, 1H), 6.22-6.17 (m, 1H), 6.19-6.15 (m, 2H), 5.27-5.17 (m, 2H), 5.02 (s, 1H), 4.17-4.12 (m, 1H), 4.07-4.00 (m, 1H), 3.80-3.77 (m, 1H), 3.75 (s, 3H), 3.73-3.68 (m, 1H).

$^{13}$C NMR (126 MHz, DMSO-d$_6$) δ 165.6, 162.2, 150.9, 145.1, 132.4, 129.8, 124.9, 119.2, 114.8, 104.1, 102.8, 72.5, 69.1, 69.0, 52.7, 52.3.

HRMS (ESI-TOF, m/z) calcd. For C$_{16}$H$_{16}$NO$_8$ [M+H]$^+$ calc.: 350.0876; Found: 350.0870.

IR (ATR, neat, cm$^{-1}$): 3379 (s), 3359 (s), 3228 (br), 2904 (w), 1716 (m), 1650 (m), 1607 (m), 1470 (m), 1398 (m), 1256 (m), 1030 (s), 1014 (s), 915 (w).

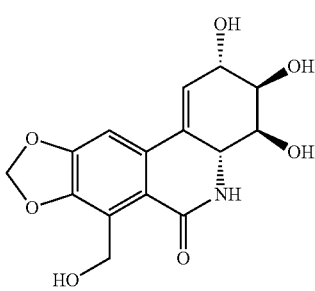 [SMILES: O=C1N[C@@H]2C(=C[C@H](O)[C@@H](O)[C@H]2O)c2cc3c(c(CO)c21)OCO3]

41

7-hydroxymethyl lycoricidine 41: Following the general procedure, with 2-(trimethylsilyl) ethoxymethyl chloride as an electrophile, the crude material was stirred in neat TFA (5.0 mL) for 2 hours before concentration and purification by flash chromatography (SiO$_2$, CH$_2$Cl$_2$:MeOH=20:1→8:1) to yield a colorless solid [80.0 mg, 248 μmol, 72%].

R$_f$=0.37 (SiO$_2$, CHCl$_3$:MeOH=4:1); [α]$_D^{23}$=+99.2 (c=1.0 in MeOH); m.p.=157-162° C. decomposition.

$^1$H NMR (500 MHz, DMSO-d$_6$) δ 7.81 (s, 1H), 7.24 (s, 1H), 6.20-6.13 (m, 3H), 5.43-5.21 (m, 3H), 5.12-5.02 (bs, 1H), 4.68-4.58 (m, 2H), 4.13 (d, J=8.5 Hz, 1H), 4.09 (m, 1H), 3.86 (d, J=8.5 Hz, 1H), 3.77-3.74 (m, 1H).

$^{13}$C NMR (126 MHz, DMSO-d$_6$) δ 165.4, 150.0, 146.6, 133.7, 130.8, 124.2, 122.8, 120.3, 103.4, 101.8, 72.5, 69.1, 68.9, 55.5, 52.7.

HRMS (ESI-TOF, m/z) calcd. For C$_{15}$H$_{16}$NO$_7$ [M+H]$^+$ calc.: 322.0927; Found: 322.0938.

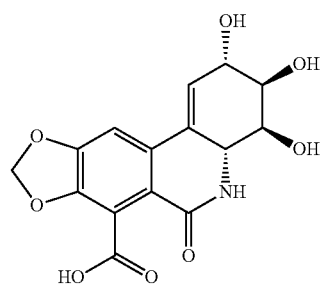

43 lycoricidine-7-carboxylic acid 43: To solution of 42 (25.0 mg, 71.6 μmol, 1.0 equiv.) in H$_2$O (5.0 mL) was added aq. NaOH (5 mL, 2.0 M) and the reaction was stirred for 2 hours at 25° C. The resulting solution was then neutralized to pH 7 with HCl (1.8 mL, 6.0 M) and was concentrated under reduced pressure. The residue was purified by flash chromatography (wet loaded with H$_2$O and purified using C$_{18}$-functionalized SiO$_2$, H$_2$O:MeCN=1:0→5:1) to give a yellow solid [13.0 mg, 39.9 μmol, 56%].

R$_f$=0.75 (C$_{18}$-functionalized S102, H$_2$O:MeOH=2:1); [α]$_D^{22}$=+169.5 (c=0.5 in DMSO); m.p.=175-182° C. decomposition.

$^1$H NMR (500 MHz, D$_2$O) δ 7.08 (s, 1H), 6.20-6.14 (m, 1H), 6.04 (d, J=8.9 Hz, 2H), 4.36-4.29 (m, 2H), 4.00-3.94 (m, 2H).

$^{13}$C NMR (126 MHz, D$_2$O) δ 173.5, 166.1, 152.2, 145.4, 132.97, 132.95, 122.4, 121.2, 117.8, 104.1, 103.5, 73.2, 69.8, 69.6, 52.7.

HRMS (ESI-TOF, m/z) calcd. For $C_{15}H_{14}NO_8$ [M+H]$^+$ calc.: 336.0719; Found: 336.0718.

IR (ATR, neat, cm$^{-1}$): 3163 (br), 3047 (br), 2921 (m), 1645 (s), 1602 (m), 1569 (s), 1461 (s), 1391 (s), 1253 (m), 1080 (m), 1022 (s).

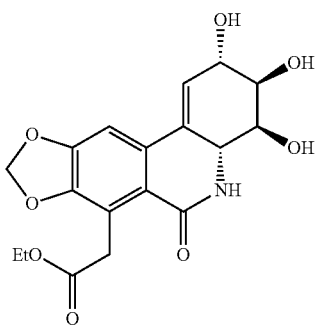

44 ethyl 2-(7-lycoricidinyl)acetate 44: Following the general procedure, with ethyl bromoacetate as an electrophile, the title compound was purified by flash chromatography (SiO$_2$, CH$_2$Cl$_2$:MeOH=20:1→8:1) to yield a colorless solid [75.0 mg, 199.8 μmol, 58%].

$R_f$=0.48 (SiO$_2$, CHCl$_3$:MeOH=4:1); $[\alpha]_D^{23}$=+128.0 (c=1.0 in MeOH); m.p.=122-126° C. decomposition.

$^1$H NMR (500 MHz, DMSO-d$_6$) δ 7.20-7.18 (m, 2H), 6.41-6.04 (m, 3H), 5.32-4.90 (m, 3H), 4.11-3.98 (m, 5H), 3.90 (d, J=16.7 Hz, 1H), 3.80-3.76 (m, 1H), 3.72-3.70 (m, 1H), 1.17 (t, J=7.1 Hz, 3H).

$^{13}$C NMR (126 MHz, DMSO-d$_6$) δ 169.9, 164.2, 149.3, 147.5, 132.9, 130.9, 123.8, 119.9, 116.5, 102.9, 101.8, 72.5, 69.3, 69.2, 59.9, 52.6, 32.7, 14.1.

HRMS (ESI-TOF, m/z) calcd. For $C_{18}H_{20}NO_8$ [M+H]$^+$ calc.: 378.1189; Found: 378.1184.

IR (ATR, neat, cm$^{-1}$): 3303 (br), 2922 (m), 1716 (m), 1647 (m), 1608 (m), 1469 (m), 1386 (m), 1256 (m), 1053 (m), 1032 (s), 1017 (s), 931 (m).

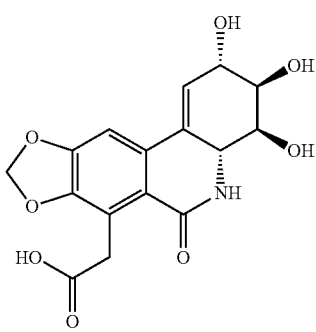

45

2-(7-lycoricidinyl)acetic acid 45: To solution of 44 (25.0 mg, 68.8 μmol, 1.0 equiv.) in H$_2$O (5 mL) was added was added aq. NaOH (5 mL, 2.0 M) and the reaction was stirred for 2 hours at 25° C. The resulting solution was then neutralized to pH 7 with HCl (1.8 mL, 6.0 M) and was concentrated under reduced pressure. The residue was purified by flash chromatography (wet loaded with H$_2$O and purified using C$_{18}$-functionalized SiO$_2$, H$_2$O:MeCN=1:0→5:1) to give a colorless solid [14.2 mg, 44.5 μmol, 65%].

$R_f$=0.69 (C$_{18}$-functionalized S102, H$_2$O:MeOH=2:1); $[\alpha]_D^{22}$=+46.2 (c=0.5 in DMSO); m.p.=188-195° C. decomposition.

$^1$H NMR (500 MHz, D$_2$O) δ 7.11 (s, 1H), 6.29-6.16 (m, 1H), 6.13-6.05 (m, 2H), 4.41-4.38 (m, 1H), 4.34 (d, J=8.5 Hz, 1H), 4.08-3.92 (m, 4H).

$^{13}$C NMR (126 MHz, D$_2$O) δ 177.0, 167.8, 151.0, 149.1, 133.8, 133.3, 122.2, 119.6, 117.3, 104.2, 103.1, 73.0, 69.8, 69.6, 52.7, 34.2.

HRMS (ESI-TOF, m/z) calcd. For $C_{16}H_{14}NO_8$ [M-H]$^-$ calc.: 348.0719; Found: 348.0720.

IR (ATR, neat, cm$^{-1}$): 3270 (br), 2921 (m), 1645 (m), 1605 (m) 1469 (m), 1384 (m), 1287 (m), 1066 (s), 1027 (s).

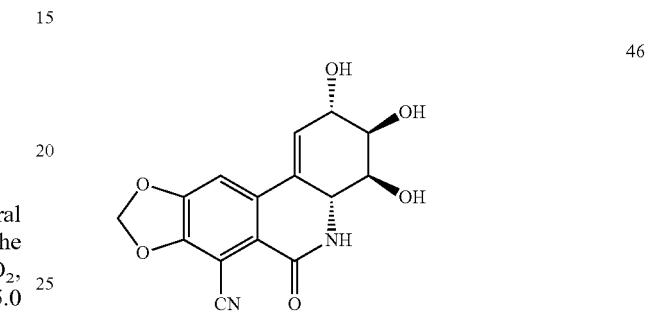

46

7-cyanolycoricidine 46: Following the general procedure, with N-fluorobenzenesulfonimide as an oxidant in place of an electrophile, the title compound was purified by flash chromatography (wet loaded with H$_2$O and purified using C$_{18}$-functionalized SiO$_2$, H$_2$O:MeOH=1:0-5:1) to yield a yellow solid [14.6 mg, 46.2 μmol, 13%]. The nitrile is believed to come from the CuCN present in the reaction.

$R_f$=0.21 (SiO$_2$, CHCl$_3$:MeOH=4:1); $[\alpha]_D^{22}$=+169.9 (c=0.5 in DMSO); m.p.=201-205° C. decomposition.

$^1$H NMR (500 MHz, DMSO-d$_6$) δ 6.77 (s, 1H), 6.72 (s, 1H), 5.50 (d, J=12.2 Hz, 2H), 5.44-5.39 (m, 1H), 4.42 (s, 2H), 4.24 (s, 1H), 3.34 (d, J=8.1 Hz, 1H), 3.25-3.19 (m, 1H), 2.97 (dd, J=8.1, 2.1 Hz, 1H), 2.88 (s, 1H).

$^{13}$C NMR (126 MHz, DMSO-d$_6$) δ 161.3, 153.4, 151.1, 133.2, 129.2, 125.9, 121.1, 113.5, 106.9, 104.0, 90.9, 72.4, 69.0, 68.9, 52.6.

HRMS (ESI-TOF, m/z) calcd. For $C_{15}H_{13}N_2O_6$ [M+H]$^+$ calc.: 317.0774; Found: 317.0776.

IR (ATR, neat, cm$^{-1}$): 3314 (br), 2918 (m), 2228 (m), 1653 (s), 1614 (m), 1469 (s), 1399 (m), 1357 (m), 1096 (m), 1028 (s), 925 (w).

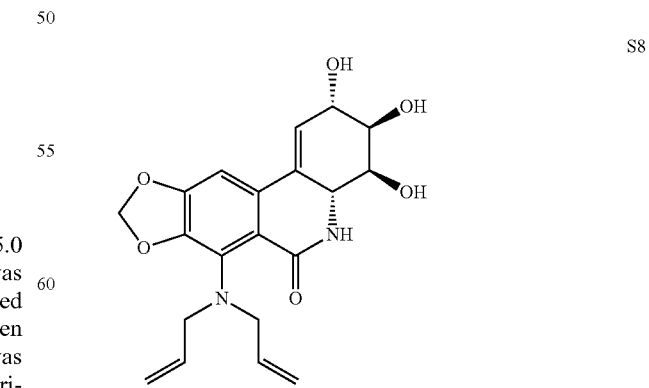

S8

N,N-diallyl-7-aminolycoricidine S8: Following the general procedure, with O-benzoyl-N,N-diallylhydroxylamine as an electrophile, the crude material was neutralized with sat. aq. NaHCO$_3$ (5 mL) before purification by flash chromatography (SiO$_2$, CH$_2$Cl$_2$:MeOH=20:1→8:1) to yield a yellow solid [87.2 mg, 226 μmol, 66%].

R$_f$=0.42 (SiO$_2$, CHCl$_3$:MeOH=4:1); [α]$_D^{23}$=+100.6 (c=1.0 in DMSO); m.p.=132-136° C. decomposition.

$^1$H NMR (500 MHz, DMSO-d$_6$) δ 7.17 (s, 1H), 6.86 (s, 1H), 6.14-6.12 (m, 1H), 6.10-6.08 (m, 1H), 5.88 (s, 1H), 5.80 (ddt, J=16.5, 10.1, 6.1 Hz, 2H), 5.15 (dd, J=16.5, 2.0 Hz, 2H), 5.02 (dd, J=10.1, 2.0 Hz, 2H), 5.23-4.87 (br, 3H), 4.03-4.01 (m, 1H), 3.94 (d, J=7.9 Hz, 1H), 3.85-3.77 (m, 3H), 3.70 (d, J=6.0 Hz, 1H), 3.69-3.65 (m, 2H).

$^{13}$C NMR (126 MHz, DMSO-d$_6$) δ 163.6, 150.0, 141.6, 136.3, 133.8, 133.4, 132.6, 122.2, 116.9, 116.4, 100.7, 97.8, 72.5, 69.2, 69.2, 54.8, 52.7.

HRMS (ESI-TOF, m/z) calcd. For C$_{20}$H$_{23}$N$_2$O$_6$ [M+H]$^+$ calcd.: 387.1556; Found: 387.1552.

IR (ATR, neat, cm$^{-1}$): 3267 (br), 2891 (m), 1635 (s), 1594 (m), 1471 (m), 1344 (s), 1307 (m), 1222 (m), 1081 (s), 1031 (s), 919 (s).

47

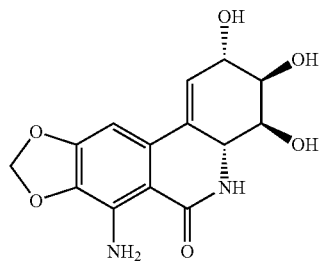

7-aminolycoricidine 47: (+)-N,N-diallyl-7-aminolycoricidine S8 (20.0 mg, 51.8 μmol, 1.0 equiv.), Pd(PPh$_3$)$_4$ (1.20 mg, 1.03 μmol, 2.0 mol %), and 1,3-dimethylbarbituric acid (48.5 mg, 311 μmol, 6.0 equiv.) were dissolved in CH$_2$Cl$_2$ (0.2 mL) and the resulting mixture was refluxed for 16 h. After, the solution was cooled to 25° C. and the solvent was removed under reduced pressure. The residue was purified by flash chromatography (wet loaded with H$_2$O and purified using C$_{18}$-functionalized SiO$_2$, H$_2$O:MeCN=1:0→5:1) to give a yellow solid [11.2 mg, 36.6 μmol, 71%].

R$_f$=0.38 (SiO$_2$, CHCl$_3$:MeOH=4:1); [α]$_D^{23}$=+244.4 (c=0.5 in DMSO); m.p.=129-132° C. decomposition.

$^1$H NMR (500 MHz, DMSO-d$_6$) δ 6.98 (s, 1H), 6.67-6.61 (bs, 2H), 6.54 (s, 1H), 6.05-6.01 (m, 3H), 5.26-4.93 (m, 3H), 4.06 (d, J=8.3 Hz, 1H), 4.02-3.99 (m, J=3.6 Hz, 1H), 3.74 (d, J=8.3 Hz, 1H), 3.69-3.66 (m, 1H).

$^{13}$C NMR (126 MHz, DMSO-d$_6$) δ 167.0, 149.3, 134.8, 133.2, 133.1, 131.1, 123.0, 104.7, 101.2, 93.3, 72.4, 69.4, 69.3, 52.6.

HRMS (ESI-TOF, m/z) calcd. For C$_{14}$H$_{15}$N$_2$O$_6$ [M+H]$^+$ calcd.: 307.0930; Found: 307.0931.

IR (ATR, neat, cm$^{-1}$): 3315 (br), 2903 (w), 1650 (s), 1556 (m), 1465 (w), 1395 (w), 1364 (s), 1235 (m), 1086 (m) 1023 (s), 925 (w).

S9

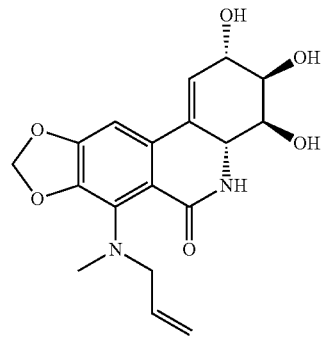

N-methyl-N-allyl-7-aminolycoricidine S9: Following the general OH procedure, with O-benzoyl-N-methyl-N-allyl-hydroxylamine as an electrophile, the crude material was neutralized with sat. aq. NaHCO$_3$CH$_2$Cl$_2$:MeOH=20:1→8:1) to yield a yellow solid [68.1 mg, 189 μmol, 55%].

R$_f$=0.40 (SiO$_2$, CHCl$_3$:MeOH=4:1); [α]$_D^{23}$=+280.4 (c=0.5 in DMSO); m.p.=113-117° C. decomposition.

$^1$H NMR (500 MHz, DMSO-d$_6$) δ 7.22 (s, 1H), 6.84 (s, 1H), 6.14-6.10 (m, 2H), 5.89 (d, J=1.1 Hz, 1H), 5.88-5.79 (m, 1H), 5.23 (dd, J=17.2, 1.8 Hz, 1H), 5.15 (d, J=5.6 Hz, 1H), 5.12-5.06 (m, 1H), 5.04 (d, J=5.6 Hz, 1H), 4.89 (d, J=3.8 Hz, 1H), 4.02 (q, J=4.6 Hz, 1H), 3.99-3.96 (m, 1H), 3.82 (ddd, J=7.8, 5.4, 2.1 Hz, 1H), 3.71 (t, J=6.9 Hz, 2H), 3.69-3.64 (m, 1H), 2.75 (s, 3H).

$^{13}$C NMR (126 MHz, DMSO-d$_6$) δ 163.6, 149.9, 140.3, 136.2, 135.8, 133.6, 132.8, 122.0, 116.7, 115.8, 100.6, 96.9, 72.5, 69.2, 69.1, 57.2, 52.8, 40.4.

HRMS (ESI-TOF, m/z) calcd. For C$_{18}$H$_{21}$N$_2$O$_6$ [M+H]$^+$ calcd.: 361.1400; Found: 361.1400.

IR (ATR, neat, cm$^{-1}$): 3285 (br), 2893 (m), 1636 (s), 1594 (m), 1490 (w), 1371 (m) 1344 (m), 1311 (m), 1225 (w), 1062 (m), 1021 (s), 934 (m).

48

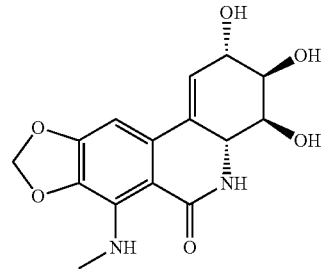

N-methyl-7-aminolycoricidine 48: Following the same procedure as compound 47, using N-methyl-N-allyl-7-aminolycoricidine S9 (60.1 mg, 166.8 μmol), the crude material was purified by flash chromatography (wet loaded with H$_2$O and purified using Cis-functionalized SiO$_2$, H$_2$O:MeCN=1:0→5:1) to give a yellow solid [31.2 mg, 97.4 μmol, 58%].

R$_f$=0.42 (SiO$_2$, CHCl$_3$:MeOH=4:1); [α]$_D^{23}$=+200.2 (c=1.0 in DMSO); m.p.=215-218° C. decomposition.

$^1$H NMR (500 MHz, DMSO-d$_6$) δ 8.51 (q, J=5.4 Hz, 1H), 7.08 (s, 1H), 6.53 (s, 1H), 6.04 (dd, J=4.9, 2.3 Hz, 1H), 5.95 (dd, J=7.3, 1.1 Hz, 2H), 5.18 (m, 2H), 4.96 (s, 1H), 4.04 (dt, J=8.2, 1.8 Hz, 1H), 4.00 (q, J=2.8 Hz, 1H), 3.74 (dd, J=8.2, 2.3 Hz, 1H), 3.67 (d, J=2.8 Hz, 1H), 3.01 (d, J=5.4 Hz, 3H).

$^{13}$C NMR (126 MHz, DMSO-d$_6$) δ 167.2, 150.6, 137.7, 133.8, 133.1, 131.1, 123.4, 105.2, 100.4, 93.6, 72.4, 69.3 69.2, 52.5, 31.5.

HRMS (ESI-TOF, m/z) calcd. For $C_{15}H_{17}N_2O_6$ [M+H]$^+$ calc.: 321.1087; Found: 321.1084.

IR (ATR, neat, cm$^{-1}$): 3280 (br), 2897 (w), 1636 (s), 1594 (w), 1519 (m), 1454 (m), 1384 (m), 1292 (m), 1230 (m), 1075 (m) 10005 (s), 935 (m).

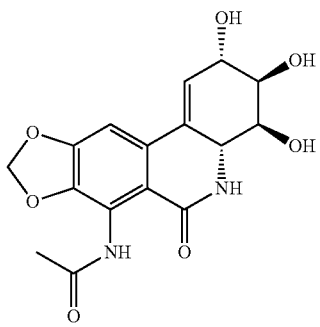

49

7-acetamidelycoricidine 49: Following the general procedure, with O-benzoyl-N-hydroxylacetamide as an electrophile, the crude material was neutralized with sat. aq. NaHCO$_3$ (5 mL) before purification by flash chromatography (wet loaded with H$_2$O and purified using C$_{18}$-functionalized SiO$_2$, H$_2$O:MeCN=1:0→5:1) to yield an colorless solid [67 mg, 190 μmol, 56%].

R$_f$=0.35 (SiO$_2$, CHCl$_3$:MeOH=4:1); [α]$_D^{23}$=+187.6 (c=0.5 in DMSO); m.p.=120-135° C. decomposition.

$^1$H NMR (500 MHz, DMSO-d$_6$) δ 10.52 (s, 1H), 7.52 (s, 1H), 7.12 (s, 1H), 6.19-6.13 (m, 1H), 6.11 (s, 1H), 6.04 (s, 1H), 5.25-5.13 (m, 2H), 4.98 (s, 1H), 4.10 (dt, J=8.3, 1.7 Hz, 1H), 4.04 (d, J=4.3 Hz, 1H), 3.80 (d, J=8.3 Hz, 1H), 3.70 (s, 1H), 2.04 (s, 3H).

$^{13}$C NMR (126 MHz, DMSO-d$_6$) δ 167.0, 165.0, 151.0, 141.4, 132.7, 130.4, 124.3, 121.5, 113.1, 101.8, 100.6, 72.4, 69.1, 69.0, 52.7, 23.4.

HRMS (ESI-TOF, m/z) calcd. For $C_{16}H_{17}N_2O_7$ [M+H]$^+$ calc.: 349.1036; Found: 349.1045.

IR (ATR, neat, cm$^{-1}$): 3278 (br), 2904 (w), 1648 (s), 1496 (m), 1476 (w), 1381 (s), 1229 (m), 1086 (m) 1026 (s), 930 (w).

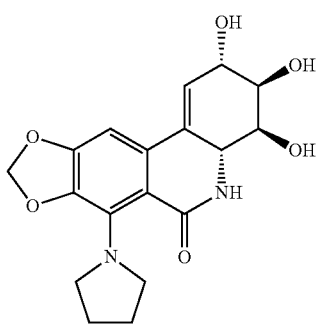

50

7-acetamideylcoricidine 49: Following the general procedure, with with O-benzoyl-N-hydroxylpyrrolidine as an electrophile, the crude material was neutralized with sat. aq. NaHCO$_3$ (5 mL) before purification by flash chromatography (SiO$_2$, CH$_2$Cl$_2$:MeOH=20:1→8:1) to yield a yellow solid [108.0 mg, 299 μmol, 87%].

R$_f$=0.37 (SiO$_2$, CHCl$_3$:MeOH=4:1); [α]$_D^{23}$=+559.0 (c=1.0 in MeOH); m.p.=155-162° C. decomposition.

$^1$H NMR (500 MHz, DMSO-d$_6$) δ 7.16 (s, 1H), 6.67 (s, 1H), 6.14-6.12 (m, 1H), 6.05 (s, 1H), 5.75 (s, 1H), 5.17-5.08 (bs, 1H), 5.05-4.98 (bs, 1H), 4.91-4.85 (bs, 1H), 4.05-4.01 (m, 1H), 3.96 (d, J=7.9 Hz, 1H), 3.84 (d, J=7.9 Hz, 1H), 3.77 (td, J=9.7, 6.8 Hz, 2H), 3.69-3.65 (m, 1H), 3.06 (dd, J=10.1, 6.8 Hz, 2H), 1.93-1.86 (m, 2H), 1.75-1.64 (m, 2H).

$^{13}$C NMR (126 MHz, DMSO-d$_6$) δ 163.8, 149.4, 135.9, 134.1, 133.8, 133.3, 121.6, 112.5, 99.6, 93.8, 72.5, 69.2, 69.1, 52.9, 51.1, 25.4.

HRMS (ESI-TOF, m/z) calcd. For $C_{18}H_{21}N_2O_6$ [M+H]$^+$ calc.: 361.1400; Found: 361.1389.

IR (ATR, neat, cm$^{-1}$): 3278 (br), 2872 (m), 1629 (s), 1589 (m), 1456 (w), 1346 (m), 1303 (m), 1223 (m), 1081 (m), 1028 (s), 938 (w).

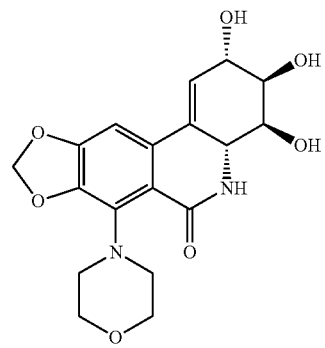

51

7-(4-morpholinyl)lycoricidine 51: Following the general procedure, with O-benzoyl-N-hydroxylmorpholine as an electrophile, the crude material was neutralized with sat. aq. NaHCO$_3$ (5 mL) before purification by flash chromatography (SiO$_2$, CH$_2$Cl$_2$:MeOH=20:1→8:1) to yield a yellow solid [107.0 mg, 286 μmol, 83%].

R$_f$=0.44 (SiO$_2$, CHCl$_3$:MeOH=4:1); [α]$_D^{23}$=+269.9 (c=1.0 in MeOH); m.p.=172-175° C. decomposition.

$^1$H NMR (500 MHz, DMSO-d$_6$) δ 7.26 (s, 1H), 6.87 (s, 1H), 6.14-6.11 (m, 2H), 5.90 (s, 1H), 5.16 (s, 1H), 5.05 (s, 1H), 4.90 (s, 1H), 4.05-4.01 (bs, 1H), 3.98 (d, J=8.1 Hz, 1H), 3.82 (d, J=8.1 Hz, 1H), 3.70-3.64 (m, 3H), 3.63-3.57 (m, 2H), 3.36-3.30 (m, 2H), 2.99-2.94 (m, 2H).

$^{13}$C NMR (126 MHz, DMSO-d$_6$) δ 163.6, 150.2, 140.2, 135.1, 133.9, 132.6, 122.3, 115.4, 100.8, 97.4, 72.5, 69.2, 69.1, 66.8, 52.8, 50.4.

HRMS (ESI-TOF, m/z) calcd. For $C_{18}H_{21}N_2O_7$ [M+H]$^+$ calc.: 377.1349; Found: 377.1338.

IR (ATR, neat, cm$^{-1}$): 3291 (br), 2886 (w), 1716 (w), 1637 (s), 1601 (m), 1469 (m), 1376 (m), 1262 (m), 1215 (m), 1096 (m) 1015 (s), 935 (w).

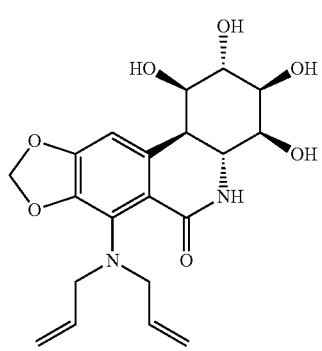

S10

7-(4-morpholinyl)lycoricidine 51: Following the general procedure, diallylaminopancratistatin S10 was prepared using the procedure to synthesize N,N-diallylaminolycoricidine S8. (+)-7-deoxypancratistatin (1) (100 mg, 0.32 mmol) was subjected to the reaction conditions. The residue was purified by flash chromatography (SiO$_2$, CH$_2$Cl$_2$:MeOH=9:1) to give the desired compound as an orange solid [60.0 mg, 0.15 mmol, 46%].

$R_f$=0.20 (SiO$_2$, CH$_2$Cl$_2$:MeOH=8:1); $[\alpha]_D^{22}$=+69.9 (c=0.5 in MeOH); m.p.=126-128° C. decomposition.

$^1$H NMR (500 MHz, CD$_3$OD) δ 6.59 (s, 1H), 6.03 (d, J=1.2 Hz, 1H), 5.90-5.79 (m, 3H), 5.15 (dq, J=17.2, 1.7 Hz, 2H), 5.02 (dt, J=10.3, 1.7 Hz, 2H), 4.41 (t, J=3.3 Hz, 1H), 4.17 (t, J=3.3 Hz, 1H), 4.00 (d, J=3.3 Hz, 1H), 3.89 (dd, J=10.3, 3.3 Hz, 1H), 3.87-3.80 (m, 2H), 3.79-3.71 (m, 3H), 3.06 (dd, J=12.6, 2.6 Hz, 1H).

$^{13}$C NMR (126 MHz, CD$_3$OD) δ 167.6, 152.3, 142.0, 138.6, 137.5*, 136.5, 119.3, 116.9*, 102.0, 100.8, 75.0, 71.9, 71.8, 70.9, 56.6*, 51.0, 43.6. (* Overlap of 2 peaks) HRMS (ESI-TOF, m/z) calcd. For C$_{20}$H$_{25}$N$_2$O$_7$ [M+H]$^+$ calc.: 405.1662; found: 405.1662.

IR (ATR, neat, cm$^{-1}$): 3305 (br), 2901 (w), 1635 (s), 1599 (m), 1476 (w), 1445 (w), 1324 (s), 1044 (s), 920 (m).

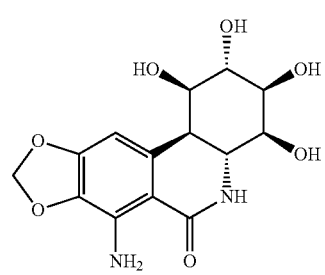

52

Synthesis of 7-aminopancratistatin 52: 7-Aminopancratistatin 52 was prepared using the procedure to synthesize 7-aminolycoricidine 47. N,N-diallylaminopancratistatin S10 (44.0 mg, 0.11 mmol) was subjected to the reaction conditions. The residue was purified by flash chromatography (wet loaded with H$_2$O and purified using Cis-functionalized SiO$_2$, H$_2$O:MeCN=1:0→5:1; and then dry loaded using MeOH, SiO$_2$, CHCl$_3$:MeOH=15:1→9:1) to give the desired compound as a yellow solid [23.0 mg, 0.07 mmol, 65%].

$R_f$=0.36 (SiO$_2$, CHCl$_3$:MeOH=4:1); $[\alpha]_D^{22}$=+59.4 (c=1.0 in DMSO); m.p.=266-267° C. decomposition.

$^1$H NMR (500 MHz, DMSO-d$_6$) δ 6.62 (s, 1H), 6.53 (s, 2H), 6.22 (s, 1H), 5.99 (d, J=5.0 Hz, 2H), 5.32 (d, J=3.9 Hz, 1H), 5.05 (t, J=6.4 Hz, 2H), 4.78 (d, J=7.6 Hz, 1H), 4.24 (dt, J=6.8, 3.1 Hz, 1H), 3.96 (q, J=3.5 Hz, 1H), 3.83 (dt, J=6.1, 3.2 Hz, 1H), 3.69 (ddd, J=9.7, 6.3, 3.0 Hz, 1H), 3.60 (dd, J=12.9, 9.9 Hz, 1H), 2.88 (dd, J=12.8, 2.6 Hz, 1H).

$^{13}$C NMR (126 MHz, DMSO-d$_6$) δ 167.5, 149.1, 136.1, 135.3, 131.5, 106.7, 100.9, 94.8, 73.3, 70.4, 70.3, 68.8, 49.9, 40.3.

HRMS (ESI-TOF, m/z) calcd. For C$_{14}$H$_{17}$N$_2$O$_7$ [M+H]$^+$ calc.: 325.1036; found: 325.1029.

IR (ATR, neat, cm$^{-1}$): 3497 (w), 3387 (m), 3375 (m), 2910 (w), 1639 (s), 1564 (s), 1422 (m), 1029 (s), 921 (m).

Example 9. Synthesis of Differentially Deuterated Narciclasine Analogs

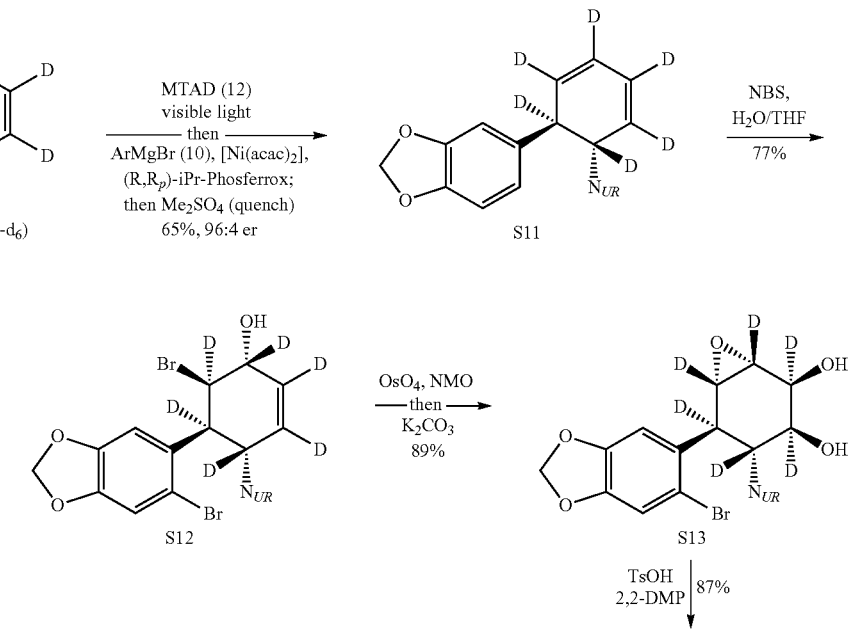

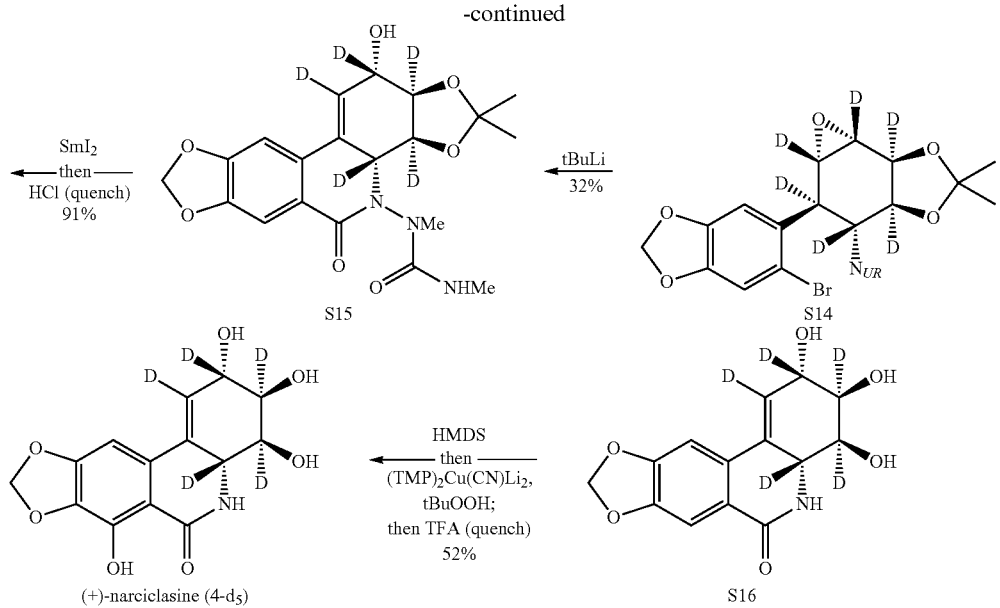

9-1. Synthesis of (+)-narciclasine 4-d₅

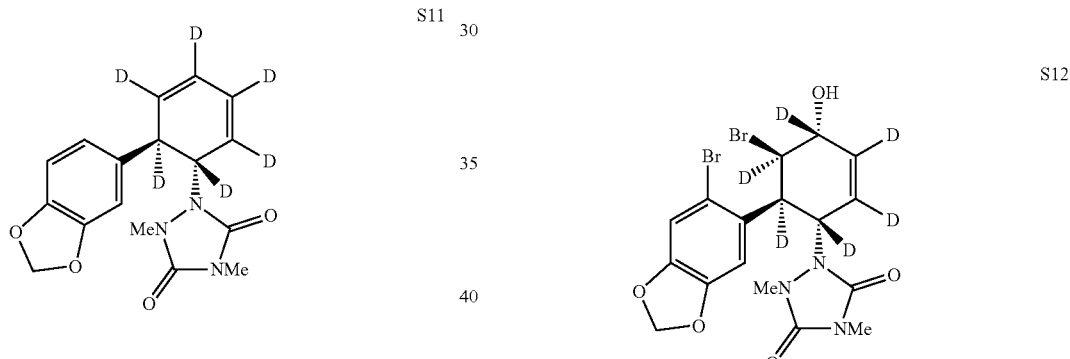

Synthesis of diene S11: Diene S11 was prepared using the procedure to synthesize diene 7, employing the Grignard reagent derived from 3,4-methylenedioxyphenyl bromide 10 and d₆-benzene 9-d₆. The reaction was run on 27 mmol scale, with MTAD (12, 3.00 g) as the limiting reagent. The residue was purified by flash chromatography (SiO₂, hexanes:EtOAc=5:1→3:1) to give the desired compound as a colorless solid [5.79 g, 17.4 mmol, 65%, 96:4 er].

Enantiomeric ratio was determined with HPLC analysis using Daicel Chiracel® OJ-H column, 50% iPrOH in hexanes, 0.8 mL/min, $t_R$(minor)=8.7 min, $t_R$(major)=11.5 min.

$R_f$=0.36 (SiO₂, hexanes:EtOAc=1:1); $[\alpha]_D^{24}$=+248.6 (c=1.0 in CHCl₃); m.p.=114-118° C.

¹H NMR (500 MHz, CDCl₃) δ 6.76 (d, J=1.8 Hz, 1H), 6.69 (d, J=8.0 Hz, 1H), 6.65 (dd, J=8.0, 1.8 Hz, 1H), 6.15-6.10 (m, 1H), 6.08-6.03 (m, 1H), 3.19 (s, 3H), 2.90 (s, 3H).

¹³C NMR (126 MHz, CDCl₃) δ 156.1, 155.0, 147.9, 147.0, 135.3, 130.3 (t, J=24.9 Hz), 126.2 (t, J=24.6 Hz), 124.6 (t, J=25.0 Hz), 122.8 (t, J=24.8 Hz), 121.4, 108.6, 108.2, 101.1, 60.3 (t, J=21.3 Hz), 44.0 (t, J=19.6 Hz), 35.0, 25.5.

HRMS (ESI-TOF, m/z) calcd. For $C_{17}H_{11}D_6N_3O_4K$ [M+K]⁺ calc.: 372.1227; Found: 372.1222.

IR (ATR, neat, cm⁻¹): 2886 (m), 2246 (w), 1763 (w), 1702 (s), 1482 (m), 1034 (m), 930 (m), 768 (m).

Synthesis of bromohydrin S12: Bromohydrin S12 was prepared using the procedure to synthesize bromohydrin 25. Diene S11 (5.69 g, 17.1 mmol) was subjected to the reaction conditions. The residue was purified by flash chromatography (SiO₂, hexanes:EtOAc=4:1→1:1) to provide the desired compound as a colorless solid [6.71 g, 13.2 mmol, 77%].

$R_f$=0.44 (SiO₂, hexanes:EtOAc=1:3); $[\alpha]_D^{22}$=+109.6 (c=1.0 in CHCl₃); m.p.=226-229° C. decomposition.

¹H NMR (500 MHz, CDCl₃) δ 7.12 (s, 1H), 7.01 (s, 1H), 5.97 (s, 2H), 3.15 (s, 3H), 3.11-3.03 (m, 1H), 2.93 (s, 3H).

¹³C NMR (126 MHz, CDCl₃) δ 155.4, 155.3, 147.9, 147.2, 130.5-129.3 (m), 128.9, 127.9 (t, J=23.3 Hz), 115.9, 113.1, 110.2, 102.1, 68.7 (t, J=23.2 Hz), 57.0 (t, J=25.2 Hz), 55.3 (t, J=21.9 Hz), 41.2 (t, J=19.2 Hz), 34.7, 25.7.

HRMS (ESI-TOF, m/z) calcd. For $C_{17}H_{15}D_6Br_2N_4O_5$ [M+NH₄]⁺ calc.: 525.0250; Found: 525.0247.

IR (ATR, neat, cm⁻¹): 3334 (m), 2917 (w), 1767 (m), 1693 (s), 1478 (s), 1237 (m), 1034 (m), 916 (w), 771 (w).

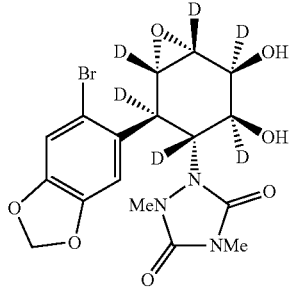

S13

Synthesis of epoxydiol S13: Epoxydiol S13 was prepared using the procedure to synthesize (+)-epoxydiol S6. Bromohydrin S12 (6.71 g, 13.2 mmol) was subjected to the reaction conditions. The residue was purified by flash chromatography (SiO$_2$, CH$_2$Cl$_2$:MeOH=30:1→15:1) to give the desired compound as a colorless solid [4.65 g, 10.1 mmol, 89%].

R$_f$=0.42 (SiO$_2$, CH$_2$Cl$_2$:MeOH=8:1); [α]$_D^{22}$=+110.1 (c=1.0 in CHCl$_3$); m.p.=155-157° C.

NMR analysis of epoxydiol S13 revealed several conformational structures at 20° C., which increased spectrum complexity. Therefore, a variable-temperature NMR spectroscopy was employed, and a full coalescence of the peaks was observed at 100° C. For clarity only the two major conformers at 20° C. are described.

$^1$H NMR (500 MHz, DMSO-d$_6$, 20° C.) δ 7.19 (s, 2H), 7.16 (s, 1H), 7.02 (s, 1H), 6.11 (s, 2H), 6.09-6.04 (m, 2H), 5.73 (s, 1H), 5.64 (s, 1H), 4.91 (s, 2H), 3.23 (s, 3H), 2.88 (s, 3H), 2.79 (s, 3H), 2.45 (s, 3H).

$^1$H NMR (500 MHz, DMSO-d$_6$, 100° C.) δ 7.12 (s, 2H), 6.07 (s, 1H), 6.05 (s, 1H), 5.34-5.29 (m, 1H), 4.44 (s, 1H), 2.99 (s, 3H), 2.84 (s, 3H).

$^{13}$C NMR (126 MHz, DMSO-d$_6$, 20° C.) δ 156.6, 155.8, 155.1, 147.9, 147.7, 147.2, 146.5, 133.4, 132.5, 129.5, 114.1, 112.1, 111.0, 108.8, 108.1, 102.2, 72.5, 71.9, 67.6, 66.9, 65.4, 64.2, 61.5, 59.7, 55.6-54.1 (m)*, 43.0, 42.3, 35.3, 34.8, 31.2, 25.3, 25.2, 24.8. (* Overlap of 2 peaks)

$^{13}$C NMR (126 MHz, DMSO-d$_6$, 100° C.) δ 154.6-154.2 (m)*, 147.4, 147.1, 132.4, 113.6, 111.6, 108.3, 101.7, 66.9-66.5 (m), 65.2-64.5 (m), 59.5-58.8 (m), 54.8-54.1 (m)*, 42.6-41.8 (m), 24.4.* (*Overlap of 2 peaks)

HRMS (ESI-TOF, m/z) calcd. For C$_{17}$H$_{13}$D$_6$BrN$_3$O$_7$ [M+H]$^+$ calc.: 462.0777; Found: 462.0781.

IR (ATR, neat, cm$^{-1}$): 3410 (m), 2908 (w), 1760 (w), 1688 (s), 1477 (s), 1233 (m), 1035 (m), 915 (m), 725 (m).

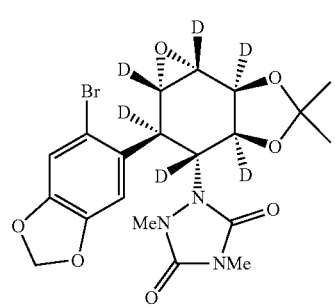

S14

Synthesis of epoxyacetonide S14: Epoxyacetonide S14 was prepared using the procedure to synthesize epoxyacetonide 14. Epoxydiol S13 (4.65 g, 10.1 mmol) was subjected to the reaction conditions. The residue was purified by flash chromatography (SiO$_2$, hexanes:EtOAc=2:1→1:3) to give the desired compound as a colorless solid [4.40 g, 8.76 mmol, 87%].

R$_f$=0.52 (SiO$_2$, CH$_2$Cl$_2$:MeOH=16:1); [α]$_D^{23}$=+22.1 (c=1.0 in CHCl$_3$); m.p.=197-202° C.

NMR analysis of epoxyacetonide S14 revealed several conformational structures at 20° C., which increased spectrum complexity. Therefore, a variable-temperature NMR spectroscopy was employed, and a full coalescence of the peaks was observed at 80° C. For clarity only the two major conformers at 20° C. are described.

$^1$H NMR (500 MHz, DMSO-d$_6$, 20° C.) δ 7.24 (s, 1H), 7.20 (s, 0.2H), 7.15-6.98 (m, 1.2H), 6.09 (s, 1H), 6.07 (s, 1H), 6.05 (s, 0.2H), 6.04 (s, 0.2H), 3.15 (s, 0.6H), 2.94 (s, 3H), 2.84 (s, 0.6H), 2.81 (s, 3H), 1.49-1.42 (m, 3.6H), 1.36-1.30 (m, 3.6H).

$^1$H NMR (500 MHz, DMSO-d$_6$, 80° C.) δ 7.17 (s, 1H), 7.03 (s, 1H), 6.06 (d, J=5.8 Hz, 2H), 2.95 (s, 3H), 2.82 (s, 3H), 1.48 (s, 3H), 1.36 (s, 3H).

$^{13}$C NMR (126 MHz, DMSO-d$_6$, 20° C.) δ 155.7, 155.5, 155.0, 154.0, 147.7 147.6, 147.4, 146.6, 130.6, 129.8, 114.6, 113.6, 113.4, 113.1, 112.8, 112.4, 110.2, 109.9, 108.6, 102.3, 102.2, 72.7-71.8 (m)***, 59.4-58.8 (m)*, 58.2-57.6 (m)*, 51.4-50.6 (m)*, 42.9-42.3 (m)*, 36.0, 32.1, 27.5, 27.3, 26.2, 25.7, 25.2, 25.1. (*Overlap of 2 peaks, *** Overlap of 4 peaks)

$^{13}$C NMR (126 MHz, DMSO-d$_6$, 80° C.) δ 155.0, 154.7, 147.3, 147.1, 130.4, 114.3, 112.0, 109.6, 108.3, 101.8, 72.6-71.6 (m)*, 59.1, 57.6, 50.8, 42.7, 34.3, 27.0, 25.4, 24.7. (* Overlap of 2 peaks) HRMS (ESI-TOF, m/z) calcd. For C$_{20}$H$_{20}$D$_6$BrN$_4$O$_7$ [M+NH$_4$]$^+$ calc.: 521.1339; Found: 521.1339.

IR (ATR, neat, cm$^{-1}$): 2985 (w), 1769 (w), 1704 (s), 1478 (s), 1233 (s), 1218 (s), 1036 (s), 926 (m), 770 (m).

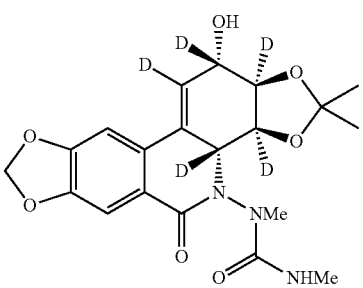

S15

Synthesis of lactam S15: Lactam S15 was prepared using the procedure to synthesize lactam 35. Epoxyacetonide S14 (3.85 g, 7.66 mmol) was subjected to the reaction conditions. The residue was purified by flash chromatography (SiO$_2$, CH$_2$Cl$_2$:MeOH=50:1→30:1) to give the desired compound as a colorless solid [1.04 g, -2.46 mmol, 32%].

R$_f$=0.46 (SiO$_2$, CH$_2$Cl$_2$:MeOH=8:1); [α]$_D^{22}$=-5.0 (c=1.0 in CHCl$_3$); m.p.=152-156° C. decomposition.

NMR analysis of lactam S15 at 20° C. revealed several conformational isomers. When variable-temperature NMR spectroscopy was employed no coalescence of the peaks was observed. Only the two major isomers are described for clarity.

$^1$H NMR (500 MHz, CDCl$_3$) δ 7.53 (s, 1H), 7.51 (s, 0.5H), 7.01 (s, 1H), 6.93 (s, 0.5H), 6.06-6.03 (m, 2H), 6.01 (s, 0.5H), 6.00 (s, 0.5H) 5.05 (q, J=4.8 Hz, 1H), 4.61 (q, J=4.7 Hz, 0.5H), 3.42 (s, 0.5H), 3.29 (s, 1.5H), 3.23 (s, 1H), 3.13 (s, 3H), 2.82 (d, J=4.6 Hz, 1.5H), 2.77 (d, J=4.7 Hz, 3H), 1.49 (s, 4.5H), 1.36 (s, 1.5H), 1.32 (s, 3H).
$^{13}$C NMR (126 MHz, CDCl$_3$) δ 163.07, 162.17, 158.91, 157.54, 152.47, 152.06, 148.69, 148.40, 129.41, 128.59, 127.33, 127.1, 126.9-126.5 (m), 126.4-126.1 (m), 120.40, 120.15, 111.14, 110.20, 107.76, 107.73, 102.29, 102.16, 101.82, 101.25, 79.23-78.36 (m), 78.32-77.53 (m)*, 75.99 (d, J=20.8 Hz), 71.48 (t, J=21.0, 17.6 Hz), 70.43 (t, J=19.7, 10.9 Hz), 62.51 (t, J=23.7, 19.7 Hz), 60.47 (t, J=21.7, 17.0 Hz), 38.58, 31.91, 27.67, 27.45, 27.32, 27.10, 24.96, 24.77. (* Overlap of 2 peaks) HRMS (ESI-TOF, m/z) calcd. For C$_{20}$H$_{22}$D$_5$N$_4$O$_7$ [M+NH$_4$]$^+$ calc.: 440.2188; Found: 440.2192.
IR (ATR, neat, cm$^{-1}$): 3353 (m), 2922 (w), 1650 (s), 1528 (m), 1478 (s), 1213 (s), 1035 (m), 933 (m), 757 (s).

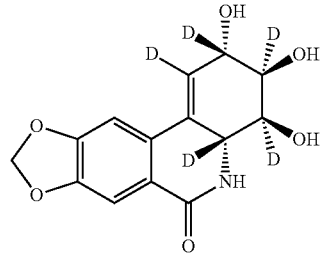

S16

Synthesis of (+)-d$_5$-lycoricidine S16: (+)-d$_5$-Lycoricidine S16 was prepared using the procedure to synthesize (+)-lycoricidine 3. Lactam S15 (945.7 mg, 2.39 mmol) was subjected to the reaction conditions. The residue was purified by flash chromatography (wet loaded with DMSO and purified using C$_{18}$-functionalized SiO$_2$, H$_2$O:MeOH=1:0→5:1) to give the desired compound as an colorless solid [606.7 mg, 2.048 mmol, 91%].
R$_f$=0.38 (SiO$_2$, CHCl$_3$:MeOH=4:1); [α]$_D^{23}$=+127.4 (c=1.0 in DMSO); m.p.=213-216° C. decomposition.
$^1$H NMR (500 MHz, DMSO-d$_6$) δ 7.32 (s, 1H), 7.26 (s, 1H), 7.16 (s, 1H), 6.13-6.12 (m, 1H), 6.11-6.10 (m, 1H), 5.14 (s, 2H), 4.95 (s, 1H).
$^{13}$C NMR (126 MHz, DMSO-d$_6$) δ 163.2, 151.0, 147.2, 131.8, 130.0, 123.3 (t, J=13.0 Hz), 121.9, 106.2, 103.4, 101.9, 72.0 (t, J=23.1 Hz), 68.6 (t, J=20.9 Hz), 68.5 (t, J=20.8 Hz), 52.3 (t, J=17.6 Hz) HRMS (ESI-TOF, m/z) calcd. For C$_{14}$H$_{12}$D$_5$N$_2$O$_6$ [M+NH$_4$]$^+$ calc.: 314.1395; Found: 314.1381.
IR (ATR, neat, cm$^{-1}$): 3353 (s), 3273 (s), 2916 (m), 1649 (s), 1467 (s), 1382 (s), 1251 (m), 1102 (s), 1016 (s).

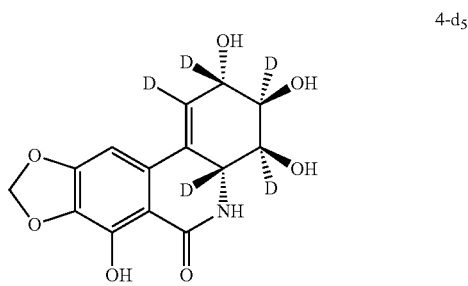

4-d$_5$

Synthesis of (+)-narciclasine 4-d$_5$: (+)-Narciclasine 4-d$_5$ was prepared using the procedure to synthesize (+)-narciclasine 4. (+)-lycoricidine S16 (100 mg, 337 μmol) was subjected to the reaction conditions. The residue was purified by flash chromatography (wet loaded with DMSO and purified using C$_{18}$-functionalized SiO$_2$, H$_2$O:MeCN=1:0→5:1) to give (+)-narciclasine 4-d$_5$ as an colorless solid [55.2 mg, 177 μmol, 52%].
R$_f$=0.33 (SiO$_2$, CHCl$_3$:MeOH=4:1); [α]$_D^{22}$=+159.3 (c=1.0 in DMSO); m.p.=202-218° C. decomposition.
$^1$H NMR (500 MHz, DMSO-d$_6$) δ 13.25 (s, 1H), 7.86 (s, 1H), 6.86 (s, 1H), 6.10-6.07 (m, 2H), 5.16 (s, 1H), 5.13 (s, 1H), 4.98 (s, 1H).
$^{13}$C NMR (126 MHz, DMSO-d$_6$) δ 168.9, 152.3, 144.8, 133.4, 132.1, 129.2, 124.4 (t, J=24.2 Hz), 105.5, 102.1, 95.8, 71.7 (t, J=17.7 Hz), 68.4 (m), 68.3 (m), 52.4 (t, J=20.8 Hz).
HRMS (ESI-TOF, m/z) calcd. For C$_{14}$H$_9$D$_5$NO$_7$ [M+H]$^+$ calc.: 313.1084; Found: 313.1075.
IR (ATR, neat, cm$^{-1}$): 3442 (m), 3206 (m), 2912 (m), 1673 (s), 1428 (s), 1366 (s), 1229 (m), 1084 (s), 1015 (s).

9-2. Synthesis of (+)-narciclasine 4-d$_2$

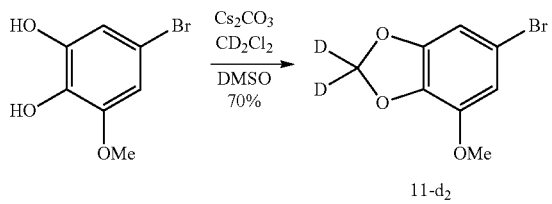

11-d$_2$

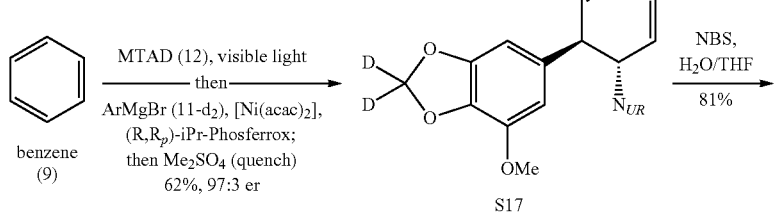

S17

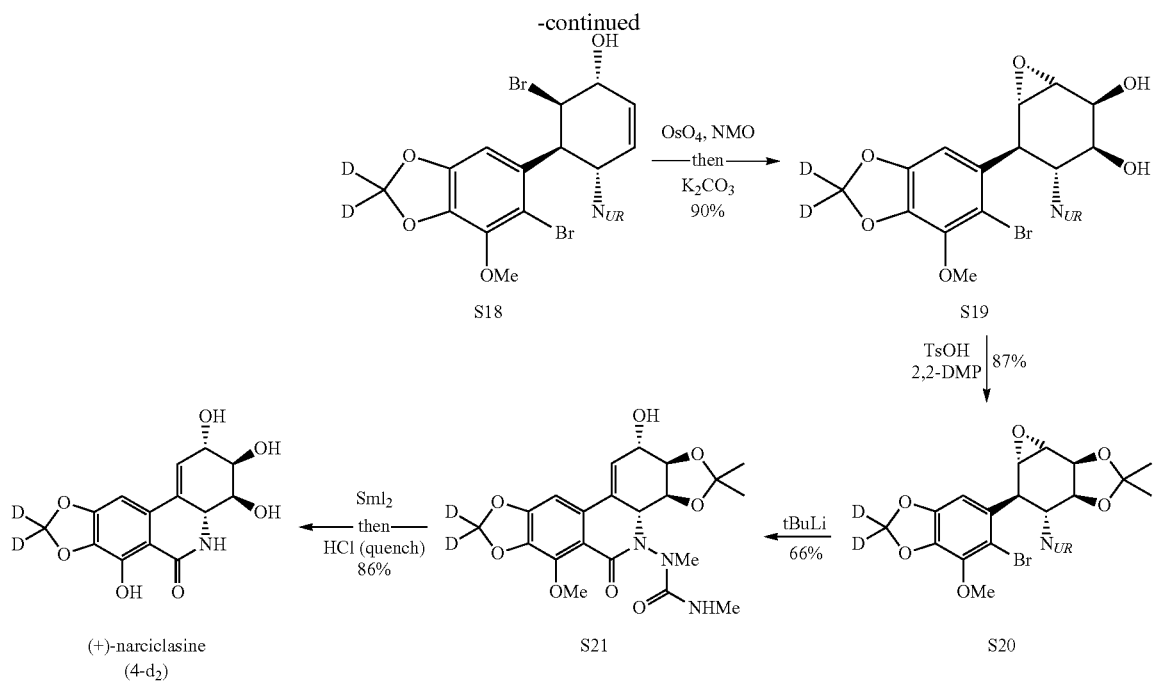

Synthesis of bromide 11-d$_2$: In a round bottom flask equipped with a reflux condenser, a solution of 5-bromo-3-methoxy-1,2-benzenediol (prepared according to the literature procedure: J. Am. Chem. Soc. 1998, 120, 5341) (28.4 g, 130 mmol, 1.0 equiv.) and Cs$_2$CO$_3$ (63.4 g, 194 mmol, 1.5 equiv.) in DMSO (259 mL) and CD$_2$Cl$_2$ (15 mL) was heated to 80° C. and stirred for 2 hours. Then, the solution was allowed to cool to 25° C. before being diluted with water (400 mL) and diethylether (400 mL). The phases were separated and the aqueous phase was extracted with diethylether (3×300 mL). The combined organics were washed with brine (500 mL) and water (500 mL), dried over MgSO$_4$, filtered, and concentrated. The residue was purified by flash chromatography (SiO$_2$, hexanes:EtOAc=100:1→50:1) to give the desired compound as a colorless solid [21.2 g, 91 mmol, 70%].

R$_f$=0.66 (SiO$_2$, hexanes:EtOAc=5:1); m.p.=80-82° C.

$^1$H NMR (500 MHz, CDCl$_3$) δ 6.77-6.58 (m, 2H), 3.88 (s, 3H).

$^{13}$C NMR (126 MHz, CDCl$_3$) δ 149.6, 144.3, 135.0, 113.4, 111.1, 106.3, 102.0-100.7 (m), 56.9.

HRMS (ESI-TOF, m/z) calcd. For C$_8$H$_5$D$_2$O$_3$Br [M]$^+$ calc.: 231.9704; Found: 231.9695.

IR (ATR, neat, cm$^{-1}$): 3087 (w), 2975 (w), 2135 (w), 1625 (s), 1485 (s), 1420 (s), 1226 (s), 1129 (s), 987 (m), 814 (m).

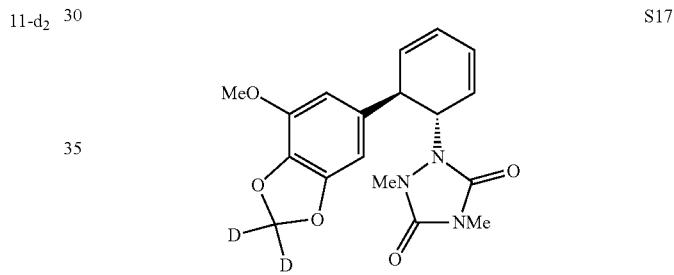

Synthesis of diene S17: Diene S17 was prepared using the procedure to synthesize diene 8, employing the Grignard reagent derived from bromide 11-d$_2$. The reaction was run on 25 mmol scale, with MTAD (12, 2.80 g) as the limiting reagent. The residue was purified by flash chromatography (SiO$_2$, hexanes:EtOAc=5:1→3:1) to give the desired compound as a colorless solid [5.52 g, 15.4 mmol, 62%, 97:3 er].

Enantiomeric ratio was determined with HPLC analysis using Daicel Chiracel® OJ-H column, 50% iPrOH in hexanes, 0.8 mL/min, t$_R$(minor)=13.1 min, t$_R$(major)=20.1 min.

R$_f$=0.35 (SiO$_2$, hexanes:EtOAc=1:1); [α]$_D^{23}$=+200.3 (c=1.0 in CHCl$_3$); m.p.=119-121° C.

$^1$H NMR (500 MHz, CDCl$_3$) δ 6.46 (s, 1H), 6.37 (s, 1H), 6.12 (ddd, J=9.3, 5.2, 2.8 Hz, 1H), 6.08-6.03 (m, 1H), 5.85 (dd, J=9.3, 3.2 Hz, 1H), 5.72-5.67 (m, 1H), 5.15 (dt, J=13.8, 3.2 Hz, 1H), 3.91-3.86 (m, 1H), 3.85 (s, 3H), 3.20 (s, 3H), 2.91 (s, 3H).

$^{13}$C NMR (126 MHz, CDCl$_3$) δ 156.2, 155.1, 149.1, 143.5, 136.1, 134.6, 130.8, 126.6, 125.7, 123.5, 107.6, 102.4, 101.5-100.6 (m), 61.0, 56.7, 45.1, 35.2, 25.5.

HRMS (ESI-TOF, m/z) calcd. For C$_{18}$H$_{17}$D$_2$N$_3$O$_5$Na [M+Na]$^+$ calc.: 382.1348; Found: 382.1351.

IR (ATR, neat, cm$^{-1}$): 2932 (m), 2255 (w), 1766 (m), 1703 (s), 1452 (m), 1228 (m), 1129 (m), 946 (m), 758 (m).

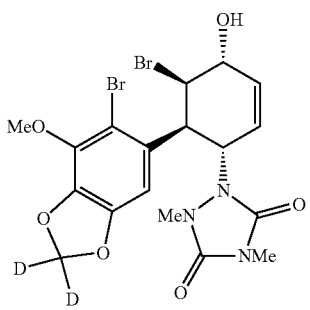

S18

Synthesis of bromohydrin S18: Bromohydrin S18 was prepared using the procedure to synthesize bromohydrin 25. Diene S17 (5.32 g, 14.8 mmol) was subjected to the reaction conditions. The residue was purified by flash chromatography (SiO$_2$, hexanes:EtOAc=4:1→1:1) to provide the desired compound as a colorless solid [6.40 g, 12.0 mmol, 81%].

$R_f$=0.56 (SiO$_2$, hexanes:EtOAc=1:3); $[\alpha]_D^{20}$=+121.6 (c=1.0 in CHCl$_3$); m.p.=250-252° C. decomposition.

NMR analysis of bromohydrin S18 revealed several conformational structures at 20° C., which increased spectrum complexity. Unfortunately, when variable-temperature NMR spectroscopy was employed no coalescence of the peaks was observed.

$^1$H NMR (500 MHz, CDCl$_3$) δ 6.89 (s, 1H), 6.82 (s, 0.1H), 6.12-6.06 (m, 1.1H), 5.99-5.95 (m, 0.1H), 5.92-5.85 (m, 1H), 5.35 (bs, 0.1H), 5.17 (bs, 1H), 4.68-4.51 (m, 2.2H), 4.33 (s, 1H), 4.30 (s, 0.1H), 4.03 (s, 3H), 3.94 (s, 0.3H), 3.17 (s, 0.3H), 3.15 (s, 3H), 2.97 (s, 3H), 2.92 (s, 0.3H), 2.76-2.55 (m, 1.1H).

$^{13}$C NMR (126 MHz, CDCl$_3$) δ 155.4, 155.3, 148.5, 140.6, 137.1, 130.0, 128.3, 110.4, 109.7, 104.5, 101.7-100.9 (m), 69.5, 60.3, 57.3, 55.8, 41.9, 34.7, 25.7.

HRMS (ESI-TOF, m/z) calcd. For C$_{18}$H$_{18}$D$_2$Br$_2$N$_3$O$_6$ [M+H]$^+$ calc.: 533.9844; Found: 533.9837.

IR (ATR, neat, cm$^{-1}$): 3407 (br), 2888 (w), 1763 (m), 1687 (s), 1483 (s), 1228 (m), 1169 (s), 1033 (m), 907 (w), 773 (w).

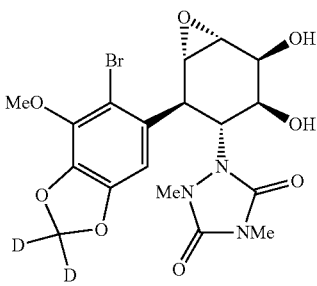

S19

Synthesis of epoxydiol S19: Epoxydiol S19 was prepared using the procedure to synthesize (+)-epoxydiol S6. Bromohydrin S18 (6.30 g, 11.8 mmol) was subjected to the reaction conditions. The residue was purified by flash chromatography (SiO$_2$, CH$_2$Cl$_2$:MeOH=30:1→15:1) to give the desired compound as a colorless solid [5.81 g, 10.6 mmol, 90%].

$R_f$=0.37 (SiO$_2$, CH$_2$Cl$_2$:MeOH=8:1); $[\alpha]_D^{21}$=+102.8 (c=1.0 in CHCl$_3$); m.p.=162-164° C.

NMR analysis of epoxydiol S19 revealed several conformational structures at 20° C., which increased spectrum complexity. Therefore, a variable-temperature NMR spectroscopy was employed, and a full coalescence of the peaks was observed at 100° C. For clarity only the two major conformers at 20° C. are described.

$^1$H NMR (500 MHz, DMSO-d$_6$, 20° C.) δ 6.94 (s, 1H), 6.80 (s, 0.8H), 5.71 (d, J=4.5 Hz, 1H), 5.63 (d, J=4.4 Hz, 0.8H), 4.93-4.88 (m, 1.8H), 4.49 (t, J=10.3 Hz, 1H), 4.38-4.30 (m, 1.8H), 4.26 (d, J=9.7 Hz, 0.8H), 4.08 (d, J=9.8 Hz, 1H), 3.96-3.90 (m, 5.4H), 3.88-3.82 (m, 1.8H), 3.63 (t, J=10.4 z Hz, 0.8H), 3.39-3.35 (m, 1.8H), 3.22 (s, 3H), 2.96 (s, 0.8H), 2.91 (s, 1H), 2.88 (s, 2.4H), 2.79 (s, 3H), 2.46 (s, 2.4H).

$^1$H NMR (500 MHz, DMSO-d$_6$, 100° C.) δ 6.89 (s, 1H), 5.28 (s, 1H), 4.46-4.36 (m, 2H), 4.29-4.06 (m, 2H), 3.94 (s, 3H), 2.97 (br, 3H), 3.02-2.79 (m, 1H) 2.84 (s, 3H).

$^{13}$C NMR (126 MHz, DMSO-d$_6$, 20° C.) δ 155.6, 155.1, 154.0, 152.8, 149.1, 148.9, 140.2, 139.5, 137.0, 136.6, 134.6, 133.6, 109.2, 108.9, 103.3, 102.6, 102.1-101.0 (m)*, 67.7, 67.4, 65.9, 64.7, 60.3, 60.1, 60.0, 59.9, 55.5, 55.2**, 47.1, 43.0, 34.9, 31.2, 25.2, 24.8. (* Overlap of 2 peaks, ** Overlap of 3 peaks)

$^{13}$C NMR (126 MHz, DMSO-d$_6$, 100° C.) δ 154.2*, 148.5, 139.4, 136.5, 133.4, 108.8, 102.8, 101.3-100.7 (m), 100.9, 67.3, 65.2, 59.5, 59.3, 55.0*, 42.9, 24.3. (* Overlap of 2 peaks) HRMS (ESI-TOF, m/z) calcd. For C$_{18}$H$_{19}$D$_2$BrN$_3$O$_8$ [M+H]$^+$ calc.: 488.0638; Found: 488.0634.

IR (ATR, neat, cm$^{-1}$): 3412 (br), 2945 (w), 1761 (w), 1688 (s), 1478 (s), 1234 (m), 1107 (s), 1045 (m), 1007 (m), 771 (m).

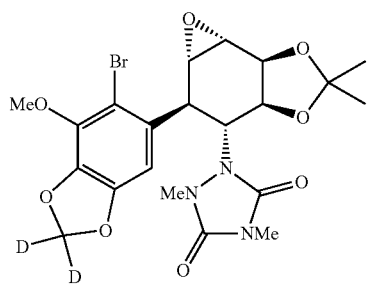

S20

Synthesis of epoxyacetonide S20: Epoxyacetonide S20 was prepared using the procedure to synthesize epoxyacetonide 14. Epoxydiol S19 (5.00 g, 10.2 mmol) was subjected to the reaction conditions. The residue was purified by flash chromatography (SiO$_2$, hexanes:EtOAc=2:1→1:3) to give the desired compound as a colorless solid [4.71 g, 8.91 mmol, 87%].

$R_f$=0.36 (SiO$_2$, hexanes:EtOAc=1:1); $[\alpha]_D^{21}$=+21.5 (c=1.0 in CHCl$_3$); m.p.=213-214° C.

NMR analysis of epoxyacetonide S20 revealed several conformational and rotameric structures at 20° C., which increased spectrum complexity. Therefore, variable-temperature NMR spectroscopy was employed, and a full coalescence of the peaks was observed at 100° C. For clarity only the two major conformers at 20° C. are described.

$^1$H NMR (500 MHz, DMSO-d$_6$, 20° C.) δ 6.85 (s, 1H), 6.79 (s, 0.2H), 5.01 (dd, J=12.6, 10.4 Hz, 0.2H), 4.83 (dd, J=11.8, 5.5 Hz, 1H), 4.44 (s, 1H), 4.25 (dd, J=10.4, 5.2 Hz, 0.2H), 4.17 (dd, J=12.1, 9.8 Hz, 0.2H), 3.97-3.90 (m, 3.6H), 3.83-3.72 (m, 1H), 3.66-3.61 (m, 0.2H), 3.51-3.47 (m, 1H), 3.16 (s, 0.2H), 3.13 (s, 1H), 2.94 (bs, 3.6H), 2.85-2.80 (m, 3.6H), 2.71 (s, 0.2H), 2.68 (s, 1H), 1.49-1.39 (m, 3.6H), 1.36-1.25 (m, 3.6H)

$^1$H NMR (500 MHz, DMSO-d$_6$, 100° C.) δ 6.79 (s, 1H), 4.82 (d, J=5.5 Hz, 1H), 4.50 (s, 1H), 4.18 (s, 1H), 3.94 (s, 3H), 3.89-3.78 (m, 1H), 3.50 (s, 1H), 3.16 (s, 1H), 2.95 (s, 3H), 2.83 (s, 3H), 1.49 (s, 3H), 1.37 (s, 3H).

$^{13}$C NMR (126 MHz, DMSO-d$_6$, 20° C.) δ 155.7, 155.5, 153.9, 153.2, 148.8, 147.9, 140.2, 139.8, 137.1, 136.7, 131.7, 130.8, 110.2, 110.0, 109.7, 109.5, 108.1, 103.1, 102.1-101.0 (m)*, 73.0, 72.9, 72.8, 72.6, 60.0, 59.9, 59.5, 58.5, 57.8, 57.5, 53.0, 51.6, 45.7, 43.4, 36.0, 32.1, 27.4, 27.2, 26.1, 25.7, 25.2, 24.7. (* Overlap of 2 peaks)

$^{13}$C NMR (126 MHz, DMSO-d$_6$, 100° C.) δ 154.8, 154.6, 148.4, 139.7, 136.6, 131.4, 109.5, 109.2, 102.7, 101.4-100.6 (m), 72.8, 72.4, 59.6, 59.4, 57.9, 51.3, 43.1, 34.2, 26.8, 25.2, 24.4.

HRMS (ESI-TOF, m/z) calcd. For C$_{21}$H$_{23}$D$_2$BrN$_3$O$_8$ [M+H]$^+$ calc.: 528.0950; Found: 528.0935.

IR (ATR, neat, cm$^{-1}$): 2988 (w), 1767 (w), 1702 (s), 1479 (s), 1234 (s), 1217 (s), 1075 (s), 1001 (w), 774 (w).

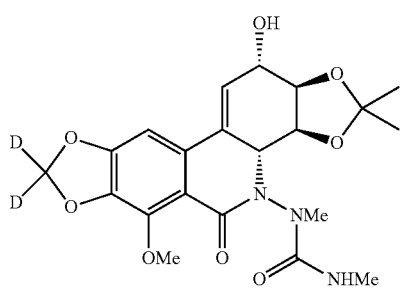

S21

Synthesis of lactam S21: Lactam S21 was prepared using the procedure to synthesize lactam 35. Epoxyacetonide S20 (4.00 g, 7.57 mmol) was subjected to the reaction conditions. The residue was purified by flash chromatography (SiO$_2$, CH$_2$Cl$_2$:MeOH=50:1→30:1) to give the desired compound as a colorless solid [2.23 g, 4.96 mmol, 66%].

R$_f$=0.31 (SiO$_2$, CH$_2$Cl$_2$:MeOH=8:1); [α]$_D^{21}$=+3.1 (c=1.0 in CHCl$_3$); m.p.=161-165° C. decomposition.

NMR analysis of lactam S21 revealed several conformational structures at 20° C., which increased spectrum complexity. Unfortunately, when variable-temperature NMR spectroscopy was employed no coalescence of the peaks was observed.

$^1$H NMR (500 MHz, CDCl$_3$) δ 6.79 (s, 1H), 6.73 (s, 0.5H), 6.41-6.36 (m, 1H), 6.37-6.32 (m, 0.5H), 5.20 (d, J=4.9 Hz, 1H), 4.71-4.65 (m, 0.5H), 4.58-4.52 (m, 0.5H), 4.50 (t, J=7.4 Hz, 1H), 4.43-4.36 (m, 1H), 4.33-4.23 (m, 2H), 4.08 (t, J=6.9 Hz, 1H), 4.03 (t, J=7.7 Hz, 0.5H), 4.00 (s, 3H), 3.98 (s, 1.5H), 3.87-3.80 (m, 0.5H), 3.69-3.59 (m, 1H), 3.25 (s, 1.5H), 3.10 (s, 3H), 2.79 (d, J=4.6 Hz, 1.5H), 2.74 (d, J=4.9 Hz, 3H), 1.48-1.43 (m, 4.5H), 1.34 (s, 1.5H), 1.32 (s, 3H).

$^{13}$C NMR (126 MHz, CDCl$_3$) δ 161.9, 160.8, 159.1, 157.7, 153.1, 152.7, 145.0*, 139.3, 139.2, 131.5, 130.4, 128.0*, 127.3*, 113.0, 112.9, 111.2, 110.0, 102.3-100.8 (m)*, 97.8, 97.2, 79.5, 78.7, 78.3, 76.0, 72.2, 70.6, 62.8, 61.0, 60.9, 60.4, 38.7, 31.8, 27.7, 27.5, 27.5, 27.2, 25.2, 24.9. (* Overlap of 2 peaks) HRMS (ESI-TOF, m/z) calcd. For C$_{21}$H$_{24}$D$_2$N$_3$O$_8$ [M+H]$^+$ calc.: 450.1845; Found: 450.1841.

IR (ATR, neat, cm$^{-1}$): 3364 (br), 2937 (w), 1651 (s), 1529 (m), 1480 (s), 1210 (s), 1029 (m), 967 (m), 757 (s).

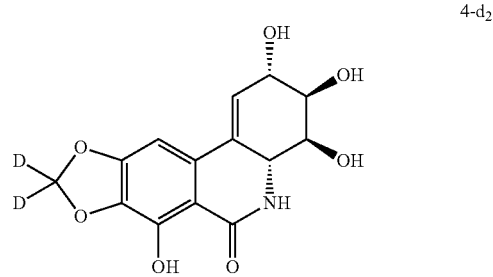

4-d$_2$

Synthesis of (+)-narciclaisne 4-d$_2$: (+)-narciclasine 4-d$_2$ was prepared using the procedure to synthesize (+)-narciclasine 4. Lactam S21 (1.00 g, 2.23 mmol) was subjected to the reaction conditions. The residue was purified by flash chromatography (wet loaded with DMSO and purified using C$_{18}$-functionalized SiO$_2$, H$_2$O:MeCN=1:0→5:1) to give (+)-narciclasine 4-d$_2$ as an colorless solid [589 mg, 1.92 mmol, 86%].

R$_f$=0.33 (SiO$_2$, CHCl$_3$:MeOH=4:1); [α]$_D^{22}$=+149.2 (c=1.0 in DMSO); m.p.=202-216° C. decomposition.

$^1$H NMR (500 MHz, DMSO-d$_6$) δ 13.26 (s, 1H), 7.89 (s, 1H), 6.86 (s, 1H), 6.16-6.14 (m, 1H), 5.21 (d, J=5.9 Hz, 1H), 5.18 (d, J=5.5 Hz, 1H), 5.02 (d, J=3.7 Hz, 1H), 4.19 (ddd, J=8.6, 2.6, 1.4 Hz, 1H), 4.02 (ddd, J=5.9, 4.5, 2.2 Hz, 1H), 3.80 (ddd, J=8.6, 5.5, 2.2 Hz, 1H), 3.72-3.69 (m, 1H).

$^{13}$C NMR (126 MHz, DMSO-d$_6$) δ 168.9, 152.4, 144.8, 133.4, 132.1, 129.3, 124.7, 105.6, 103.0-100.3 (m), 95.8, 72.4, 69.2, 68.8, 52.9.

HRMS (ESI-TOF, m/z) calcd. For C$_{14}$H$_{12}$D$_2$N$_2$O$_7$ [M+H]$^+$ calc.: 310.0896; Found: 310.0895.

IR (ATR, neat, cm$^{-1}$): 3367 (br), 3213 (br), 2907 (m), 1669 (s), 1468 (s), 1372 (s), 1274 (m), 1131 (s), 1003 (s).

Example 10. Cell Viability Assay

Cell Culture and Reagents

A549 and HCT116 cells were cultured in a 37° C., 5% C$_{02}$, humidified atmosphere in RPMI 1640 media supplemented with 1% penicillin/streptomycin and 10% fetal bovine serum. Lycoricidine, narciclasine, and derivatives were dissolved in DMSO and maintained as 10 mM stocks prior to use.

Cell Viability Assay

Cells were seeded in a 96 well plate and allowed to adhere for 3 h. Compounds were added in DMSO at varying concentrations (1% v/v final concentration of DMSO) before the cells were incubated for 72 h. After 72 h, cell viability was assessed via Alamar Blue assay. DMSO-treated cells served as live controls while raptinal-treated cells served as dead controls (Table 2).

TABLE 2

Activity data for compounds.

(+)-7-deoxypancratistatin (1)
A549: 2.9 ± 0.6 μM
HCT116: 1.5 ± 0.1 μM (+)-pancratistatin (2)
A549: 0.75 ± 0.09 μM
HCT116: 0.44 ± 0.03 μM (+)-lycoricidine (3)
A549: 0.73 ± 0.06 μM
HCT116: 0.54 ± 0.03 μM (+)-narciclasine (4)
A549: 0.056 ± 0.004 μM
HCT116: 0.0324 ± 0.0004 μM

TABLE 2-continued

Activity data for compounds.

38
A549: >100 μM
HCT116: >100 μM

39
A549: 44 ± 6 μM
HCT116: 35 ± 9 μM

40
A549: 48 ± 2 μM
HCT116: 50 ± 20 μM

41
A549: >100 μM
HCT116: >100 μM

TABLE 2-continued
Activity data for compounds.
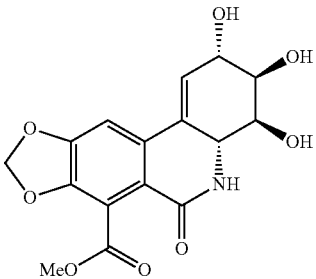 [SMILES: COC(=O)c1c2c(cc3c1C(=O)N[C@@H]1C3=C[C@H](O)[C@@H](O)[C@H]1O)OCO2]
42
A549: 39 ± 5 μM
HCT116: 29 ± 8 μM
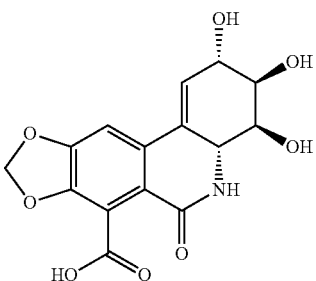 [SMILES: O=C1N[C@@H]2C(=C[C@H](O)[C@@H](O)[C@H]2O)c2cc3c(c(C(=O)O)c21)OCO3]
43
A549: >100 μM
HCT116: 80 ± 20 μM
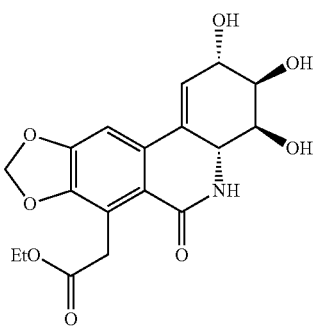
44
A549: 74 ± 10 μM
HCT116: 80 ± 20 μM
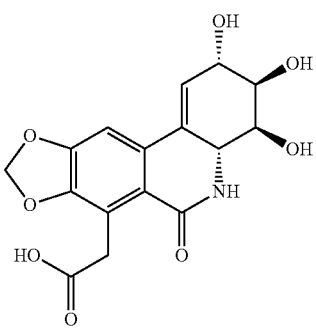 [SMILES: O=C(O)Cc1c2c(cc3c1C(=O)N[C@@H]1C3=C[C@H](O)[C@@H](O)[C@H]1O)OCO2]
45
A549: 89 ± 6 μM
HCT116: 70 ± 20 μM
TABLE 2-continued
Activity data for compounds.
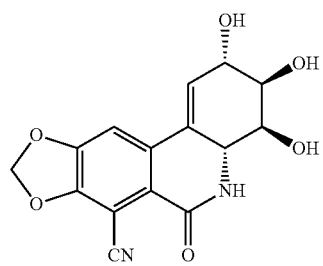 [SMILES: N#Cc1c2c(cc3c1C(=O)N[C@@H]1C3=C[C@H](O)[C@@H](O)[C@H]1O)OCO2]
46
A549: 1.2 ± 0.1 μM
HCT116: 0.48 ± 0.03 μM
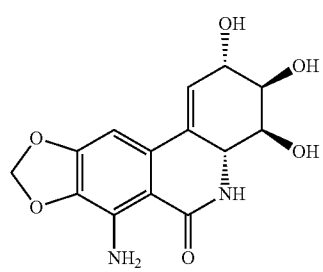 [SMILES: Nc1c2c(cc3c1C(=O)N[C@@H]1C3=C[C@H](O)[C@@H](O)[C@H]1O)OCO2]
47
A549: 0.38 ± 0.04 μM
HCT116: 0.39 ± 0.06 μM
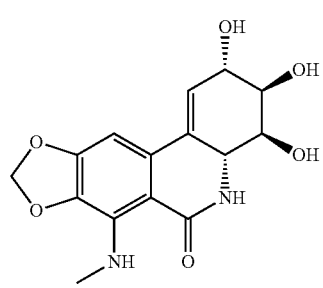 [SMILES: CNc1c2c(cc3c1C(=O)N[C@@H]1C3=C[C@H](O)[C@@H](O)[C@H]1O)OCO2]
48
A549: 28 ± 1 μM
HCT116: 12 ± 2 μM
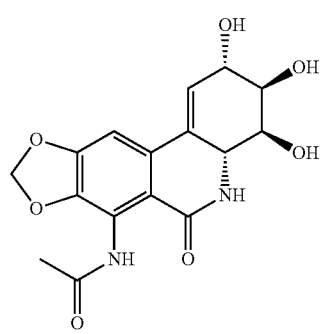 [SMILES: CC(=O)Nc1c2c(cc3c1C(=O)N[C@@H]1C3=C[C@H](O)[C@@H](O)[C@H]1O)OCO2]
49
A549: >100 μM
HCT116: >100 μM TABLE 2-continued Activity data for compounds.

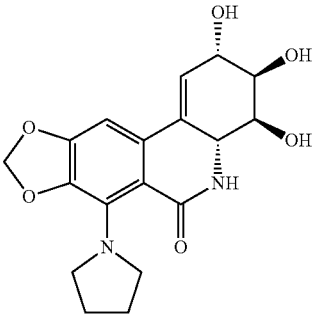 [SMILES: O=C1N[C@@H]2C(=C[C@H](O)[C@@H](O)[C@H]2O)c2cc3c(c(N4CCCC4)c21)OCO3]

50
A549: >100 µM
HCT116: >100 µM

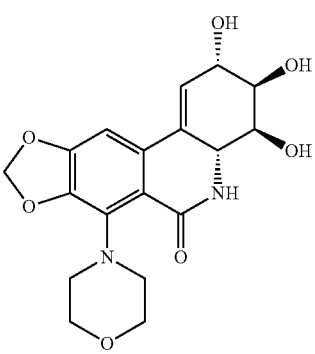 [SMILES: O=C1N[C@@H]2C(=C[C@H](O)[C@@H](O)[C@H]2O)c2cc3c(c(N4CCOCC4)c21)OCO3]

51
A549: 39 ± 4 µM
HCT116: 33 ± 8 µM

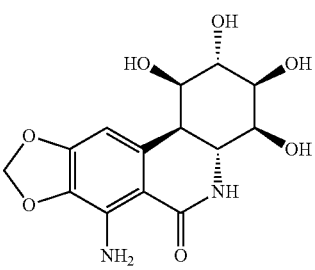 [SMILES: Nc1c2c(cc3c1C(=O)N[C@H]1[C@H](O)[C@H](O)[C@@H](O)[C@H](O)[C@H]31)OCO2]

52
A549: 9 ± 1 µM
HCT116: 3.4 ± 0.2 µM

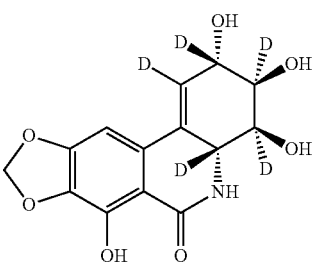

4-d$_5$
A549: 0.066 ± 0.001 µM
HCT116: 0.043 ± 0.002 µM

TABLE 2-continued

Activity data for compounds.

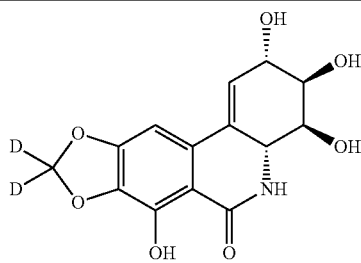

4-d$_2$
A549: 0.07 ± 0.01 µM
HCT116: 0.04 ± 0.01 µM

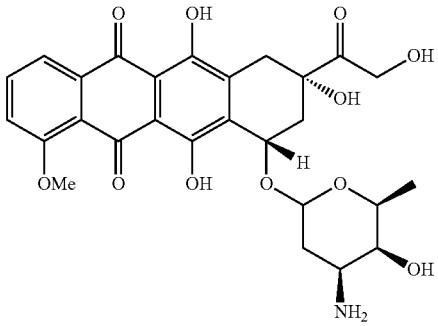 [SMILES: COc1cccc2c1C(=O)c1c(O)c3c(c(O)c1C2=O)C[C@@](O)(C(=O)CO)C[C@@H]3OC1C[C@H](N)[C@H](O)[C@H](C)O1]

doxorubicin
A549: 0.22 ± 0.03 µM
HCT116: 0.147 ± 0.009 µM

Example 11. Solubility Assay

A calibration was made for each compound by diluting a 1 mM DMSO solution to 10, 25, 50, 75, and 100 µM and then measuring their relative UV absorbance by LC-MS using a Kinetex© Evo C-18 50 mm column running a gradient from 5%→90% MeCN in water over 4 minutes at 0.4 mL/min.

The aqueous solubility of each compound was measured using the shake-flask method. 1.0 mg of compound was diluted to 40 mM with water then stirred for 24 hours. Each solution was then filtered, diluted 10-fold, and analyzed by LCMS. The relative UV absorbance of each compound was then compared to its calibration curve to quantify its aqueous solubility.

Calibration curve for 2: y=1.7919±0.0765x−0.0036±0.0060; $t_R$=1.840, λ=235 nm; aq. Solubility=0.56±0.07 mg/ml; Calibration curve for 4: y=2.4813±0.0289x−0.0139±0.0021; $t_R$=1.914, λ=254 nm; aq. Solubility=0.34±0.02 mg/ml; Calibration curve for 47: y=1.1909±0.0389x−0.0086±0.0026; $t_R$=1.775, λ=254 nm; aq. Solubility=3.74±0.20 mg/ml; Calibration curve for 52: y=1.1239±0.0217x−0.0063±0.0017; $t_R$=1.682, λ=235 nm; aq. Solubility=3.46±0.14 mg/ml.

Example 12. Mouse Liver Microsome Assay

A mixture of PBS (pH 7.4), NADPH regenerating system solution A (Corning Life Sciences), and NADPH regenerating system solution B (Corning Life Sciences) was incubated at 37° C. in a shaking incubator for 5 min. Next, compound was added in DMSO (final concentration 50 µM, 0.5% DMSO) before ice-cold mouse liver microsomes (Thermo Fisher, male CD-1 mice, pooled) were added (final protein concentration of 1 mg/mL). An aliquot was immediately removed, quenched with an equal volume of 100 µM internal standard in ice-cold acetonitrile, and centrifuged at 13,000 rcf for 3 min. The supernatant was diluted 1:5 in ddH$_2$O and analyzed by LC-MS. The reactions were incubated at 37° C. in a shaking incubator for 3 h. A second aliquot was removed, quenched and diluted as before and analyzed by LC-MS. The ratio of the areas of analyte:internal standard at 3 hours was compared to the ratio at $t_0$ to determine the percentage of compound remaining. Analysis was performed using a Kinetex® Evo C-18 50 mm column running a gradient from 3%→95% MeCN in water over 9 minutes at 0.4 mL/min. Internal standard=(+)-pancratistatin tetaacetate S4.

Example 13. Additional Compound Characterization

Crystallographic Data for Diene 21

Single crystals of compound 21 were obtained by slow recrystallization from CH$_2$Cl$_2$/hexanes. A suitable crystal was selected, and diffraction data were collected on a Bruker APEX-II CCD diffractometer. The crystal was kept at 100.15 K during data collection. Using Olex2, the structure was solved with the ShelXS structure solution program using Direct Methods and refined with the XL refinement package using Least Squares minimization.

Other crystallographic data and HPLC spectra were collected for select compounds.

Example 14. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |

| (ix) Topical Ointment | wt. % |
|---|---|
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An alkaloid compound of Formula I:

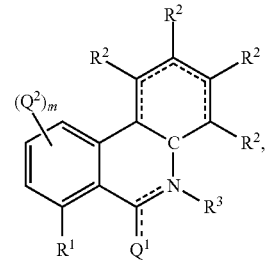

(I)

or a deuterium isotope thereof;
wherein
C is an $sp^3$ carbon atom;
$=\!=\!=$ is a single bond, or an optional double bond wherein two adjacent $=\!=\!=$ do not form consecutive double bonds;
$Q^1$ is $NR^yR^z$, $OR^y$, or $SR^y$, wherein $R^z$ is H or $-(C_1-C_6)$alkyl, and $R^y$ is H, $-(C_1-C_6)$alkyl, or absent when $=\!=\!=$ on $Q^1$ is a double bond;
each $Q^2$ is independently halo, $-(C_1-C_6)$alkyl, $N(R^a)_2$, $OR^a$, $SR^a$, wherein each $R^a$ is independently H or $-(C_1-C_6)$alkyl, or two adjacent $Q^2$ optionally taken together form a ring;
m is 0-3;
$R^1$ is halo, $-(C_1-C_6)$alkyl, $-(C_3-C_6)$cycloalkyl, $SR^b$, $-C(=O)R^c$, $-S(=O)_2R^c$, cyano, nitro, phenyl, $N(R^b)_2$, or a nitrogen heterocycle; or
$R^1$ and $Q^1$ taken together form a 5- or 6-membered ring;
wherein
each $R^b$ is independently H, $-(C_1-C_6)$alkyl, $-C(=O)R^c$, or optionally two $R^b$ taken together form a heterocycle when $R^1$ is $N(R^b)_2$; and
$R^c$ is H, OH, $-(C_1-C_6)$alkyl, $-O(C_1-C_6)$alkyl, $N(R^d)_2$, or phenyl, wherein
each $R^d$ is independently H or $-(C_1-C_6)$alkyl; and
each $R^2$ is independently H, halo, or $OR^e$ wherein each $R^e$ is independently H, $-(C_1-C_6)$alkyl, or a protecting group, or two adjacent $R^2$ taken together optionally form an epoxide, or an alkylenedioxy group;
$R^3$ is H, $-(C_1-C_6)$alkyl, or $-C(=O)R^c$; and
wherein each $-(C_1-C_6)$alkyl, $-(C_3-C_6)$cycloalkyl, phenyl and heterocycle are optionally substituted with or one or more substituents, each $-(C_1-C_6)$alkyl and $-(C_3-C_6)$cycloalkyl is saturated or optionally unsaturated, and each $-(C_1-C_6)$alkyl is unbranched or optionally branched.

2. The compound of claim 1 wherein $R^1$ is cyano or $NH_2$, each $R^2$ is H or D, $R^3$ is H, $Q^1$ is $=O$, and $Q^2$ forms a 1,3-dioxolane ring when m is 2 wherein the bridging methylene moiety is $CH_2$ or $CD_2$ and dioxolane ring is fused at positions ortho and meta relative to $R^1$.

3. The compound of claim 1 wherein $Q^1$ is $OR^y$ and $Q^2$ is $OR^a$, or two adjacent $Q^2$ taken together form an alkylenedioxy group; or $Q^1$ is O, $=\!=\!=$ is a double bond on $Q^1$, and two adjacent $Q^2$ taken together form a methylenedioxy group.

4. The compound of claim 1 wherein the compound of Formula I is a compound of Formula II:

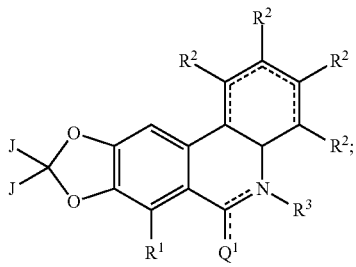

(II)

wherein each J is independently H, D, or CH$_3$.

5. The compound of claim 4 wherein the compound of Formula II is a compound of Formula IIA or IIB:

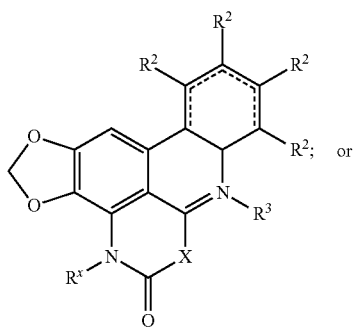

(IIA)

(IIB)

wherein X is O or NR$^x$, and R$^x$ is H or —(C$_1$-C$_6$)alkyl.

6. The compound of claim 4 wherein the compound of Formula II is a compound of Formula III:

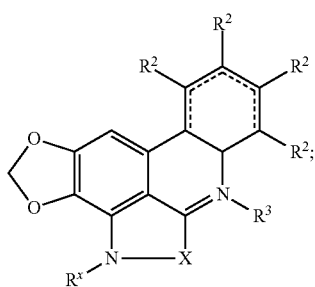

(III)

7. The compound of claim 1 wherein the compound of Formula I is a compound of Formula IV:

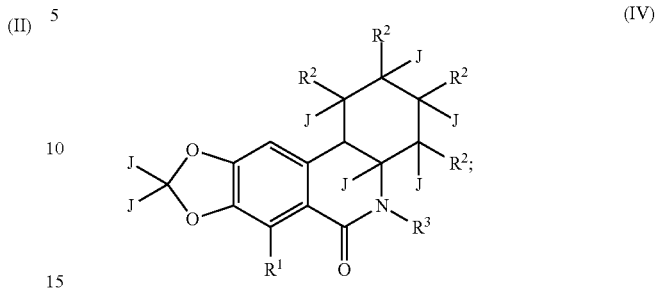

(IV)

wherein each J is independently H or D.

8. The compound of claim 7 wherein R is cyano or N(R$^b$)$_2$.

9. The compound of claim 7 wherein each R$^2$ is independently H or OH.

10. The compound of claim 7 wherein the compound of Formula IV is a compound of Formula IVA:

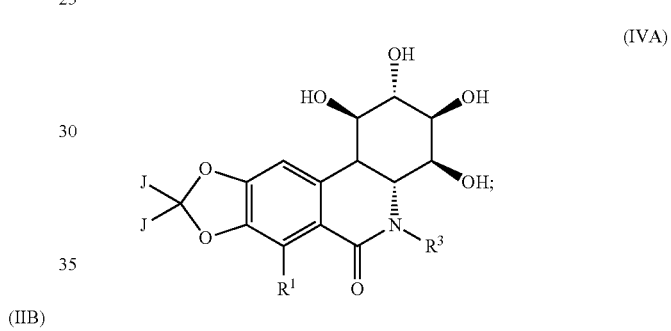

(IVA)

or the enantiomer thereof.

11. The compound of claim 10 wherein R$^1$ is cyano or NH$_2$, and J and R$^3$ are H.

12. The compound of claim 1 wherein the compound of Formula I is a compound of Formula VA, VB, or VC:

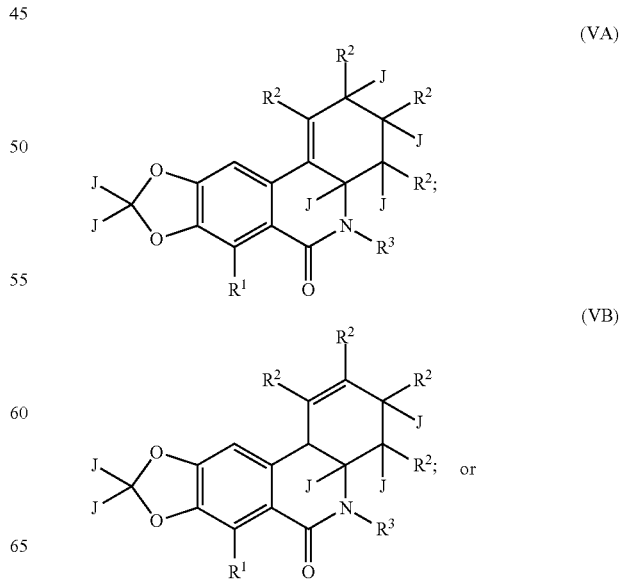

(VA)

(VB)

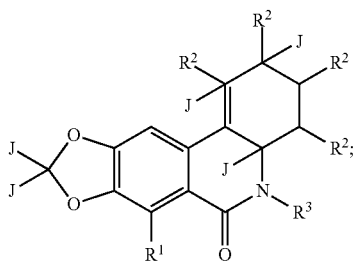

(VC)

wherein each J is independently H or D.

13. The compound of claim 12 wherein $R^1$ is cyano or $N(R^b)_2$.

14. The compound of claim 12 wherein each $R^2$ is independently H or OH, and J and $R^3$ are H.

15. The compound of claim 12 wherein the compound of Formula VA is a compound of Formula VI:

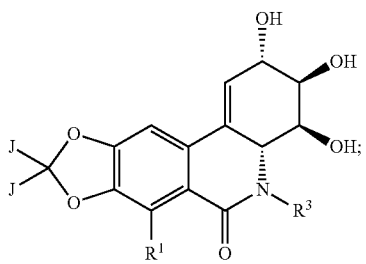

(VI)

or the enantiomer thereof.

16. The compound of claim 15 wherein $R^1$ is cyano or $NH_2$, and J and $R^3$ are H.

17. A method of making an alkaloid compound of Formula VII:

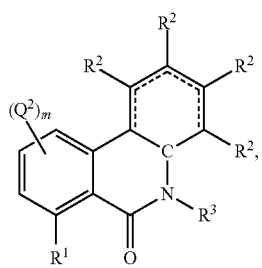

(VII)

or a deuterium isotope thereof;
wherein
C is an $sp^3$ carbon atom;
═══ is a single bond, or an optional double bond wherein two adjacent ═══ do not form consecutive double bonds;
each $Q^2$ is independently halo, —$(C_1$-$C_6)$alkyl, $N(R^a)_2$, $OR^a$, $SR^a$, wherein each $R^a$ is independently H or —$(C_1$-$C_6)$alkyl, or two adjacent $Q^2$ optionally taken together form a ring;
m is 0-3;
$R^1$ is halo, —$(C_1$-$C_6)$alkyl, —$(C_3$-$C_6)$cycloalkyl, $OR^b$, $SR^b$, —$C(═O)R^c$, —$S(═O)_2R^c$, cyano, nitro, phenyl, $N(R^b)_2$, or a nitrogen heterocycle; wherein
each $R^b$ is independently H, —$(C_1$-$C_6)$alkyl, —$C(═O)R^c$, or optionally two $R^b$ taken together form a heterocycle when $R^1$ is $N(R^b)_2$; and
$R^c$ is H, OH, —$(C_1$-$C_6)$alkyl, —$O(C_1$-$C_6)$alkyl, $N(R^d)_2$, or phenyl, wherein
each $R^d$ is independently H or —$(C_1$-$C_6)$alkyl; and
each $R^2$ is independently H, halo, or $OR^e$ wherein each $R^e$ is independently H, —$(C_1$-$C_6)$alkyl, or a protecting group, or two adjacent $R^2$ taken together optionally form an epoxide, or an alkylenedioxy group;
$R^3$ is H, —$(C_1$-$C_6)$alkyl, or —$C(═O)R^c$; and
wherein each —$(C_1$-$C_6)$alkyl, —$(C_3$-$C_6)$cycloalkyl, phenyl and heterocycle are optionally substituted with or one or more substituents, each —$(C_1$-$C_6)$alkyl and —$(C_3$-$C_6)$cycloalkyl is saturated or optionally unsaturated, and each —$(C_1$-$C_6)$alkyl is unbranched or optionally branched;
comprising:
a) contacting a compound of Formula VIIB:

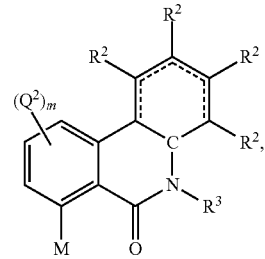

(VIIB)

or a deuterium isotope thereof;
wherein M is H; and
$R^2$, $R^3$, $Q^2$ and m are as defined for Formula VII;
and an organometallic regent to form an organometallic compound of Formula VIIB wherein M is a metal of the organometallic reagent; and
b) quenching the organometallic compound with an electrophile, thereby forming the alkaloid compound of Formula VII.

18. The method of claim 17 wherein the organometallic reagent is a cuprate.

19. The method of claim 17 wherein M of the organometallic compound of Formula VIIB comprises copper.

20. The compound of claim 1 wherein the carbon atom of the $C(sp^3)$-N moiety has an (R)-configuration.

21. The compound of claim 1 wherein the carbon atom of the $C(sp^3)$-N moiety has an (S)-configuration.

* * * * *

UNITED STATES PATENT AND TRADEMARK OFFICE
CERTIFICATE OF CORRECTION

PATENT NO. : 12,084,456 B2
APPLICATION NO. : 17/299365
DATED : September 10, 2024
INVENTOR(S) : David Sarlah, Tanner W. Bingham and Lucas William Hernandez It is certified that error appears in the above-identified patent and that said Letters Patent is hereby corrected as shown below:

In the Claims

In Claim 8, at Column 138, Line 18, delete "wherein R is cyano" and replace with -- wherein $R^1$ is cyano -- therefor.

Signed and Sealed this
Twenty-sixth Day of November, 2024

Katherine Kelly Vidal
*Director of the United States Patent and Trademark Office*